US010052359B2

(12) United States Patent
Ano et al.

(10) Patent No.: US 10,052,359 B2
(45) Date of Patent: Aug. 21, 2018

(54) COMPOSITION FOR ENHANCING MEMORY AND LEARNING FUNCTION AND/OR COGNITIVE FUNCTION

(71) Applicant: KIRIN KABUSHIKI KAISHA, Tokyo (JP)

(72) Inventors: Yasuhisa Ano, Tokyo (JP); Toshiko Kutsukake, Tokyo (JP)

(73) Assignee: KIRIN KABUSHIKI KAISHA, Nakano-ku, Tokyo (JP)

( * ) Notice: Subject to any disclaimer, the term of this patent is extended or adjusted under 35 U.S.C. 154(b) by 0 days.

(21) Appl. No.: 15/315,209

(22) PCT Filed: Jun. 16, 2015

(86) PCT No.: PCT/JP2015/067344
§ 371 (c)(1),
(2) Date: Nov. 30, 2016

(87) PCT Pub. No.: WO2015/194564
PCT Pub. Date: Dec. 23, 2015

(65) Prior Publication Data
US 2017/0209520 A1  Jul. 27, 2017

(30) Foreign Application Priority Data

Jun. 16, 2014 (JP) ................................ 2014-123073
Nov. 10, 2014 (JP) ................................ 2014-228391

(51) Int. Cl.
A61K 38/01 (2006.01)
A61K 38/00 (2006.01)
A61K 38/05 (2006.01)
A61K 38/06 (2006.01)
A61K 38/07 (2006.01)
A61K 38/08 (2006.01)
C07K 5/06 (2006.01)
C07K 5/08 (2006.01)
C07K 5/10 (2006.01)
C07K 7/00 (2006.01)
C07K 7/06 (2006.01)
C07K 7/08 (2006.01)
A23L 33/00 (2016.01)
A23L 33/18 (2016.01)
A23L 33/19 (2016.01)
A23L 33/175 (2016.01)
A23L 33/10 (2016.01)

(52) U.S. Cl.
CPC ............ A61K 38/018 (2013.01); A23L 33/10 (2016.08); A23L 33/175 (2016.08); A23L 33/18 (2016.08); A23L 33/19 (2016.08); A23L 33/40 (2016.08); A23V 2002/00 (2013.01)

(58) Field of Classification Search
CPC ........ A23L 33/10; A23L 33/175; A23L 33/18; A23L 33/19; A23L 33/40; A23V 2002/00; A61K 38/018; A61K 38/01; A61K 38/00; A61K 38/05; A61K 38/06; A61K 38/07; A61K 38/08; C07K 5/06; C07K 5/08; C07K 5/10; C07K 7/00; C07K 7/06; C07K 7/08
USPC ........ 530/300, 326, 327, 328, 329, 330, 331
See application file for complete search history.

(56) References Cited

U.S. PATENT DOCUMENTS

2006/0079454 A1* 4/2006 Reches .............. C07K 5/06078
514/21.91
2008/0009434 A1* 1/2008 Reches ................... A61L 27/38
530/300

FOREIGN PATENT DOCUMENTS

| CN | 102028931 A | 4/2011 |
|---|---|---|
| JP | 63-141998 A | 6/1988 |
| JP | 2004-508025 A | 3/2004 |
| JP | 2005-343815 A | 12/2005 |
| JP | 2010-520274 A | 6/2010 |
| JP | 2011-037785 A | 2/2011 |
| JP | 2012-012358 A | 1/2012 |
| WO | 02/19837 A1 | 3/2002 |
| WO | 2008/108649 A2 | 9/2008 |
| WO | 2012/110652 A1 | 8/2012 |
| WO | 2012/176658 A1 | 12/2012 |

OTHER PUBLICATIONS

UniProt A0A084R3H8, pp. 1-2. Intergrated into UniProtKB/TrEMBL Oct. 29, 2014.*
Takana, "Anti-psychotics for Treatment of BPSD", Nippon Rinsho, 69(10):52-56 (2011).
Hattori, "Behavorial and psychological symptoms of dementia-diagnosis and treatment", Nippon Rinsho, 71(6):981-987 (2013).
Nishimura, "Aging and Mental Disorder", Jpn. J. Geriat., 33:1-3 (1996).
Yoneyama, "Activation of neuronal regeneration signal following neuronal degeneration-involvement of microglia", Folia Pharmacol. Jpn., 142:17-21 (2013).

(Continued)

Primary Examiner — Julie Ha
(74) Attorney, Agent, or Firm — Sughrue Mion, PLLC

(57) ABSTRACT

Compositions, foods, and medicaments for enhancing memory and learning function and/or cognitive function are provided. Compositions, foods, and medicaments for improving brain function and particularly enhancing memory and learning function and/or cognitive function can be provided by including a peptide including an amino acid sequence set forth in any one of SEQ ID NOs 1 to 16 as an active ingredient.

17 Claims, 10 Drawing Sheets

(56) References Cited

OTHER PUBLICATIONS

Wake et al., "Resting Microglia Directly Monitor the Functional State of Synapses In Vivo and Determine the Fate of Ischemic Terminals", The Journal of Neuroscience, 29(13):3974-3980 (2009).
Rahman et al., "Dietary Factors and Cognitive Impairment in Community-Dwelling Elderly", The Journal of Nutrition, Health & Aging, 11(1):49-54 (2007).
Crichton et al., "Dairy intake and cognitive health in middle-aged South Australians", Asia Pac. J. Clin. Nutr., 19(2):161-171 (2010).
Brown et al., "Microglial phagocytosis of live neurons", Nature Reviews Neuroscience, 15:209-216 (2014).
Vallis, "A synaptic role for microglia", Nature Reviews Neuroscience, vol. 15, doi:10.1038/nrn3678 (Jan. 17, 2014).
Grinberg et al., "Insulin-like growth factor-1 abrogates microglial oxidative stress and TNF-α responses to spreading depression", Journal of Neurochemistry, 126:662-672 (2013).
Riazi et al., "Microglial activation and TNFα production mediate altered CNS excitability following peripheral inflammation", PNAS, 105(44):17151-17156 (2008).
Berta et al., "Extracellular caspase-6 drives murine inflammatory pain via microglial TNF-α secretion", The Journal of Clinical Investigation, 124(3):1173-1186 (2014).
Perry et al., "Microglia in neurodegenerative disease", Nature Reviews Neurology, 6:193-201 (2010).
Nakatomi et al., "Neuroinflammation in Patients with Chronic Fatigue Syndrome/Myalgic Encephalomyelitis: An $^{11}$C-(R)-PK11195 PET Study", J. Nucl. Med., 55:945-950 (2014).
Yasui et al., "A Chronic Fatigue Syndrome Model Demonstrates Mechanical Allodynia and Muscular Hyperalgesia via Spinal Microglial Activation", GLIA, 62:1407-1417 (2014).
Couch et al., "Microglial activation, increased TNF and SERT expression in the prefrontal cortex define stress-altered behaviour in mice susceptible to anhedonia", Brain, Behavior, and Immunity, 29:136-146 (2013).
Minao Asano et al., "Inhibition of Prolyl Endopeptidase by Synthetic Peptide Fragments of Human β-Casein," Agricultural and Biological Chemistry, 1991, pp. 825-828, vol. 55, No. 3.
Minoru Sakaguchi et al., "Effects of systemic administration of β-casomorphin-5 on learning and memory in mice," European Journal of Pharmacology, 2006, pp. 81-87, vol. 530.
International Search Report of PCT/JP2015/067344 dated Jul. 28, 2015.

* cited by examiner

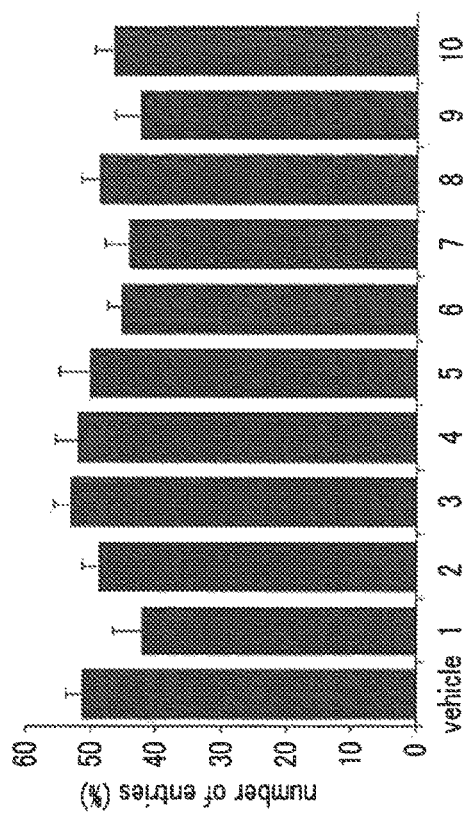
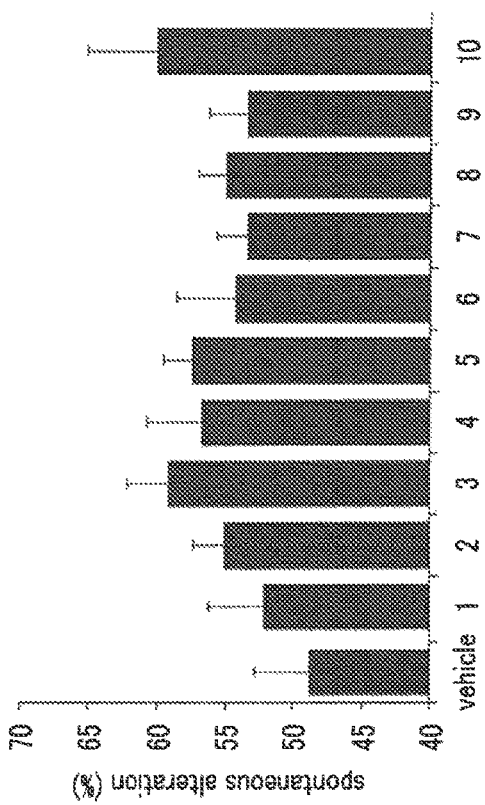
FIG. 2A
FIG. 2B

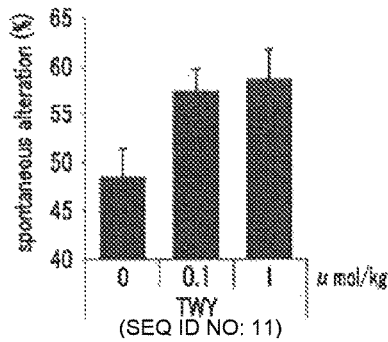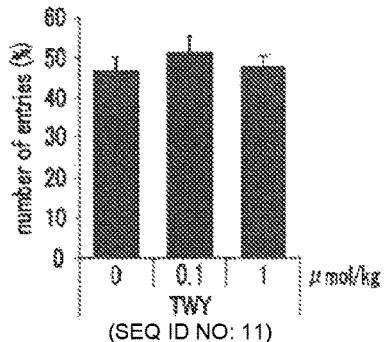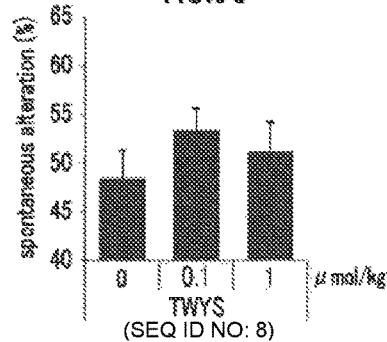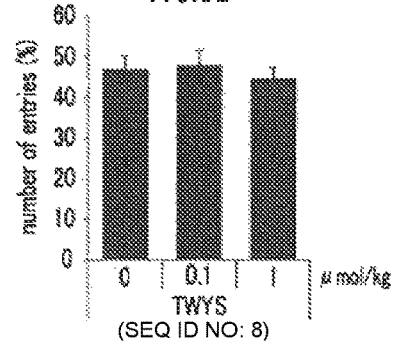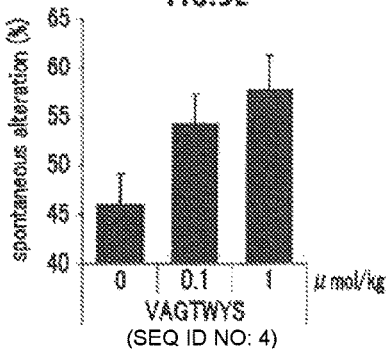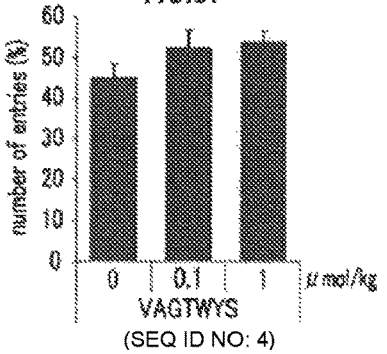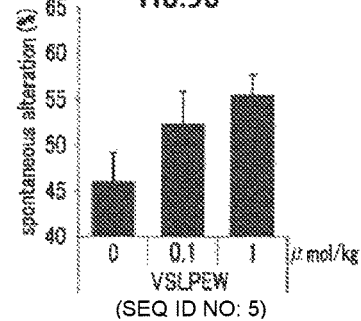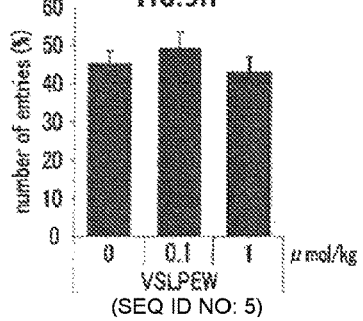

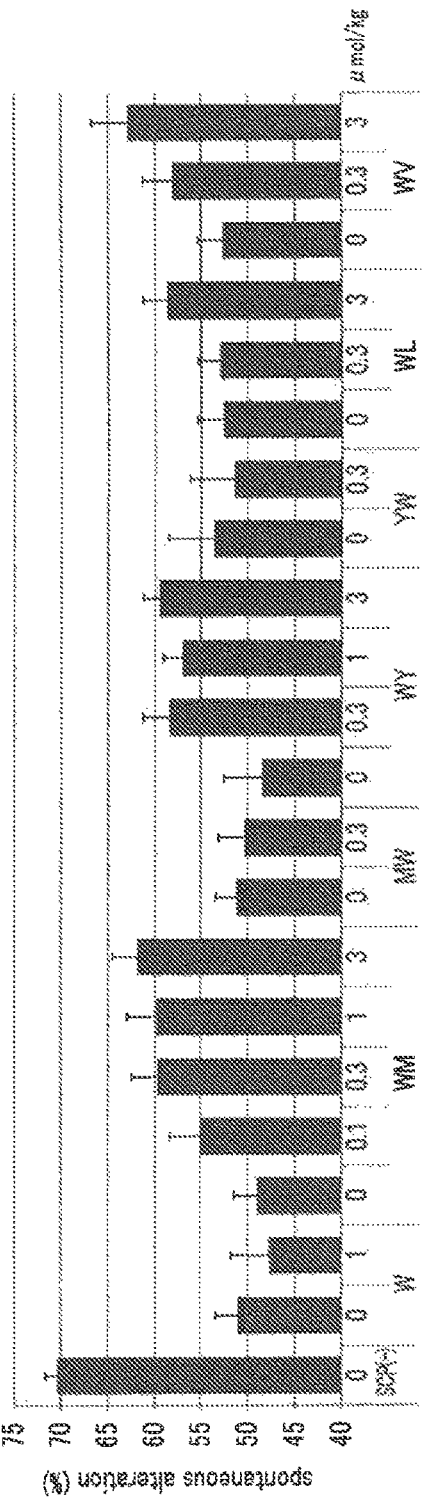
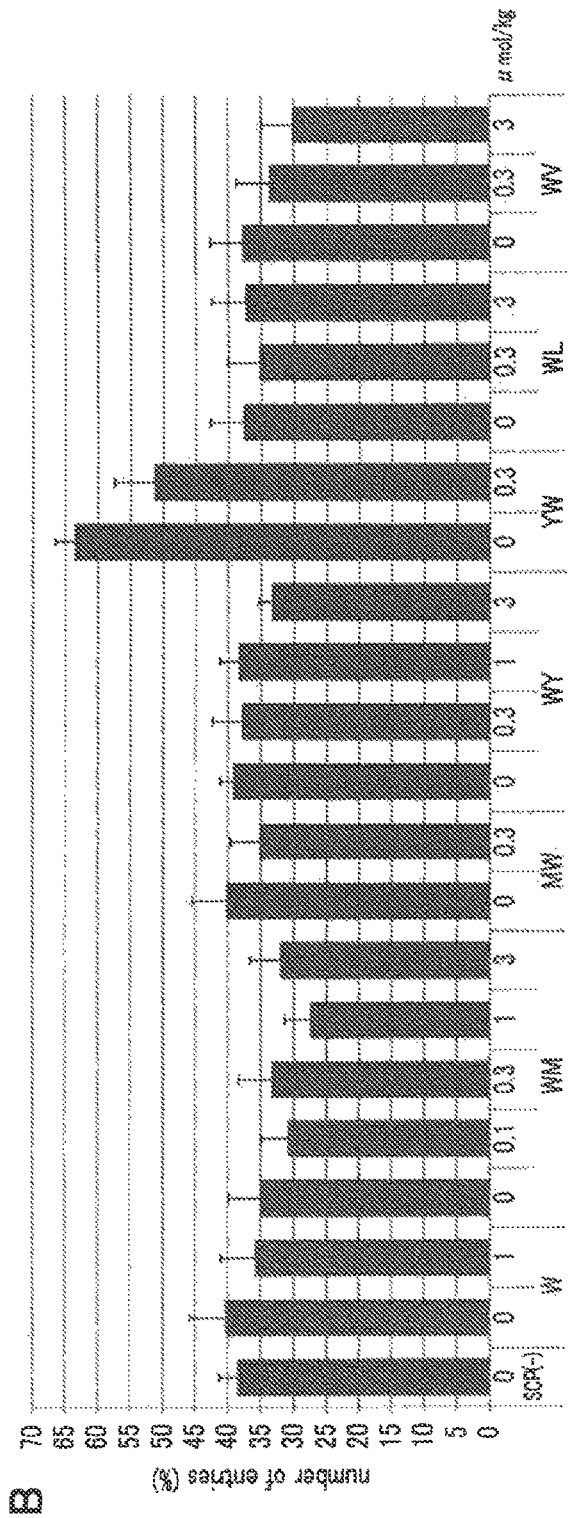

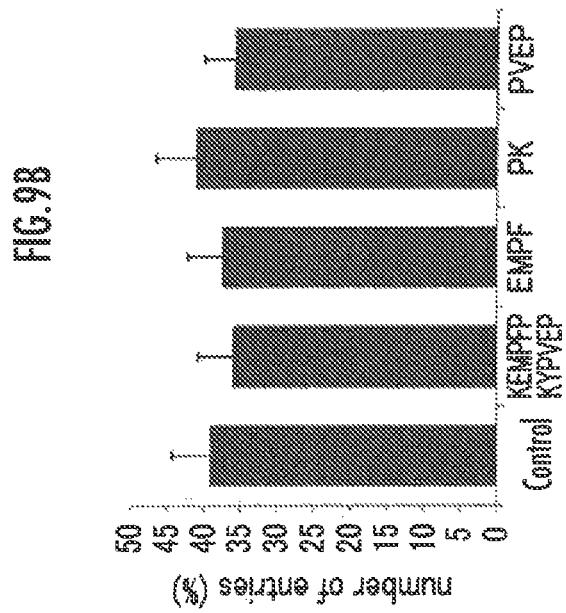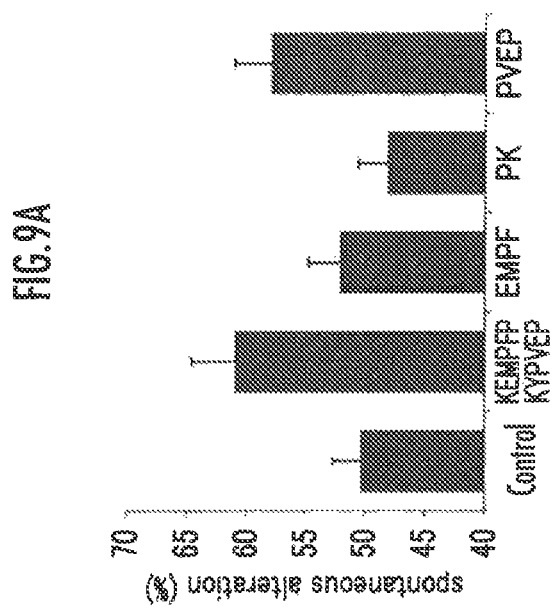

COMPOSITION FOR ENHANCING MEMORY AND LEARNING FUNCTION AND/OR COGNITIVE FUNCTION

CROSS REFERENCE TO RELATED APPLICATIONS

This application is a National Stage of International Application No. PCT/JP2015/067344 filed Jun. 16, 2015, claiming priority based on Japanese Patent Application No. 2014-123073 filed Jun. 16, 2014 and Japanese Patent Application No. 2014-228391 filed Nov. 10, 2014, the contents of all of which are incorporated herein by reference in their entirety.

TECHNICAL FIELD

The present invention relates to peptides having activity to enhance memory and learning function and/or cognitive function, and to compositions, foods, and medicaments containing such a peptide.

BACKGROUND ART

The maintenance, improvement, and amelioration of the brain function are desired by wide generations of people from the youth to the aged. The maintenance, improvement, and amelioration of the memory and the learning ability are important not only for students and working adults studying for entrance and qualifying examinations, but also for conducting daily work and life. The aged desire to prevent the decline of the brain function and maintain, improve, and ameliorate the brain function because the decline of the memory and/or the cognitive function affects quality of life.

Furthermore, the increase of the mental disorder caused by the decline of the brain function associated with the aging in the aged has become a social issue as a result of increase of the aged. Diseases caused by the decline of the brain function include not only dementia represented by Alzheimer's disease, but mental diseases such as depression and delirium have been also reported to be caused by the decline of the brain function (Non-Patent Literature 1 to 3).

The search for substances that increase the brain function has been increasingly conducted as the elucidation of the brain function progresses. in particular, analyses of food ingredients searching for substances that improve the brain function have been conducted since food ingredients are considered to cause no side effects.

For example, an epidemiological investigation of the age group of 39 to 65 years old conducted in Australia has given the result that daily intake of a fermented dairy product enhances the memory (Non Patent Literature 4). The result that the prevalence of cognitive impairment is decreased by intake of a fermented dairy product has been obtained also in the United States of America (Non Patent Literature 5). It is considered from these results that a substance that enhances the memory and learning function and the cognitive function is contained in fermented dairy products. However, these research results are those of epidemiological investigations and the actual active ingredient(s) and the mechanism of action remain unknown.

Identification of the ingredient that enhances the brain function, for example, maintain, improve, and/or ameliorate the memory and learning function and/or the cognitive function in foods that can be consumed daily, should be useful for people in wide generations. Since fermented dairy products are considered to contain an ingredient that enhances the memory and learning function and the cognitive function as described above, products available for wide range of people from the youth to the aged can be developed by identifying the ingredient and use it as a medicament or a food.

Microglia, which are the only immune cells in the brain, have found to have the functions that are essential for maintaining the homeostasis in the brain, such as the phagocytotic removal of waste materials in the brain and the restoration of injured tissue. While the waste material removal in the brain and the promotion of generation of synapses by microglia contribute to the maintenance, improvement and amelioration of the cognitive function, it has been reported that the excessive activation of microglia may induce an inflammatory state and cause the decline of the cognitive function (Non-Patent Literature 6 to 9). Inflammatory cytokines and chemokines, such as TNF-$\alpha$ or the like, produced by excessively activated microglia have been reported to be closely related to morbid states such as pain, depression, and chronic fatigue (Non-Patent Literature 10 to 16). Therefore to control microglial activity is important in preventing arid treating various diseases associated with the brain.

CITATION LIST

Non Patent Literature

Non Patent literature 1:
  Nishimura, Tsuyoshi, 1996, Journal of Japan Geriatrics Society, Vol. 33(1), pp. 1-3
Non Patent Literature 2:
  Hattori, Hideyuki, 2013, Nippon Rinsho Vol. 71(6), pp.981-987
Non Patent Literature 3:
  Tanaka, Toshihisa and Takeda, Masatoshi, 2011, Nippon Rinsho, extra number, pp.52-56
Non Patent Literature 4:
  Crichton, G. E., et al., 2001, Asia. Pac. J. Clin. Nutr., Vol.19(2), pp.161-171
Non Patent Literature 5:
  Rahman, A., et al., 2007, J. Nutr. Health Aging, Vol.11 (1),pp.49-54
Non Patent Literature 6:
  Wake, H., et al., 2009, J. Neurosci., Vol.29(1.3), pp.3974-3980
Non Patent Literature 7:
  Yoneyama, Masanori and Hagita Kiyokazu, 2013, Folia Pharmacologica Japonica, Vol.142, pp.17-21
Non Patent Literature 8:
  Welberg, L, 2014, Nat, Rev. Neurosci., Vol.15, pp.68-69
Non Patent Literature 9:
  Brown, G. C. Nether, J. J., 2014, Nat. Rev. Neurosci. pp.209-216
Non Patent Literature 10:
  Berta, T., et al., 2014, J. Clin.Invest., Vol.124(3), pp.1173-1186
Non Patent Literature 11:
  Riazi, K., et al., 2008, Proc. Natl. Acad. Sci. USA, Vol.105(44), pp.17151-17156
Non Patent Literature 12:
  Grinberg, Y. Y., et at, 2013, J. Neurochem., Vol.126(5), pp.662-672
Non Patent Literature 13:
  Couch, Y., et al., 2013, Brain Behav. Immun. Vol.29, pp.139-146

Non Patent Literature 14:
    Yasui, M., et al., 2014, Cilia, doi: 10.1002/glia.22687
Non Patent Literature 15:
    Nakatomi, Y., et al., 2014, J. Nucl. Med., Vol.55, pp.945-950
Non Patent Literature 16:
    Perry, V. H., et al., 2010, Nat. Rev. Neurol. Vol.6, pp.193-201

SUMMARY OF INVENTION

Technical Problem

An object of the present invention is to find a peptide excellent in improving brain function and particularly enhancing memory and learning function and/or cognitive function and to provide a composition, a food, and a medicament for enhancing memory and learning function and/or cognitive function based on the finding.

Solution to Problem

To achieve the aforementioned object, the present inventors screened peptides derived from milk proteins by the assessment in the Y maze test of model mice of poor memory or the assessment in the activity test of isolated intracerebral microglia as an index, based on the idea that the epidemiologically indicated fermented dairy products contain an ingredient that improves the brain function. As a result, the present inventors have found that particular peptides derived from milk proteins can enhance the memory and learning function and/or the cognitive function and that the peptides can enhance phagocytotic activity and/or anti-inflammatory activity of microglia, thereby completing the present invention.

Accordingly, the present invention is a composition for enhancing memory and learning function and/or cognitive function, comprising a peptide comprising an amino acid sequence set forth in any one of SEQ ID NOs: 1 to 16 or a pharmaceutically acceptable salt or solvate thereof.

In the present invention, the amino acid sequence of the peptide is preferably an amino acid sequence set forth in any one of SEQ ID NOs 1 to 16.

The composition is preferably a food for enhancing memory and learning function and/or cognitive function.

The composition is preferably a medicament for enhancing memory and learning function and/or cognitive function.

The peptide is preferably produced by hydrolysis of a protein contained in a food or food material.

The peptide is preferably obtained by an enzymatic treatment of a milk protein or a food or food material containing the milk protein with an enzymatic agent derived from an microorganism.

The food or food material containing the milk protein is preferably powdered milk, powdered skim milk, or formula milk containing whey or casein or both. Whey is more preferred in terms of the production cost.

The enzymatic agent preferably comprises one or more enzymes selected from a group consisting of an enzyme derived from a microbe belonging to the genus *Aspergillus*, an enzyme derived from a microbe belonging to the genus *Bacillus*, and an enzyme derived from a microbe belonging to the genus *Rhizopus*.

Another aspect of the present invention is a composition for enhancing microglial phagocytotic and/or anti-inflammatory activities, comprising a peptide comprising an amino acid sequence set forth in any one of SEQ ID NOs: 1, 6, 9, 12, 13, 14, and 17 or a pharmaceutically acceptable salt or solvate thereof.

In the aforementioned invention, the amino acid sequence of the peptide is preferably an amino acid sequence set forth in any one of SEQ NOs 1, 6, 9, 12, 13, 14, and 17.

Advantageous Effects of Invention

According to the present invention, peptides excellent in improving brain function and particularly enhancing memory and learning function and/or cognitive function are found and compositions, foods, and medicaments for enhancing memory and learning function and/or cognitive function can be provided.

More specifically, compositions, foods, and medicaments useful for, for example, improving the memory and the learning ability of the youth to people in their prime and improving the memory and the learning ability as well as preventing the decline of the cognitive function of the aged, can be provided.

Compositions, foods, and medicaments useful in maintaining, improving, and ameliorating the cognitive function by enhancing the activity of microglia to remove waste materials that lead to the decline of the cognitive function in the brain as well as enhancing the anti-inflammatory activity of microglia, can be also provided.

The present invention can provide compositions, foods, and medicaments that have little side effects since the active ingredient(s) in the present invention is a peptide ingredient(s) contained in foods that can be consumed daily.

BRIEF DESCRIPTION OF DRAWINGS

FIG. 2A and FIG. 2B illustrate enhancing effects of whey peptide extracts treated with various enzymes on the memory and learning function and the cognitive function.

FIG. 5A to FIG. 5H illustrate enhancing effects of synthetic peptides of whey-derived peptides on the memory and learning function and the cognitive function.

FIG. 6A and FIG. 6B illustrate enhancing effects of the dipeptide WY (SEQ ID NO: 13) on the memory and learning function and the cognitive function.

FIG. 9A and FIG. 9B illustrate enhancing effects of control peptide KEMPFPKYPVEP (SEQ ID NO: 1), and peptides KEMPFP (residues 1-6 of SEQ ID NO: 1), KYPVEP (residues 7-12 of SEQ ID NO: 1), EMPF (residues 2-5 of SEQ ID NO: 1), PK (residues 6-7 of SEQ ID NO: 1) and PVEP (residues 9-12 of SEQ ID NO: 1), on the memory and learning function and the cognitive function.

DESCRIPTION OF EMBODIMENTS

Figure 1A:
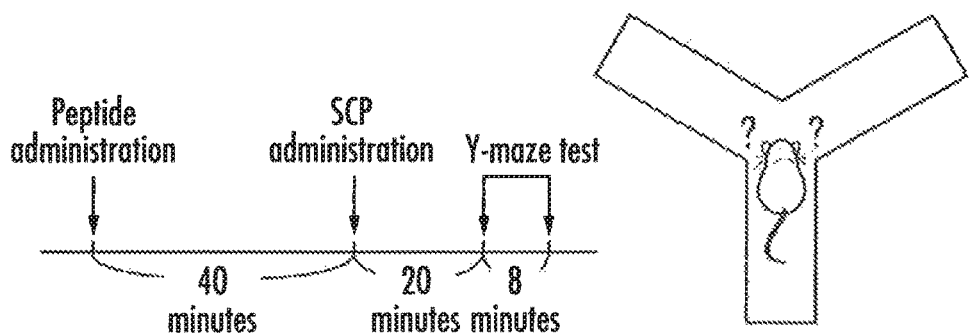
FIG. 1A to FIG. 1C illustrate results of an examination of the enhancing effect of the composition obtained by treating whey with a proteolytic enzyme on the memory and learning function and the cognitive function by the Y-maze test.

In the present invention, the enhancement of memory and learning function includes maintenance, improvement, and/or amelioration of memory and learning function. The maintenance of memory and learning function includes, for example, prevention of decline of the memory and the learning ability associated with aging in the aged. The improvement of memory and learning function includes, for example, improvement of temporal memory and learning function, promotion of fixation of medium-and-long term memory, as well as promotion of the development of the brain. The amelioration of memory and learning function includes, for example, restoring the function that has been decreased by aging or other factors or whose decrease is indicated by a sign(s).

In the present invention, the enhancement of cognitive function includes maintenance, improvement and/or amelioration of cognitive function. The maintenance of cognitive function includes for example, prevention of decrease of intellectual functions such as understanding, judgment, and logic, that is, the cognitive ability. The improvement of cognitive function includes for example, making the cognitive ability; higher than the current state. The amelioration of cognitive function includes for example, restoring the cognitive ability that has decreased or recovering from symptoms with a sign(s) of decrease of the cognitive ability.

The mechanism of action of the peptides to be used according to the present invention is to be elucidated by the future study but it is considered that reinforcing the mechanisms of the brain such as promoting the production of a neurotransmitter results in the enhancement of memory and learning function and/or the cognitive function, such as improvement of cognitive function, improvement of fixation of memory, and suppression of age-related decline of the memory.

The findings according to the present invention also provide, for example, enhancers of memory and learning function and/or cognitive function comprising one of the aforementioned peptides or a composition comprising one of the aforementioned peptides as an active ingredient; methods for enhancing memory and learning function and/or cognitive function comprising administering to a human or an animal one of the aforementioned peptides or a composition comprising one of the aforementioned peptides; and use of one of the aforementioned peptides or a composition comprising one of the aforementioned peptides for enhancing memory and learning function and/or cognitive function.

The peptides to be used according to the present invention may be those obtained by chemical synthesis or those obtained by chemical or enzymatic degradation of a protein or polypeptide material derived from milk, soybean, wheat, egg, animal meat, fish meat, or a fishery product. More specifically, the sequences of the peptides to be used according to the present invention are, for example, contained at least in casein in whey of milk, bovine serum albumin (BSA), glycinin in soybean, glutenin in wheat, lipovitellin in egg yolk, ovalbumin, ovotransferrin, and lysozyme in egg white, the chicken protein collagen, and the like and therefore the aforementioned peptides can be produced by acid hydrolysis, an enzymatic treatment with a protease, or microbe fermentation of these of a food or food material containing these. Such a preparation may be used as a composition according to the present invention as it is, after concentration, or in dried powder after spray-drying or lyophilization. Purification at any degree, including the removal of impurities, salts, enzymes, or the like, may be conducted before use, as needed.

The amino acids constituting a peptide to be used according to the present invention may be composed of only L-amino acids, or may be composed of only D-amino acids, or the peptide may be a peptide containing both. The amino acids may be composed of only naturally occurring amino acids, or may be composed of only modified amino acids in which an amino acid(s) is bonded with an arbitrary functional group(s), such as phosphorylation or glycosylation, or the peptide may be a peptide containing both. When the peptide contains 2 or more asymmetric carbon atoms, the peptide may be an enantiomer, a diastereomer, or a peptide containing both.

Furthermore, a peptide to be used according to the present invention may be a pharmaceutically acceptable salt or solvate thereof. Examples of pharmaceutically acceptable acid addition salts include inorganic acid salts such as hydrochloride, sulfate, and phosphate; and organic acid salts such as acetate, maleate, fumarate, citrate, and methanesulfonate. Examples of pharmaceutically acceptable metal salts include alkali metal salts such as sodium salt and potassium salt; alkaline earth metal salts such as magnesium salt and calcium salt; and aluminum salt and zinc salt. Examples of pharmaceutically acceptable ammonium salts include ammonium and tetramethylammonium salts. Examples of pharmaceutically acceptable organic amine addition salts include morpholine and piperidine addition salts.

The mode of use of the present invention is not particularly limited. For example, the present invention may be used as a medicament or an additive to be used in combination with the medicament or a food or an additive to be used in combination with the food, or the like. The present invention may be used for animals including pets and domestic animals as well as human. For obtaining an effective effect of one of the aforementioned peptides on a human or an animal, the present invention is preferably in a form containing 0.00001-100 mass % of the peptide, more preferably in a form containing 0.0001-100 mass % of the peptide, and most preferably in a form containing 0.001-100 mass % of the peptide. The composition according to the present invention may further contain or be administered or consumed with one or more active ingredients other than the peptide. Examples of compounds or compositions that are known to be effective in maintenance, improvement, or the like of the cognitive function include docosahexaenoic acid (DHA) and ginkgo biloba. Examples of ingredients that decrease amyloid β include anti-amyloid β antibodies.

When a mode of use of the present invention is, for example, a medicament, a pharmaceutical composition comprising, for example, at least one of the aforementioned peptides as an active ingredient may be produced by mixing the at least one peptide with a carrier, an excipient, a binder, a diluent, or the like and the pharmaceutical composition may be administered orally or parenterally. Examples of the triode of oral administration include, but are not limited to, granules, powder, tablets, pills, capsules, and syrup and examples of the mode of parenteral administration include, but are not limited to, injections, drips, nasal administration formulations, and external preparation.

The dose varies depending on the mode of administration, age and body weight of the patient, and nature or severity of the symptoms to be treated. Examples of the range of preferred dose per day per adult in usual oral administration are: first, 0.002-40 g of the peptide, second, 0.002-20 g of the peptide, third, 0.002-2 g of the peptide, fourth, 0.02-40 g of the peptide, fifth, 0.02-20 g of the peptide, sixth, 0.02-2 g of the peptide, seventh, 0.2-40 g of the peptide, eighth, 0.2-20 g of the peptide, and ninth, 0.2-2 g of the peptide. Examples of the range of preferred dose per day per one adult for usual intravenous administration, in the case of parenteral administration such as intravenous administration, are: first, 0.0002-4 g of the peptide, second, 0.0002-2 g of the peptide, third, 0.0002-0.2 g of the peptide, fourth, 0.002-4 g of the peptide, fifth, 0.002-2. g of the peptide, sixth, 0.002-0.2 g of the peptide, seventh, 0.02-4 g of the peptide, eighth, 0.02-2 g of the peptide, and ninth, 0.02-0.2 g of the peptide. As for the doses, the most suitable form may be of course selected as appropriate according to various conditions.

A mode of use of the present invention may be for example, foods and the form thereof is not particularly limited. The foods may be liquid, semiliquid, or solid and encompass forms such as beverages. The foods encompass so-called health foods, functional foods, foods for promoting nutrition, and supplements. The foods encompass functional health foods (foods for specified health use, nutrition functional foods, foods with function claims) such as foods with a label claiming the reduction of disease risk and foods for diseased people. Such foods may be, for example, dairy products such as yogurt and cheese or koji-fermented foods in which the peptide was produced by fermenting a food material such as milk or soybean with a microbe. Examples of the supplements include forms of tablets produced by adding an excipient, a binder, or the like to dry powder of the peptide, kneading the mixture, and compressing the mixture into tablets.

When the present invention is applied to drinks, examples of non-alcoholic thinks include, but are not limited to, mineral water, near water drinks, sports drinks, tea drinks, milk drinks, coffee drinks, drinks containing fruit juice, drinks containing vegetable juice, fruit juice and vegetable juice drinks, and carbonated drinks. Such drinks may be beer-like drinks with alcohol content of less than 1%, such as non-alcoholic beer. The mineral water includes both sparkling mineral water and still mineral water.

The tea drinks among the aforementioned non-alcoholic drinks refer to beverages brewed from leaves (tea leaves) of the tea tree, an evergreen in the family Theaceae, or leaves or grains of plants other than the tea tree for drinking and encompass any of fermented tea, half fermented tea, and non-fermented tea. Specific examples of the tea drinks include Japanese tea (for example, Japanese green tea and Japanese barley tea), black tea, herb tea (for example, jasmine tea), Chinese tea (for example, Chinese green tea, oolong tea), and. Hojicha (roasted tea). The milk drinks refer to beverages made from fresh milk, milk, or foods produced therefrom as a main material and encompass those made from milk itself, as well as those made from processed milk such as, for example, fortified milk, flavored milk, and sweetened degraded milk.

Examples of fruits to be used for the drinks containing fruit juice or the drinks containing fruit juice and vegetable juice include apple, mandarin orange, grape, banana, pear, peach, mango, acai, and blueberry. Examples of vegetables to be used for the drinks containing vegetable juice and the drinks containing fruit juice and vegetable juice include tomato, carrot, celery, pumpkin, celery, cucumber, or the like.

When used as a food, examples of the preferred range of intake per day per one adult in a usual intake form are: first, 0.002-40 g of the peptide, second, 0.00:2-20 g of the peptide, third, 0.002-2 g of the peptide, fourth, 0.02-40 g of the peptide, fifth, 0.02-20 g of the peptide, sixth, 0.02-2 g of the peptide, seventh, 0.2-40 g of the peptide, eighth, 0.2-20 g of the peptide, and ninth, 02-2 g of the peptide. For obtaining an effective effect of one of the aforementioned peptides, the present invention is preferably in a form containing 0.00001-100 mass % of the peptide, more preferably in a form containing 0.0001-100 mass % of the peptide, further preferably in a form containing 0.001-100 mass % of the peptide, even more preferably in a form containing 0.01-90 mass % of the peptide, and most preferably in a form containing 0.1-80 mass % of the peptide. When the peptide is contained in a meal of food or a container subdivided into a meal of food, examples of the content range in a usual formula are: first, 0.002-40 g of the peptide, second, 0.002-20 g of the peptide, third, 0.002-2 g of the peptide, fourth, (102-40 g of the peptide, fifth, 0.02-20 g of the peptide, sixth, 0.02-2 g of the peptide, seventh, 0.2-40 g of the peptide, eighth, 0.2-20 g of the peptide, and ninth, 0.2-2 g of the peptide. When used as a beverage, the present invention is preferably in a form containing 0.00001-10 mass % of the peptide, more preferably in a form containing 0.0001-5 mass % of the peptide, further preferably in a form containing 0.001-5 mass % of the peptide, even more preferably in a form containing 0.01-5 mass % of the peptide, and most preferably in a form containing 0.1-1 mass % of the peptide.

The peptides provided by the present invention have relatively small molecular weights and are therefore well absorbed into the body and excellent in passing through the brain barrier, thereby exhibiting their effects well in brain.

EXAMPLES

The present invention will be described in detail by way of the following examples, but the present invention is not limited by them.

[Preparation of Whey Peptide Extract]

Whey peptide extracts were prepared as follows. 0.125% (w/v) of a food additive protease or peptidase was mixed with a 5% (w/v) whey (Daiichi Kasei Co., Ltd.) aqueous solution and the mixture was reacted at 50 degrees Celsius for 4 hours. The obtained enzymatic reaction solution is filtered with a ultrafilter having a molecular weight cut-off of 10 KDa and the filtrate (hereinafter, also referred to as whey peptide extract) was collected and used for experiments.

[Method of Evaluating Memory and Learning Function and Cognitive Function]

FIG. 1A illustrates a summary of methods of evaluating the memory and learning function and the cognitive function. To 6-week-old male CD-1 mice, 1 mg/kg of the peptide extract or 0.1-3 µmol/kg of a synthetic peptide is orally administered forcibly into stomach and 40 minutes later 0.80 mg/kg of scopolamine hydrochloride was administered intraperitoneally to cause memory impairment. 20 minutes after the intraperitoneal administration of scopolamine, the Y-maze test was conducted to evaluate the spontaneous alternation behavior.

Mice originally have a habit of selecting a route different from the route selected immediately before. Therefore a mouse placed in a Y-maze having 3 arms equivalent in width, length, and the like normally enters the arm different from the arm that the mouse entered immediately before. The Y-maze test is a test to evaluate the short-term memory using the habit of mice.

In the Y-maze test, a Y-maze was used as an experimental apparatus having 3 arms each connected at an angle of 120 degrees and each having a length of 25 cm, a wall high of 20 cm, and a floor width of 5 cm.

Mice were placed in the tip of one of the aims in the Y-maze and the orders of the arms that the mice entered when the mice were allowed to search freely for 8 minutes were recorded. The spontaneous alternation behavior is defined as the behavior in which a mouse selects and enters the different arm three times consecutively. The total number of entries into an arm and the number of spontaneous alternation behavior in a certain time were counted and the spontaneous alternation behavior rate (%) was calculated by Formula (1):

spontaneous alternation behavior rate (%)=the number of spontaneous alternation behavior/(the total number of entries−2)×100 Formula (1)

The higher spontaneous alternation behavior rate indicates the better maintenance of short-term memory. 10 mice per group were used for the experiment and the average and the standard error were determined.

[Examination of Enzymatic Agent]

To analyze whether a peptide that enhances the brain function is contained in whey, which contains milk proteins abundantly, whey was treated with an enzymatic agent derived from a microbe belonging to the genus *Aspergillus*, a microbe belonging to the genus *Bacillus*, or a plant, the Y-maze test was conducted, and whether the product was effective in enhancing the brain function was examined.

Specifically, whey was treated with Protease P "Amano" 3SD (which may be also abbreviated as Amano P; produced by Amano Enzyme Inc.), which is a food additive protease, Protin SD-NY10 (which may be also abbreviated as Protin; produced by Amano Enzyme Inc.), or Bromelain (produced by Amano Enzyme inc.), and the obtained whey peptide extracts were orally administered to mice to evaluate the brain function. The result is illustrated in FIG. 1B and FIG. 1C.

Figure 1B:
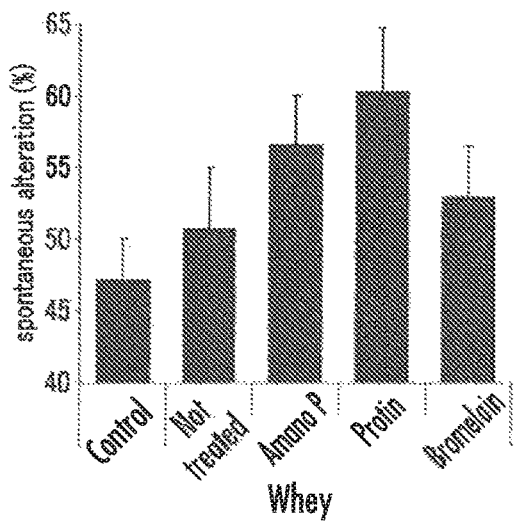
Figure 1C:
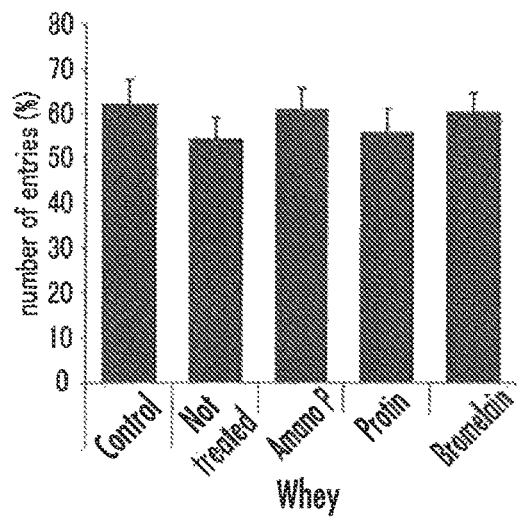

FIG. 1B illustrates the spontaneous alternation behavior rate and FIG. 1C illustrates the total number of entries. The scopolamine (SCP) administration causes no significant change in the total number of entries (FIG. 1C) and whey and whey peptide extract administration cause no change in the activity amount. The control indicates the murine group to which only scopolamine was administered.

As illustrated in FIG. 1B, the ameliorating effect on the brain function was observed in the administration group of the whey peptide extract treated with Amano P, a protease derived from a microbe belonging to the genus *Aspergillus* or the administration group of the whey peptide extract treated with Protin, a protease derived from a microbe belonging to the genus *Bacillus* in comparison with the group (control) given scopolamine alone. However, no amelioration of the brain function was observed in the administrated group of whey without protease treatment (no treatment) or in the administration group of peptide extract treated with Bromelain, which is a protease derived from a plant.

Therefore, whey was treated with 10 types of enzymatic agents (any of which were produced by Amano Enzyme Inc.) set forth in Table 1, including enzymatic agents derived from microbes in the genus *Aspergillus* and the genus *Bacillus*, which exhibited ameliorating effects on the brain function and an enzymatic agent derived from a microbe belonging to the genus *Rhizopus* and evaluation of the memory and learning function and the cognitive function was conducted using a scopolamine model of poor memory similar to the above description (FIG. 2A and FIG. 2B). Distilled water was used as a vehicle.

TABLE 1

| Enzyme No. | Product Name | Origin |
| --- | --- | --- |
| #1 | Newlase F3 | *Rhizopus niveus* |
| #2 | Protease M "Amano" SD | *Aspergillus oryzae* |
| #3 | Protease P "Amano" 3SD | *Aspergillus melleus* |
| #4 | Protin SD-NY10 | *Bacillus amiloliquefeciens* |
| #5 | Thermoase PC10F | *Bacillus stearothermophilus* |
| #6 | Protin SD-AY10 | *Bacillus licheniformis* |
| #7 | ProteAX | *Aspergillus oryzae* |
| #8 | Peptidase R | *Rhizopus oryzae* |
| #9 | Protin NY100 | *Bacillus amiloliquefeciens* |
| #10 | Thermoase C100 | *Bacillus stearothermophilus* |

FIG. 2A illustrates the spontaneous alternation behavior rate and FIG. 2B illustrates the total number of entries. The peptide extracts treated with either of the enzymes exhibited the ameliorating effect on the brain function in the scopolamine model of poor memory.

Since particularly strong activities were observed with Protease P "Amano" 3SD (Amano P, No. 3 in FIG. 2A and FIG. 2B), an enzyme derived from a microbe belonging to the genus *Aspergillus*, and Thermoase C100 (No. 10 in FIG. 2A and FIG. 2B), an enzyme derived from a microbe belonging to the genus *Bacillus*, these enzyme-treated peptides were considered to contain a peptide(s) that is highly effective in ameliorating the brain function. Therefore, a search for an active peptide was conducted in these enzyme-treated whey products.

[Method of Fractioning Peptides]

The whey peptide extracts treated with Amano P or Thermoase C100, which exhibited high ameliorating effects on the brain function were applied to a C18 solid-phase extraction column and then eluted stepwise with aqueous solutions containing 20, 40, 60, or 80% of methanol in water.

The obtained fraction was concentrated and then further fractionated by preparative HPLC. C18 column (10 mm in inner diameter, 250 mm in length, 5 μm in particle size) was used as a separation column and elution was conducted using a graduation of 0% Solution B (100% methanol) at 0 min. to 80% Solution B at 40 min. in Solution A (5% methanol) at a speed of 5 ml/min as the mobile phase.

The eluate was fractionated into some fractions and each fraction was concentrated and dried. Each fraction was redissolved in a solution containing a little methanol and then applied to an analytical HPLC and refractionated. A C18 separation column (4.6 mm in inner diameter, 250 mm in length, and 5 μm in particle size) was used at a column temperature of 70 degrees Celsius.

Elution was conducted using a gradient of 5% Solution B (0.1% TFA/acetonitrile) at 0 min., 20% Solution B at 30 min., and 20% Solution B at 40 min. or 5% Solution B at 0 min. and 80% Solution B at 30 min in Solution A (0.1% TFA) at a speed of 1 ml/min, as the mobile phase. The detection was conducted at UV 220 nm.

The peaks obtained by the analysis were fractionated into several fractions and they were further repeatedly fractionated and collected. Each of the obtained fractions was concentrated and dried to remove TFA and redissolved in a solution containing a little methanol.

These fractions were evaluated for the enhancing effect on the memory and learning function and the cognitive function and peptides contained in the fractions having a high activating ability were further purified. The obtained purified peptides were analyzed by the N-terminal amino acid sequence analysis to obtain amino acid sequences.

Figure 3:
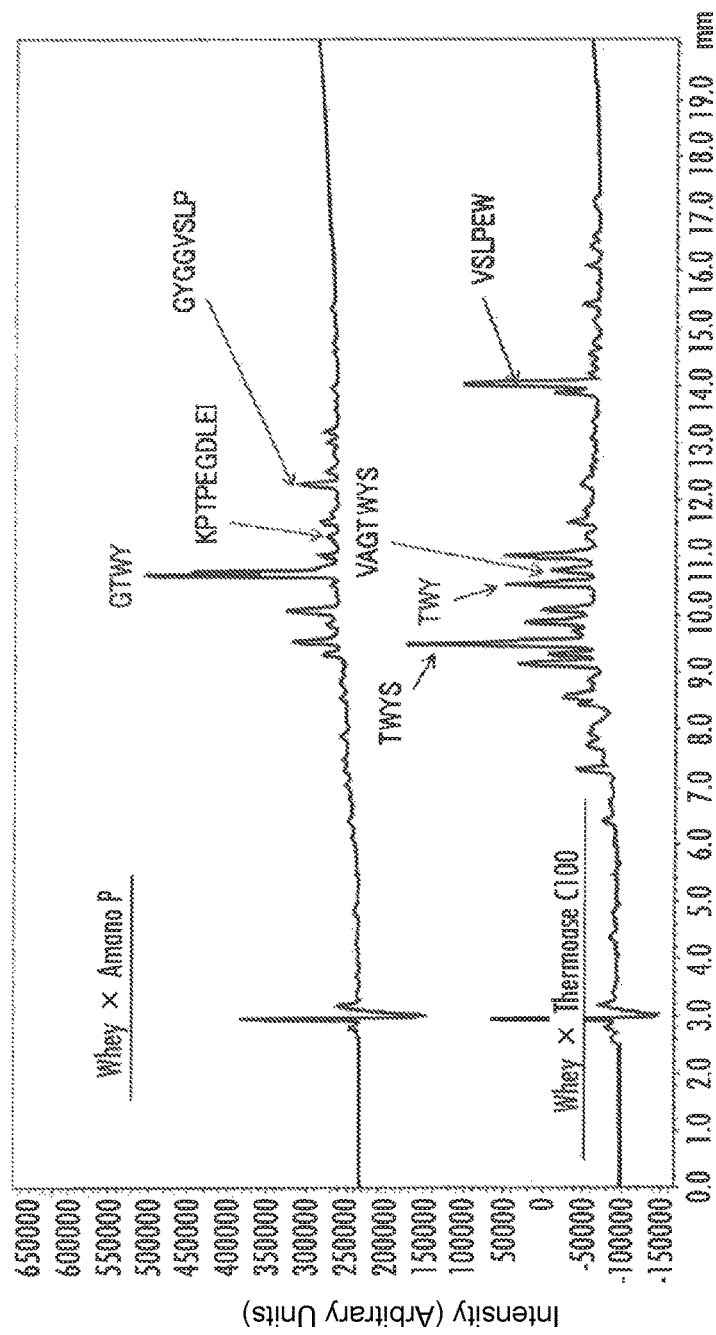
FIG. 3 illustrates HPLC profiles of a whey peptide extract treated with protease P "Amann" 3SD or Thermoase C100, and depicting peptide fragments GTWY (SEQ ID NO: 7), KPTPEGDLEI (SEQ ID NO: 2), GYGGVSLP (SEQ ID NO: 3), TWYS (SEQ ID NO: 8), TWY (SEQ ID NO: 11), VAGTWYS (SEQ ID NO: 4) and VSLPEW (SEQ ID NO: 5).
Figure 4A:
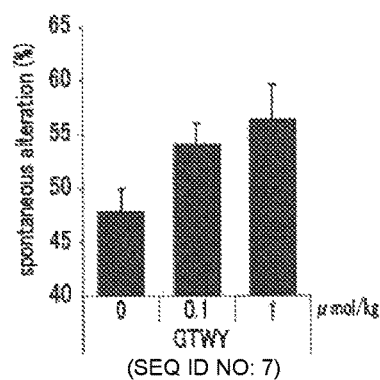
FIG. 4A to FIG. 4F illustrate enhancing effects of synthetic peptides of whey-derived peptides on the memory and learning function and the cognitive function.
Figure 4B:
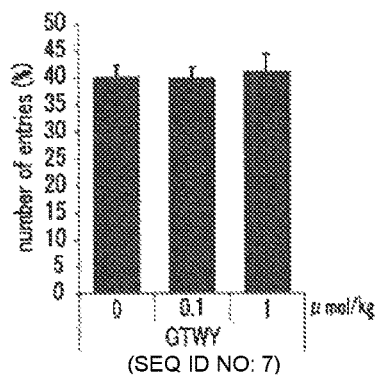
Figure 4C:
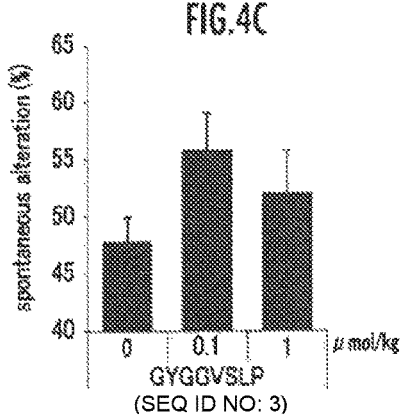
Figure 4D:
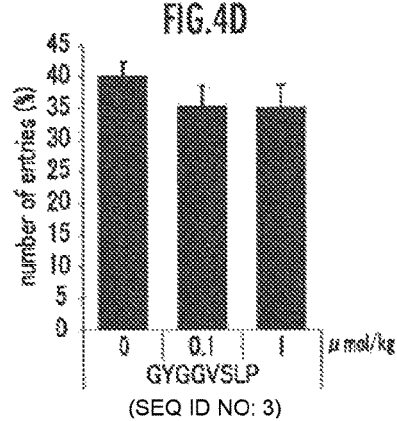
Figure 4E:
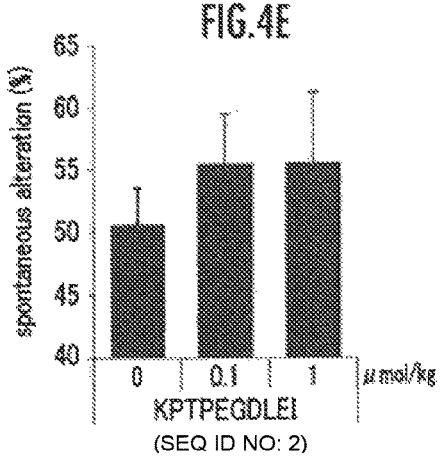
Figure 4F:
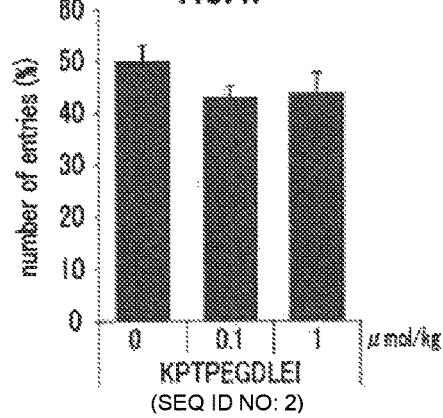

FIG. 3 illustrates HPLC profiles of a whey peptide extract digested with Protease P "Amino" 3SD or Thermoase C100. The figure also illustrates each amino acid sequences obtained by the N-terminal amino acid sequence analysis of each of the peaks.

Peptides are synthesized by solid-phase peptide synthesis based on the information of the obtained amino acid sequences to obtain synthetic peptides and the enhancing effect of the synthetic peptides on the memory and learning function and the cognitive function was examined.

[Examination of the Enhancing Effect of Synthetic Peptides on Memory and Learning Function and Cognitive Function]

Whey was treated with the proteolytic enzyme Protease P "Amano" 3SD derived from *Aspergillus melleus* and peptide sequences contained in the fractions having an enhancement activity of the memory and learning function and the cognitive function were analyzed. As a result, the sequence information of the 3 peptides GTWY (SEQ ID NO: 7), GYGGVSLP (SEQ ID: 3), and KPTPEGDLEI (SEQ ID NO: 2) were obtained (see the sequence list in Table 2).

Therefore, peptides were synthesized by solid-phase peptide synthesis based on the obtained amino acid sequence information. The synthetic peptides were then analyzed on whether the memory and learning function and the cognitive function are enhanced in the Y-maze test. The result is illustrated in FIG. 4A to FIG. 4F.

All the peptides GTWY (SEQ ID) NO: 7), GYGGVSLP (SEQ ID NO: 3), and KPTPEGDLEI (SEQ ID NO: 2) exhibited the activity of enhancing the memory and learning function and the cognitive function in a concentration-dependent manner. In particular, GTWY (SEQ ID NO: 7) is the major ingredient obtained by treating whey with Protease P "Amano" 3SD as illustrate in FIG. 3.

Whey was then treated with the proteolytic enzyme Thermoase C100 derived from *bacillus* and peptide sequences contained in the fractions having an activity of enhancing the memory arid learning function and the cognitive function were analyzed. As a result, the sequence information of the 4 peptides: TWY (SEQ ID NO: 11), TWYS (SEQ ID NO: 8), VAGTWYS (SEQ ID NO: 4), and VSLPEW (SEQ ID NO: 5) was obtained.

Synthetic peptides were obtained by solid-phase peptide synthesis based on the amino acid sequence information and analyzed by the Y-maze test on whether the memory and learning function and the cognitive function were enhanced by the synthetic peptides. The result was illustrated in FIG. 5A to FIG. 5H.

All of the 4 peptides: TWY (SEQ. ID NO: 11), TWYS (SEQ ID NO: 8), VAGTWYS (SEQ II) NO: 4), and VSLPEW (SEQ ID NO: 5) exhibited the activity of enhancing the memory and learning function and the cognitive function in a concentration-dependent manner. In particular, TWYS (SEQ ID NO: 8), TWY (SEQ NO: 11), and VSLPEW (SEQ ID NO: 5) are the major ingredients obtained by treating whey with Thermoase C100 as illustrated in FIG. 3.

[Effect of dipeptide WY (SEQ ID NO: 13) on memory and learning function and cognitive function]

The sequence tryptophan-tyrosine (WY) (SEQ ID NO: 13) was found to be contained in the 4 peptides VAGTWYS (SEQ ID NO: 4), GTWY (SEQ ID NO: 7), TWYS (SEQ ID NO: 8), and TWY (SEQ ID NO: 11) among the 7 peptides found to have the enhancing effect on the brain function from the aforementioned analyses. Since the effect on the memory and learning function and the cognitive function was observed with a variety of peptides containing the WY (SEQ ID NO: 13) sequence, the dipeptide WY (SEQ ID NO: 13) is considered to serve as a core sequence. In fact it is confirmed that the peptides of 8 amino acids containing WY (SEQ ID NO: 13) have the enhancing effect on the memory and learning function and the cognitive function. Therefore, peptides of 2 to 8 amino acids in length, comprising at least WY (SEQ ID NO: 13) as a core sequence, or peptides of up to about 12 residues containing the WY (SEQ ID NO: 13) sequence are considered to have an enhancing effect on the memory and learning function and the cognitive function in a view of the fact that the longest peptide that achieve an effect in the present invention is a peptide of 12 amino acids.

Since the dipeptide WY (SEQ ID NO: 13) is considered to be the core sequence, dipeptides containing tryptophan at the N terminus may be able to serve in enhancing the brain function. Therefore, dipeptides containing tryptophan at the N terminus were synthesized and examined in the Y-maze test on the effect on the brain function.

As a result, 4 dipeptides: tryptophan-tyrosine (WY, SEQ ID NO: 13), tryptophan-methionine (WM, SEQ ID NO: 14), tryptophan-leucine (WL, SEQ ID: NO 15), and tryptophan-valine (WV, SEQ ID NO: 16) contained in milk proteins as a sequence were found to have an enhancing effect on the memory and learning function and the cognition function in a concentration-dependent manner (FIG. 6A and FIG. 6B).

In contrast, the dipeptides: tyrosine-tryptophan (YW) and methionine-tryptophan (MW), which have the same amino acid compositions as, but a different sequence from SEQ ID NO: 13 and SEQ ID NO: 14, had no enhancing effect on the memory and learning function and the cognitive function. Moreover, tryptophan alone (W) had no effects.

Therefore, the dipeptides having tryptophan at the N terminus connected with a hydrophobic amino acid at the C terminus: WY (SEQ ID NO: 13), WM (SEQ ID NO: 14), WL (SEQ ID NO: 15), and WV (SEQ ID NO: 16) are considered to have the enhancing effect on the memory and learning function and the cognition function.

Like WY (SEQ ID NO: 13), other dipeptides WM (SEQ ID NO: 14), WL (SEQ ID NO: 15), and WV (SEQ ID NO: 16), which were confirmed to have the enhancing effect on the memory and learning function and the cognitive function with synthetic peptides, are also considered to serve as a core sequence as well as WY (SEQ ID NO: 13) and have an enhancing effect on the memory and learning function and the cognitive function. Therefore, it is considered that peptides containing the dipeptide in the sequence, having a length of 2 to 12 amino acids, and more typically 2 to 8 amino acids enhance the memory and learning function and the cognition function.

Searching for the dipeptide sequence in the proteins constituting whey using Genbank (www.ncbi.nlm.nih.gov/genbank) revealed the presence of the WY (SEQ ID NO: 13) sequence at a location in β-Lactoglobulin and 2 WL (SEQ ID NO: 15) sequences and 1 WV (SEQ ID NO: 16) sequence in α-Lactalbumin, which sequences were present in common in the proteins constituting whey derived from milks from cow, sheep, and goat.

[Contribution Ratio to Effect of Various Peptide in Whey Peptide Extract on Brain Function]

It was confirmed to what degree various peptides contribute to the effect in whey peptide extracts by the following wing methods.

Whey peptide extract was prepared by first adding 0.2% (w/v) enzymatic agent (Protease P "Amano" 3SD) to a 10% (w/v) whey proteins (Fonterra Co-operative Group Limited: WPC472) aqueous solution for digestion (50°, 5 hours) and deactivating the enzyme at 80° C. for 30 minutes. Concentrations of peptides contained in this whey peptide extract were quantified with a liquid chromatograph-tandem mass spectrometer (LC/NIS/MS) and the extract composition was reconstituted with synthetic peptides synthesized based on the information of the obtained concentrations. Specifically, peptides having each sequence set forth in Table 2 was prepared such that the concentrations of the synthetic peptides will be the same as those of the corresponding peptides in the whey peptide extract and mixed to prepare the reconstituted extract composition.

Whether the memory and learning function and the cognitive function are enhanced was analyzed by the Y-maze test in a way similar to the method described above, except that 10 mg/kg of this whey peptide extract was orally administered to mice (Extract section). Also for the reconstituted extract composition, whether the memory and learning function and the cognitive function are enhanced was similarly analyzed by the Y-maze, test (Reconstituted section).

TABLE 2

| Test section | Peptide sequence and concentration (nM) | | | | | | |
|---|---|---|---|---|---|---|---|
| | GTWY (SEQ ID NO: 7) | KPTPEGDLEI (SEQ ID NO: 2) | GYGGVSLP (SEQ ID NO: 3) | WY | WE | WV | WL |
| Extract | 0.62 | 0.11 | 0.3 | 0.19 | 0.05 | 0.08 | 0.14 |
| Reconstituted | 0.63 | 0.15 | 0.26 | 0.19 | 0.02 | 0.08 | 0.15 |

Figure 7A:
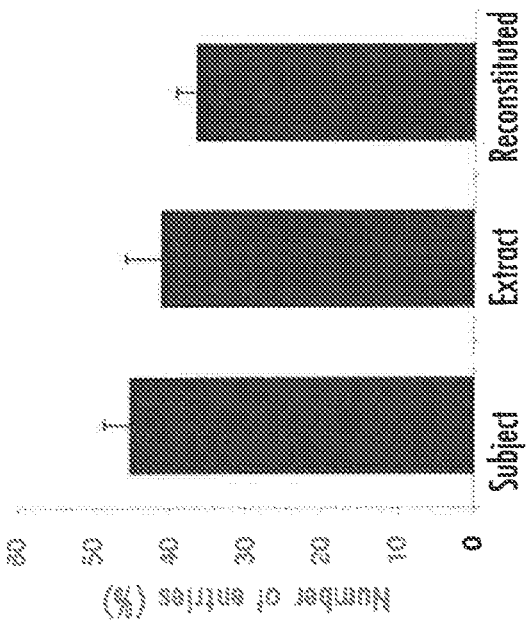
FIG. 7A and FIG. 7B illustrates enhancing effects of an whey peptide extract and a reconstituted sample on the memory and learning function and the cognitive function.
Figure 7B:
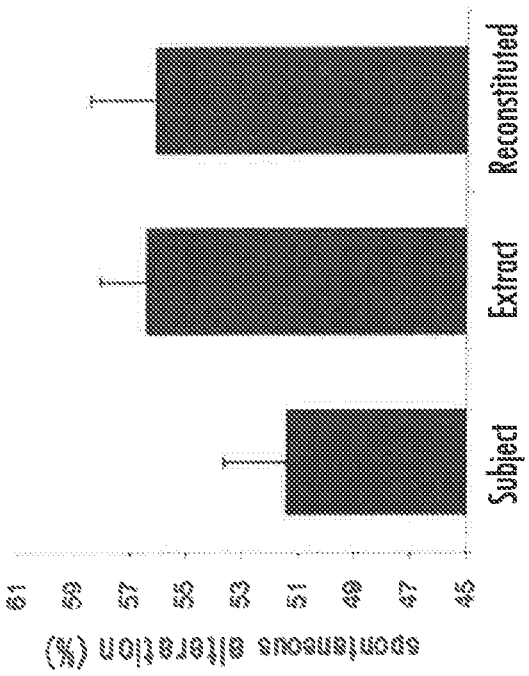
Figure 8A:
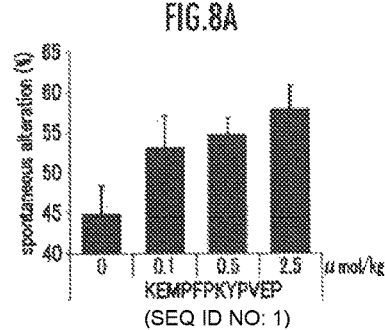
FIG. 8A to FIG. 8H illustrate enhancing effects of synthetic peptides of casein-derived peptides on the memory and learning function and the cognitive function.
Figure 8B:
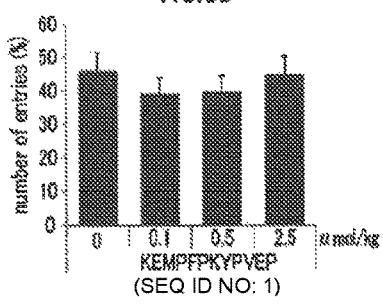
Figure 8C:
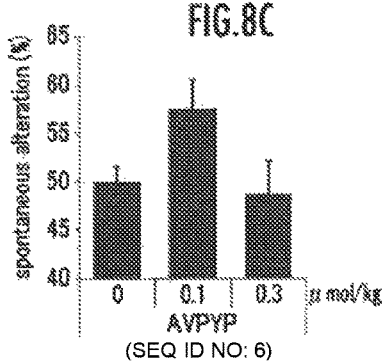
Figure 8D:
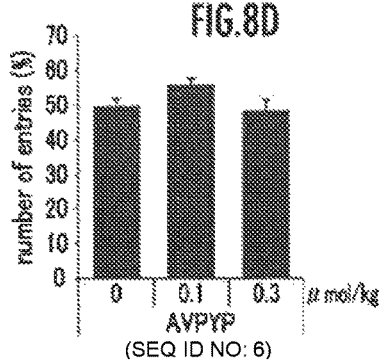
Figure 8E:
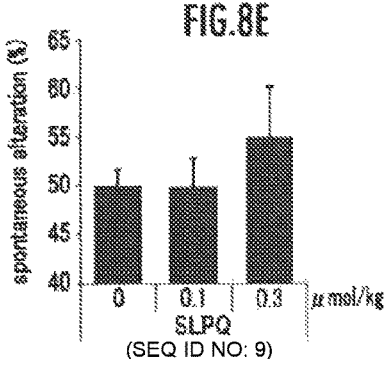
Figure 8F:
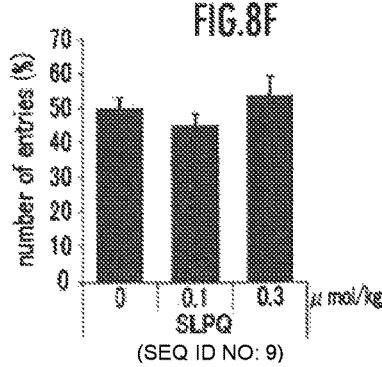
Figure 8G:
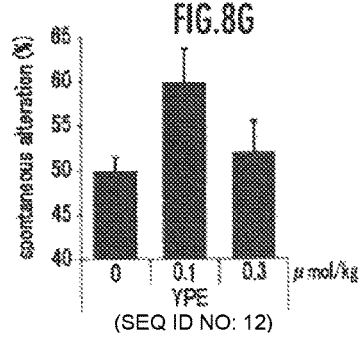
Figure 8H:
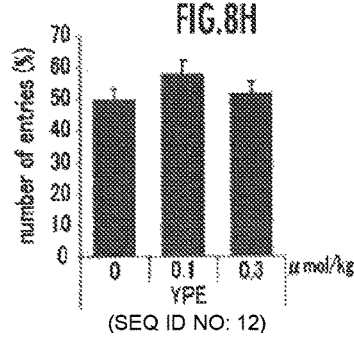

As a result, Reconstituted section exhibited the effect at a similar level to that of Extract section as illustrated in FIG. 7A and FIG. 7B, Therefore, these peptides were considered to be the main active ingredients in the whey peptide extract.

[Peptides With Enhancing Activity on Memory and Learning Function and Cognitive Function Contained in Casein Peptide Extract]

Casein is well known to be a protein contained in milk besides whey. Therefore casein (produced by Wako Pure Chemical Industries, Ltd.) was digested with Protease M "Amano" SD (which may be also abbreviated as Amano M), which is an enzymatic agent derived from a microbe belonging to the genus *Aspergillus* among one of the enzymatic agents set forth in Table 1 above, and analyzed for peptides having enhancing activity on the memory and learning function and the cognitive function. As conducted for whey, the peptide extract obtained by digesting casein with Amano M was fractionated by HPLC and the amino acid sequences of the active fractions were determined. As a result, information of the 6 sequences: KEMPFPKYPVEP (SEQ ID NO: 1), AVPYP (SEQ NO: 6), SLPQ (SEQ ID NO: 9), YPE (SEQ ID NO: 12), WY (SEQ ID NO: 13), and WM (SEQ ID NO: 14) were obtained as that of peptides with enhancement activity on the memory and learning function and the cognitive function.

In addition, the peptide extract obtained by treating casein with the enzyme Amano M, which is derived from a microbe belonging to the genus Aspergillus contained dipeptides WM (SEQ ID NO: 14) and WY (SEQ ID NO: 13), which are the same dipeptide having tryptophan at N terminus discussed above.

Therefore peptides were synthesized based on these sequence information and the memory and learning function and the cognitive function were evaluated by the Y-maze test using the synthetic peptides. The result is illustrated in FIG. 8A to FIG. 8H. It was demonstrated that all peptides have the enhancing effect on the memory and learning function and the cognitive function. The result of analysis of 2 dipeptides WY (SEQ ID NO: 13) and WM (SEQ ID NO: 14) has been already illustrated in FIG. 6A and FIG. 6B.

The peptide KEMPFPKYPVEP, set forth in SEQ ID NO: 1, obtained from the casein degradation product is a relatively long peptide of 12 amino acids in length. Therefore, the 3 peptides: EMPF (residues 2-5 of SEQ ID NO: 1), PK, and PVEP (SEQ ID NO: 10), sequences digested with trypsin and chymotrypsin, were synthesized and each administered to mice at an amount of 1 μmol/kg to conduct the Y-maze test.

Among the 3 peptides EMPF (residues 2-5 of SEQ ID NO: 1), PK, and PVEP (SEQ ID NO: 10), PVEP (SEQ ID NO: 10) had the enhancing effect on the memory and learning function at the similar level to that of the original amino acid sequence KEMPFPKYPVEP (SEQ ID NO: 1), as illustrate in FIG. 9A and FIG. 9B, Therefore PVEP (SEQ ID NO: 10) is the core sequence and peptides of about 12 residues having the amino acid sequence PVEP (SEQ ID NO: 10) are presumed to be equally effective. The foregoing peptides having the enhancing effect on the memory and learning function and the cognitive function are summarized in Table 3.

TABLE 3

| SEQ ID NO: | Amino acid sequence |
|---|---|
| #1 | KENIFTPKYPVEP |
| #2 | KPTPEGDLEI |
| #3 | GYGGVSLP |
| #4 | VAGTWYS |
| #5 | VSLPEW |
| #6 | AVPYP |
| #7 | GTWY |
| #8 | TWYS |
| #9 | SLPQ |
| #10 | PVEP |
| #11 | TWY |
| #12 | YPE |
| #13 | WY |

TABLE 3-continued

| SEQ ID NO: | Amino acid sequence |
|---|---|
| #14 | NW |
| #15 | WL |
| #16 | WV |

As described above, Sequence information (SEQ ID NOs: 1 to 16) of new peptides effective in enhancing the memory and learning function and/or the cognitive function was obtained from protein hydrolysates of whey and casein. The effect was also confirmed with synthetic peptides.

[Method of Screening for Peptides That Enhance Phagocytotic Activity, and Anti-Inflammatory Activity of Microglia]

Casein peptides that enhance phagocytotic activity and anti-inflammatory activity of microglia were isolated and identified by the following procedure.

{{Method of Isolating Peptide}}

Sodium Casein (produced by Wako Pure Chemical Industries Corporation) was treated with food additive protease or peptidase. Protease agent used were Newlase F3, Protease M "Amano" SD, Protease A "Amano" SD, Protease P "Amano" 3SD, Protin SD-NY10, Thermoase PC10F, Protin SD-AY10, Papain W-40, and Bromelain F, and the peptidase agents used were ProteAX and Peptidase R (Amano Enzyme Inc.).

The enzymatic reaction solutions obtained by treating sodium casein with the enzymes mentioned above were applied to a C18 solid-phase extraction column. Elution was conducted stepwise with 20, 40, 60, and 80% methanol aqueous solutions and the obtained fractions were concentrated and applied to preparative HPLC. The separation column used was a C18 column (10 mm in inner diameter, 250 mm in length, 5 μp in particle size) and elution was conducted with a gradient of 0% of Solution B (methanol) at 0 min. and 80% of Solution B at 40 min. in Solution A (5% methanol) at a speed of 5 ml/min as the mobile phase. The eluate was fractionated into plural fractions, each of which was concentrated and dried. Each fraction was redissolved in a solution containing a little methanol and then applied to analytical HPLC for subfractionation. The separation column used was a C18 column (4.6 mm in inner diameter, 250 mm in length, and 5 μm in particle size) and elution was conducted using a gradient of 5% Solution B (0.1% TFA/acetonitrile) at 0 min., 20% Solution B at 30 min., and 20% Solution B at 40 min. or 5% Solution B at 0 min. and 80% Solution B at 30 min in Solution A (0.1% TEA) at a speed of 1 ml/min, as the mobile phase. The detection was conducted at UV 220 nm. The plural peaks obtained in the analysis were collected by re-fractionation. Each of the obtained fractions was concentrated and dried to remove TFA and redissolved in a solution containing a little methanol.

These samples were evaluated in the evaluation system using the phagocytotic activity and the anti-inflammatory activity of microglia as indexes to obtain enzymatic treatment product having high activity. The methods of isolating microglia and evaluating the phagocytotic activity and the anti-inflammatory activity are as follows.

{{Isolation of Microglia}}

Brain tissue homogenate is obtained by treating the brain extirpated from a mouse with papain. After stopping the enzymatic reaction, microglia were allowed to interact with a pan-microglia marker, CD11b antibody (produced from Miltenyi Biotec) magnetically-labeled with microbeads and isolated by the MACS method.

{{Evaluation of Phagocytotic Activity}}

Isolated microglia are cultured for 12 hours in a medium supplemented with various peptides. Amyloid β1-42 (produced by AnaSpec) labeled with the fluorescent dye fluorescein (FAM) was then added to the medium at a concentration of 500 nM. The supernatant was removed after 5 hours of culturing, extracellular fluorescence was quenched with trypan blue, and the amount of amyloid β taken up into microglia was measured with a microplate reader as the amount of fluorescence to evaluate the enhancement of the phagocytotic activity.

{{Evaluation of Anti-Inflammatory Activity}}

Isolated microglia are cultured for 12 hours in a medium supplemented with various peptides. 5 ng/ml lipopolysaccharide (LPS, SIGMA-ALDRICH) and 0.5 ng/ml interferon γ(IFNγ, R & D systems) were then added and culture was continued for 12 hours. TNF-α contained in the culture supernatant was quantified with an ELISA kit (eBiosceince).

[Isolation and Identification of Peptides That Enhance Activity of Microglia,]

7 peptides having the enhancement effect on the phagocytotic activity and the anti-inflammatory activity of microglia were obtained by the method described above. All the purified peptides were analyzed by the N-terminal amino acid sequence analysis to obtain amino acid sequences. The obtained amino acid sequences of the peptides are listed in Table 4 in 1 character notation.

TABLE 4

Figure 10:
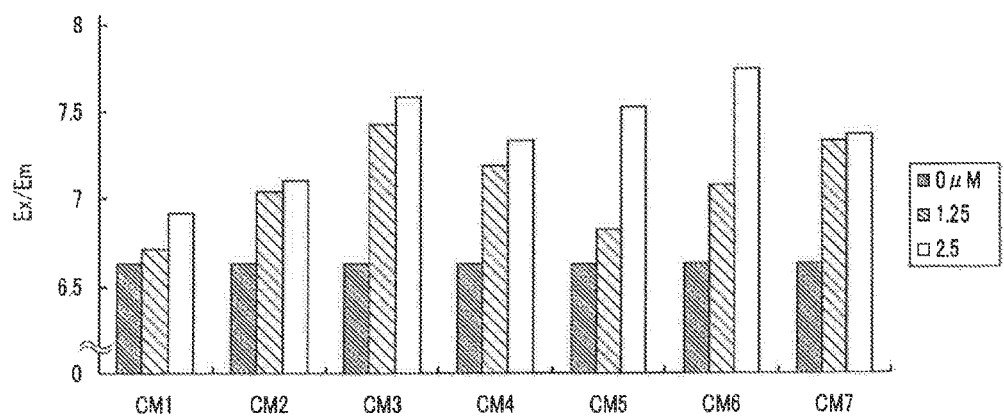
FIG. 10 illustrates effects of peptides on the phagocytosis of microglia.

| SEQ ID NO: | Amino acid sequence | Designation in FIGs. 9 & 10 |
|---|---|---|
| #1 | KEMPFPKYPVEP | CM1 |
| #17 | SMKEGIHAQQ | CM2 |
| #6 | AVPYP | CM3 |
| #9 | SLPQ | CM4 |
| #12 | YPE | CM5 |
| #14 | WM | CM6 |
| #13 | WY | CM7 |

[Amyloid β-Phagocytosis Activity of Microglia With Synthetic Peptides]

Peptides were synthesized based on the obtained amino acid sequences and the phagocytotic activity of microglia was evaluated.

The isolated microglia are pretreated in a medium supplemented with 0, 1.25, or 2.5 μM of a synthetic peptide (KEMPFPKYPVEP (SEQ ID NO: 1), SMKEGIHAQQ (SEQ ID NO: 17), AVPYP (SEQ ID NO: 6), SLPQ (SEQ ID NO: 9), YPE (SEQ ID NO: 12), WM (SEQ ID NO: 14), or WY (SEQ ID NO: 13)) for 12 hours.

After a pretreatment as described above, FAM-labeled amyloid β1-42 was added to the medium and the cells were allowed to take it up. The amount of amyloid β taken up was measured as the amount of fluorescence to evaluate enhancement of the phagocytotic activity. The result of measurement of amyloid β-phagocytosis by microglia is illustrated in FIG. 10. In FIG. 10, "CM1" indicates the result of KEMPFPKYPVEP (SEQ ID NO: 1), "CM2" indicates the result of SMKEGIHAQQ (SEQ NO: 17), "CM3" indicates the result of AVPYP (SEQ ID NO: 6), "CM4" indicates the result of SLPQ (SEQ ID NO: 9), "CMS" indicates the result of YPE (SEQ ID NO: 12), "CM6" indicates the result of WM (SEQ ID NO: 14), and "CM7" indicates the result of WY (SEQ ID NO: 13).

It is demonstrated that any of the peptides enhances the phagocytotic activity of microglia in a concentration-dependent manner from 1.25 μM, as seen front FIG. 10.

[Anti-Inflammatory Activity With Synthetic Peptides]

Figure 11:
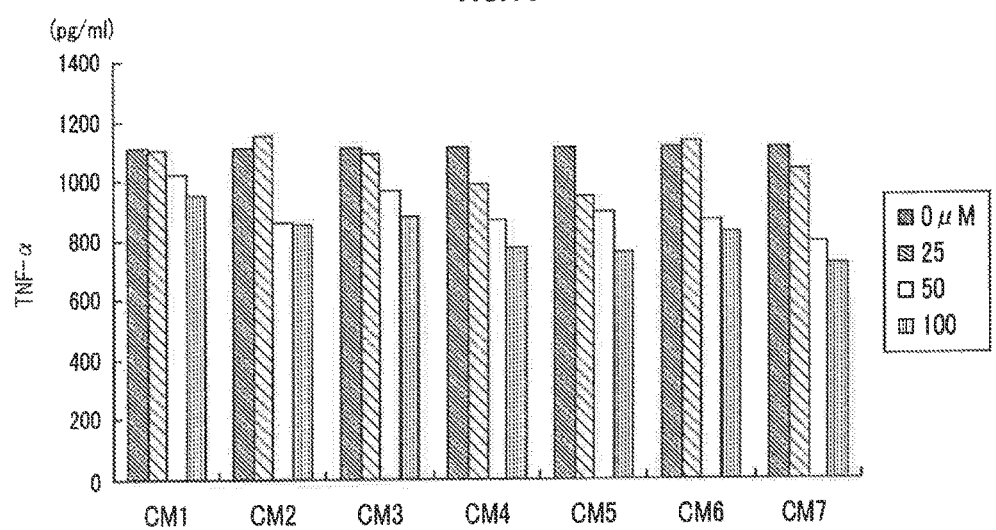
FIG. 11 illustrates effects of peptides on the anti-inflammatory function of microglia.

Peptides were synthesized based on the obtained amino acid sequences and the anti-inflammatory effect was evaluated. The isolated microglia are pretreated in a medium supplemented with 0, 25, 50, or 100 μM of a synthetic peptide (KEMPFPKYPVEP (SEQ ID NO: 1), SMKEGIHAQQ (SEQ ID NO: 17), AVPYP (SEQ ID NO: 6), SLPQ (SEQ ID NO: 9), YPE (SEQ ID NO: 12), WM (SEQ ID NO: 14), or WY (SEQ In NO: 13)) for 12 hours. As described above, LPS and IFN-γ were added to the medium and culture was continued for 12 hours. INF-α contained in the culture supernatant was measured by ELISA. The result is illustrated in FIG. 11. In FIG. 11, "CM1" indicates the result of KEMPFPKYPVEP (SEQ ID NO: 1), "CM2" indicates the result of SMKEGIHAQQ (SEQ ID NO: 17), "CM3" indicates the result of AVPYP (SEQ ID NO: 6), "CM4" indicates the result of SLPQ (SEQ ID NO: 9), "CMS" indicates the result of YPE (SEQ ID NO: 12), "CM6" indicates the result of WM (SEQ ID NO: 14), and "CM7" indicates the result of WY (SEQ ID NO: 13).

As illustrate in FIG. 11, any of the peptides was confirmed to suppress the production of TNF-α, which is an inflammatory cytokine, in a concentration-dependent manner from 25 μM, the enhancement of the anti-inflammatory effect was observed, and the peptide WY of SEQ ID NO: 13 ("CM7" in FIG. 11) was demonstrated to have a particularly high anti-inflammatory effect.

As described above, sequence information (SEQ ID NOs: 1, 6, 9, 12, 13, 14, 17) of new peptides effective in enhancing the phagocytotic activity and/or anti-inflammatory activity of microglia was obtained from protein hydrolysates of whey and casein. The effect was also confirmed with synthetic peptides.

In the tests described above, the enhancement of the phagocytotic activity of microglia against amyloid β, of which accumulation in the brain is considered to be a cause of Alzheimer's disease, was demonstrated. However, substances that are phagocytosed by microglia are not limited to amyloid β. Therefore, amelioration of the cognitive function has been considered to be possible by promoting generation of synapses by removing old synapses or dead cells.

The suppression of the production of TNF-α by microglia was also demonstrated as the response to the LPS stimulation. However, the inflammatory signals are not limited to LPS. Therefore alleviation of various inflammatory states caused by endogenous inflammatory factors and exogenous pathogenic factors has been considered to be possible.

When waste materials such as amyloid β deposit in brain with aging, an inflammatory state is induced in the brain by microglia. Since reactive oxygen species and inflammatory cytokines produced by inflammation are stress factors for neuronal cells, inflammatory states in the brain are known to be generally associated with the decline of the cognitive function (Non Patent Literature 16). Moreover, inflammatory states in neural tissue are, not only related to dementia, but also closely related to depression, pain, and chronic fatigue.

As described above, the peptides according to the present invention enhance the phagocytotic activity of microglia and also comprise the anti-inflammatory effect. Therefore, the peptides are expected to contribute to the maintenance, improvement, and amelioration of the cognitive function by removing waste materials in the brain without inducing inflammation through microglia in the brain.

[Presence of Peptide Sequences According to the Present Invention in Amino Acid Sequences of Proteins Contained in Various Foods or Food Materials]

Whether the peptide sequences of SEQ ID NOs: 12 to 16 are present in amino acid sequences of proteins contained in foods or food materials were examined. Specifically, whether the sequences of such peptides are present in the amino acid sequences of the 34 proteins listed in Table 5 below was examined.

TABLE 5

| Origin | Protein | | SEQ ID NO: |
|---|---|---|---|
| Milk | Casein | α-S-1 Casein 214 aa protein | 18 |
| | | β-Casein 224 aa protein | 19 |
| | | κ-Casein 190 aa protein | 20 |
| | | γ-Casein→degradation product of β-Casein | — |
| | | proteose peptone→degradation product of β-Casein | — |
| | Whey | β-Lactoglobulin 178 aa protein | 21 |
| | | α-Lactalbumin 142 aa protein | 22 |
| | | LP: Lactoperoxidase 712 aa protein | 23 |
| | | LF: Lactoferrin 708 aa protein | 24 |
| | | Immunoglobulin H chain only partial sequence (Ig: Immunoglobulin) 164 aa protein | 25 |
| | | Immunoglobulin L chain only partial sequence (Ig: Immunoglobulin) 101 aa protein | 26 |
| | BSA | BOVIN Serum albumin 607 aa protein | 27 |
| Soybean | Glycinin | SOYBN Glycinin 563 aa protein | 28 |
| | β-Conglycinin | Beta-conglycinin, alpha' chain 639 aa protein | 29 |
| | | SOYBN Beta-conglycinin alpha-subunit 623 aa protein | 30 |
| | | SOYBN Beta-conglycinin, beta chain 439 aa protein | 31 |
| Wheat | Gliadin | WHEAT Alpha-gliadin (Fragment) 288 aa protein | 32 |
| | | WHEAT Gamma-gliadin 302 aa protein | 33 |
| | | WHEAT Alpha/beta-gliadin 331 aa protein | 34 |
| | | WHEAT Omega-5 gliadin 439 aa protein | 35 |
| | Glutenin | WHEAT High-molecular-weight glutenin subunit 2.6 OS 1025 aa protein | 36 |
| | | WHEAT Low molecular weight glutenin subunit OS 392 aa protein | 37 |
| Egg Yolk | Lipovitellin | Vitellogenin-1 (Minor vitellogenin) (Vitellogenin I) 1,912 aa protein | 38 |
| | | Vitellogenin-2 (Major vitellogenin) 1850 aa protein | 39 |
| Egg White | Ovalbumin | Ovalbumin (Allergen Gal d II) (Egg albumin) 386 aa protein | 40 |
| | Ovotransferrin | Ovotransferrin (*Gallus gallus*, Chicken) 738 aa protein | 41 |
| | Ovomucoid | Ovomucoid (Allergen Gal d I) (allergen Gal d 1) 210 aa protein | 42 |
| | Ovomucin | Mucin-5B (Ovomucin, alpha-subunit) 2108 aa protein | 43 |
| | Ovomucin | Mucin-6 (Ovomucin, beta-subunit) *Gallus gallus* (Chicken) 1185 aa protein | 44 |
| | Lysozyme | Lysozyme g *Gallus gallus* (Chicken) 211 aa protein | 45 |
| | | Lysozyme C 147 aa protein | 46 |

TABLE 5-continued

| Origin | Protein | SEQ ID NO: |
|---|---|---|
| Chicken | Collagen | Collagen alpha-1(I) chain (Alpha-1 type I collagen) chicken 1453 aa protein | 47 |
| | | CHICK Collagen alpha-1(II) chain (Fragment) 369 aa protein | 48 |
| | | CHICK Collagen alpha-2(I) chain (Fragments) 1362 aa protein | 49 |

The result of the examination whether the peptide sequences according to the present invention are present in the amino acid sequence of the proteins contained in various foods or food materials is illustrated in Tables 6 to 8. γ-Casein and proteose peptone are degradation products of β-Casein. Therefore, the dipeptides that have been confirmed to be present in β-Casein are considered to be possibly present in γ-Casein and proteose peptone.

TABLE 6

Milk

| | | | Csein | | | | Whey | | | | | |
|---|---|---|---|---|---|---|---|---|---|---|---|---|
| SEQ ID NO: | Peptide | Origin Protein Name | α-S-1 Casein 214 aa protein | β- Casein 224 aa protein | κ- Casein 190 aa protein | γ-Casein→ degradation product of β-Casein | proteose peptone→ degradation product of β-Casein | β-Lacto-globulin 178 aa protein | α-Lact-albumin 142 aa protein | LP: Lacto-peroxidase 712 aa protein | LF: Lacto-ferrin 708 aa protein | partial sequence (Ig: Immuno-globulin) H chain only 164 aa protein | partial sequence (Ig: Immuno-globulin) L chain only 101 aa protien | BSA BOVIN Serum albumin 607 aa protein |
| 12 | YPE | | ○ | — | — | | | — | — | — | — | — | — | — |
| 13 | WY | | ○ | — | — | | | ○ | — | — | — | — | ○ | — |
| 14 | WM | | — | ○ | — | | | — | — | — | — | — | — | — |
| 15 | WL | | — | — | — | | | — | ○ | ○ | — | — | — | — |
| 16 | WV | | — | — | — | | | — | ○ | ○ | ○ | ○ | — | ○ |

TABLE 7

| | | | Soybean | | | | Wheat | | | | | |
|---|---|---|---|---|---|---|---|---|---|---|---|---|
| | | | | β-Conglycinin | | | Gliadin | | | | Gluteinin | |
| | | | | | | | | | | | WHEAT High-molecular-weight glutenin subunit 2.6 OS 1025 aa protein | WHEAT Low molecular weight glutenin subunit OS 392 aa protein |
| SEQ ID NO: | Peptide | Origin Protein Name | Glycinin SOYBN Glycinin 563 aa protein | SOYBN Beta-conglycinin, alpha' chain 639 aa protein | SOYBN Beta-conglycinin, alpha subunit 623 aa protein | Beta-conglycinin, beta chain 439 aa protein | WHEAT Alpha-gliadin (Fragment) 288 aa protein | WHEAT Gamma-gliadin 302 aa protein | WHEAT Alpha/beta-gliadin 331 aa protein | WHEAT Omega-5 gliadin 439 aa protein | | |
| 12 | YPE | | ○ | — | — | — | — | — | — | — | — | — |
| 13 | WY | | — | — | — | — | — | — | — | — | ○ | — |
| 14 | WM | | — | — | — | — | — | — | — | — | — | — |
| 15 | WL | | — | — | — | — | — | — | — | — | ○ | — |
| 16 | WV | | — | — | — | — | — | — | — | — | — | — |

TABLE 8

| SEQ ID NO: | Peptide | Origin Protein Name | Egg Yolk Lipovitellin | | Egg White | | |
|---|---|---|---|---|---|---|---|
| | | | | | Ovalbumin Ovalbumin | Ovotransferrin Ovotransferrin | Ovomucoid Ovomucoid |
| | | | Vitellogenin-1 (Minor vitellogenin) (Vitellogenin I) 1,912 aa protein | Vitellogenin-2 (Major vitellogenin) 1850 aa protein | (Allergen Gal d II) (Egg albumin) 386 aa protein | (Gallus gallus, Chicken) 738 aa protein | (Allergen Gal d 1) 210 aa protein |
| 12 | YPE | | — | — | — | — | — |
| 13 | WY | | ○ | — | — | — | — |
| 14 | WM | | ○ | ○ | — | — | — |
| 15 | WL | | — | ○ | — | ○ | — |
| 16 | WV | | ○ | — | ○ | — | — |

| SEQ ID NO: | Egg White | | | | Chicken Collagen | | |
|---|---|---|---|---|---|---|---|
| | Ovopmucin | Ovomusin Mucin-6 (Ovomucin, beta-subunit) | Lysozume | | Collagen alpha-1(I) chain | CHICK Collagen | CHICK Collagen |
| | Mucin-5B (Ovomucin, alpha-subunit) 2108 aa protein | Gallus gallus (Chicken) 1185 aa protein | Lysozyme g Gallus gallus (Chicken) 211 aa protein | Lysozyme C 147 aa protein | (Alpha-1 type I collagen) chicken 1453 aa protein | alpha-1(II) chain (Fragment) 369 aa protein | alpha-2(I) chain (Fragments) 1362 aa protein |
| 12 | ○ | — | — | — | ○ | — | — |
| 13 | — | — | — | — | ○ | — | ○ |
| 14 | — | — | — | — | — | — | — |
| 15 | — | — | — | — | — | — | — |
| 16 | — | — | — | ○ | — | — | — |

As a result, at least 1 sequence of the peptide sequences of SEQ ID NOs: 12. to 16 was found to be contained in at least 1 protein among proteins contained in the 6 foods and it was confirmed that such a peptide is produced by processing such a protein or a food or food material containing the protein by acid hydrolysis, enzymatic treatment with protease, microbe fermentation, or the like.

[Production of Drinks Containing Composition of the Present Invention]

A coffee drink and a fruit juice drink were produced using a whey peptide extract prepared as described above. Compositions and production processes of the drinks were illustrated in Table 9 and Table 10, respectively.

TABLE 9

| Coffee drinks | Per 100 g |
|---|---|
| Whey peptide extract | 100 mg |
| Coffee extract (extracted from 100 g of moderately ground coffee bean with 1 L of hot water at 95° C.) | 80 mL |

TABLE 9-continued

| Coffee drinks | Per 100 g |
|---|---|
| Sugar | 10 g |
| Sodium hydrogen, carbonate | 100 mg |
| Ion exchanged water | quant. suff. |
| Dispense into 250 ml steel cans, fill with nitrogen, and then sterilize for 10 min. at 121° C. | |

TABLE 10

| Fruit juice drinks | Per 100 g |
|---|---|
| Whey peptide extract | 100 mg |
| 5 times concentrated orange juice | 20 g |
| Ion exchanged water | quant. suff. |
| Dispense into containers and sterilize for 10 min. at 65° C. | |

The invention claimed is:

1. A method of enhancing memory and learning function or cognitive function, or enhancing memory and learning function and cognitive function, comprising administering a composition comprising a peptide that comprises the amino acid sequence of SEQ ID NO: 13, or a pharmaceutically acceptable salt or solvate thereof, to a subject in need such enhancement.

2. The method according to claim 1, wherein said peptide comprises an amino acid sequence selected from the group consisting of SEQ ID NOs: 4, 7, 8 and 11.

3. The method according to claim 1, wherein the composition is in the form of a food.

4. The method according to claim 1, wherein the composition is in the form of a medicament.

5. The method according to claim 1, wherein the peptide is produced by hydrolysis of a protein contained in a food or food material.

6. The method according to claim 1, wherein the peptide is obtained by an enzymatic treatment of a milk protein, or of a food or food material containing the milk protein, with an enzymatic agent from a microorganism.

7. The method according to claim 6, wherein the milk protein or the food or food material containing the milk protein is whey or casein.

8. The method according to claim 6, wherein the enzymatic agent comprises at least one enzyme from a microbe, wherein said at least one enzyme is from a microbe of a genus selected from the group consisting of *Aspergillus*, *Bacillus* and *Rhizopus*.

9. A method of enhancing microglial phagocytotic activity or anti-inflammatory activity, or enhancing microglial phagocytotic activity and anti-inflammatory activity, comprising administering a composition comprising a peptide that comprises the amino acid sequence of SEQ ID NO: 13, or a pharmaceutically acceptable salt or solvate thereof, to a subject in need such enhancement.

10. The method according to claim 9, wherein said peptide consists of the amino acid sequence of SEQ ID NO: 13.

11. The method according to claim 1, wherein said peptide consists of an amino acid sequence selected from the group consisting of SEQ ID NOs: 4, 7, 8, 11 and 13.

12. The method according to claim 9, wherein the composition is in the form of a food.

13. The method according to claim 9, wherein the composition is in the form of a medicament.

14. The method according to claim 9, wherein the peptide is produced by hydrolysis of a protein contained in a food or food material.

15. The method according to claim 9, wherein the peptide is obtained by an enzymatic treatment of a milk protein, or a food or food material containing the milk protein, with an enzymatic agent from a microorganism.

16. The method according to claim 15, wherein the milk protein or the food or food material containing the milk protein is whey or casein.

17. The method according to claim 15, wherein the enzymatic agent comprises at least one enzyme from a microbe, wherein said at least one enzyme is from a microbe of a genus selected from the group consisting of *Aspergillus, Bacillus* and *Rhizopus*.

* * * * *

SEQUENCE LISTING

<160> NUMBER OF SEQ ID NOS: 49

<210> SEQ ID NO 1
<211> LENGTH: 12
<212> TYPE: PRT
<213> ORGANISM: Bos taurus

<400> SEQUENCE: 1

```
Lys Glu Met Pro Phe Pro Lys Tyr Pro Val Glu Pro
1               5                   10

<210> SEQ ID NO 2
<211> LENGTH: 10
<212> TYPE: PRT
<213> ORGANISM: Bos taurus

<400> SEQUENCE: 2

Lys Pro Thr Pro Glu Gly Asp Leu Glu Ile
1               5                   10

<210> SEQ ID NO 3
<211> LENGTH: 8
<212> TYPE: PRT
<213> ORGANISM: Bos taurus

<400> SEQUENCE: 3

Gly Tyr Gly Gly Val Ser Leu Pro
1               5

<210> SEQ ID NO 4
<211> LENGTH: 7
<212> TYPE: PRT
<213> ORGANISM: Bos taurus

<400> SEQUENCE: 4

Val Ala Gly Thr Trp Tyr Ser
1               5

<210> SEQ ID NO 5
<211> LENGTH: 6
<212> TYPE: PRT
<213> ORGANISM: Bos taurus

<400> SEQUENCE: 5

Val Ser Leu Pro Glu Trp
1               5

<210> SEQ ID NO 6
<211> LENGTH: 5
<212> TYPE: PRT
<213> ORGANISM: Bos taurus

<400> SEQUENCE: 6

Ala Val Pro Tyr Pro
1               5

<210> SEQ ID NO 7
<211> LENGTH: 4
<212> TYPE: PRT
<213> ORGANISM: Bos taurus

<400> SEQUENCE: 7

Gly Thr Trp Tyr
1

<210> SEQ ID NO 8
<211> LENGTH: 4
<212> TYPE: PRT
<213> ORGANISM: Bos taurus

<400> SEQUENCE: 8

Thr Trp Tyr Ser
```

```
<210> SEQ ID NO 9
<211> LENGTH: 4
<212> TYPE: PRT
<213> ORGANISM: Bos taurus

<400> SEQUENCE: 9

Ser Leu Pro Gln
1

<210> SEQ ID NO 10
<211> LENGTH: 4
<212> TYPE: PRT
<213> ORGANISM: Bos taurus

<400> SEQUENCE: 10

Pro Val Glu Pro
1

<210> SEQ ID NO 11
<211> LENGTH: 3
<212> TYPE: PRT
<213> ORGANISM: Bos taurus

<400> SEQUENCE: 11

Thr Trp Tyr
1

<210> SEQ ID NO 12
<211> LENGTH: 3
<212> TYPE: PRT
<213> ORGANISM: Bos taurus

<400> SEQUENCE: 12

Tyr Pro Glu
1

<210> SEQ ID NO 13
<211> LENGTH: 2
<212> TYPE: PRT
<213> ORGANISM: Bos taurus

<400> SEQUENCE: 13

Trp Tyr
1

<210> SEQ ID NO 14
<211> LENGTH: 2
<212> TYPE: PRT
<213> ORGANISM: Bos taurus

<400> SEQUENCE: 14

Trp Met
1

<210> SEQ ID NO 15
<211> LENGTH: 2
<212> TYPE: PRT
<213> ORGANISM: Bos taurus

<400> SEQUENCE: 15

Trp Leu
1
```

<210> SEQ ID NO 16
<211> LENGTH: 2
<212> TYPE: PRT
<213> ORGANISM: Bos taurus

<400> SEQUENCE: 16

Trp Val
1

<210> SEQ ID NO 17
<211> LENGTH: 10
<212> TYPE: PRT
<213> ORGANISM: Bos taurus

<400> SEQUENCE: 17

Ser Met Lys Glu Gly Ile His Ala Gln Gln
1               5                   10

<210> SEQ ID NO 18
<211> LENGTH: 214
<212> TYPE: PRT
<213> ORGANISM: Bos taurus

<400> SEQUENCE: 18

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
                20                  25                  30

Glu Asn Leu Leu Arg Phe Phe Val Ala Pro Phe Pro Glu Val Phe Gly
            35                  40                  45

Lys Glu Lys Val Asn Glu Leu Ser Lys Asp Ile Gly Ser Glu Ser Thr
    50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
        115                 120                 125

Asn Ser Ala Glu Glu Arg Leu His Ser Met Lys Glu Gly Ile His Ala
130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Thr Asp Ala Pro
            180                 185                 190

Ser Phe Ser Asp Ile Pro Asn Pro Ile Gly Ser Glu Asn Ser Glu Lys
        195                 200                 205

Thr Thr Met Pro Leu Trp
    210

<210> SEQ ID NO 19
<211> LENGTH: 224
<212> TYPE: PRT
<213> ORGANISM: Bos taurus

<400> SEQUENCE: 19

```
Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Thr Glu Asp Glu Leu Gln Asp Lys Ile
50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn Ile Pro Pro Leu Thr Gln Thr Pro
                85                  90                  95

Val Val Val Pro Pro Phe Leu Gln Pro Glu Val Met Gly Val Ser Lys
            100                 105                 110

Val Lys Glu Ala Met Ala Pro Lys His Lys Glu Met Pro Phe Pro Lys
        115                 120                 125

Tyr Pro Val Glu Pro Phe Thr Glu Ser Gln Ser Leu Thr Leu Thr Asp
            130                 135                 140

Val Glu Asn Leu His Leu Pro Leu Pro Leu Leu Gln Ser Trp Met His
145                 150                 155                 160

Gln Pro His Gln Pro Leu Pro Pro Thr Val Met Phe Pro Pro Gln Ser
                165                 170                 175

Val Leu Ser Leu Ser Gln Ser Lys Val Leu Pro Val Pro Gln Lys Ala
            180                 185                 190

Val Pro Tyr Pro Gln Arg Asp Met Pro Ile Gln Ala Phe Leu Leu Tyr
            195                 200                 205

Gln Glu Pro Val Leu Gly Pro Val Arg Gly Pro Phe Pro Ile Ile Val
210                 215                 220

<210> SEQ ID NO 20
<211> LENGTH: 190
<212> TYPE: PRT
<213> ORGANISM: Bos taurus

<400> SEQUENCE: 20

Met Met Lys Ser Phe Phe Leu Val Val Thr Ile Leu Ala Leu Thr Leu
1               5                   10                  15

Pro Phe Leu Gly Ala Gln Glu Gln Asn Gln Glu Gln Pro Ile Arg Cys
            20                  25                  30

Glu Lys Asp Glu Arg Phe Phe Ser Asp Lys Ile Ala Lys Tyr Ile Pro
        35                  40                  45

Ile Gln Tyr Val Leu Ser Arg Tyr Pro Ser Tyr Gly Leu Asn Tyr Tyr
50                  55                  60

Gln Gln Lys Pro Val Ala Leu Ile Asn Asn Gln Phe Leu Pro Tyr Pro
65                  70                  75                  80

Tyr Tyr Ala Lys Pro Ala Ala Val Arg Ser Pro Ala Gln Ile Leu Gln
                85                  90                  95

Trp Gln Val Leu Ser Asn Thr Val Pro Ala Lys Ser Cys Gln Ala Gln
            100                 105                 110

Pro Thr Thr Met Ala Arg His Pro His Pro His Leu Ser Phe Met Ala
            115                 120                 125

Ile Pro Pro Lys Lys Asn Gln Asp Lys Thr Glu Ile Pro Thr Ile Asn
130                 135                 140

Thr Ile Ala Ser Gly Glu Pro Thr Ser Thr Pro Thr Thr Glu Ala Val
```

```
                    145                 150                 155                 160
Glu Ser Thr Val Ala Thr Leu Glu Asp Ser Pro Glu Val Ile Glu Ser
                165                 170                 175
Pro Pro Glu Ile Asn Thr Val Gln Val Thr Ser Thr Ala Val
            180                 185                 190

<210> SEQ ID NO 21
<211> LENGTH: 178
<212> TYPE: PRT
<213> ORGANISM: Bos taurus

<400> SEQUENCE: 21

Met Lys Cys Leu Leu Leu Ala Leu Ala Leu Thr Cys Gly Ala Gln Ala
1               5                   10                  15
Leu Ile Val Thr Gln Thr Met Lys Gly Leu Asp Ile Gln Lys Val Ala
            20                  25                  30
Gly Thr Trp Tyr Ser Leu Ala Met Ala Ala Ser Asp Ile Ser Leu Leu
        35                  40                  45
Asp Ala Gln Ser Ala Pro Leu Arg Val Tyr Val Glu Glu Leu Lys Pro
    50                  55                  60
Thr Pro Glu Gly Asp Leu Glu Ile Leu Leu Gln Lys Trp Glu Asn Gly
65                  70                  75                  80
Glu Cys Ala Gln Lys Lys Ile Ile Ala Glu Lys Thr Lys Ile Pro Ala
                85                  90                  95
Val Phe Lys Ile Asp Ala Leu Asn Glu Asn Lys Val Leu Val Leu Asp
            100                 105                 110
Thr Asp Tyr Lys Lys Tyr Leu Leu Phe Cys Met Glu Asn Ser Ala Glu
        115                 120                 125
Pro Glu Gln Ser Leu Ala Cys Gln Cys Leu Val Arg Thr Pro Glu Val
    130                 135                 140
Asp Asp Glu Ala Leu Glu Lys Phe Asp Lys Ala Leu Lys Ala Leu Pro
145                 150                 155                 160
Met His Ile Arg Leu Ser Phe Asn Pro Thr Gln Leu Glu Glu Gln Cys
                165                 170                 175
His Ile

<210> SEQ ID NO 22
<211> LENGTH: 142
<212> TYPE: PRT
<213> ORGANISM: Bos taurus

<400> SEQUENCE: 22

Met Met Ser Phe Val Ser Leu Leu Leu Val Gly Ile Leu Phe His Ala
1               5                   10                  15
Thr Gln Ala Glu Gln Leu Thr Lys Cys Glu Val Phe Arg Glu Leu Lys
            20                  25                  30
Asp Leu Lys Gly Tyr Gly Gly Val Ser Leu Pro Glu Trp Val Cys Thr
        35                  40                  45
Ala Phe His Thr Ser Gly Tyr Asp Thr Gln Ala Ile Val Gln Asn Asn
    50                  55                  60
Asp Ser Thr Glu Tyr Gly Leu Phe Gln Ile Asn Asn Lys Ile Trp Cys
65                  70                  75                  80
Lys Asp Asp Gln Asn Pro His Ser Ser Asn Ile Cys Asn Ile Ser Cys
                85                  90                  95
Asp Lys Phe Leu Asp Asp Asp Leu Thr Asp Asp Ile Met Cys Val Lys
            100                 105                 110
```

```
Lys Ile Leu Asp Lys Val Gly Ile Asn Tyr Trp Leu Ala His Lys Ala
            115                 120                 125

Leu Cys Ser Glu Lys Leu Asp Gln Trp Leu Cys Glu Lys Leu
            130                 135                 140
```

<210> SEQ ID NO 23
<211> LENGTH: 711
<212> TYPE: PRT
<213> ORGANISM: Bos taurus

<400> SEQUENCE: 23

```
Trp Val Cys Leu Gln Leu Pro Val Phe Leu Ala Ser Val Thr Leu Phe
1               5                   10                  15

Glu Val Ala Ala Ser Asp Thr Ile Ala Gln Ala Ser Thr Thr Thr
            20                  25                  30

Ile Ser Asp Ala Val Ser Lys Val Lys Ile Gln Val Asn Lys Ala Phe
            35                  40                  45

Leu Asp Ser Arg Thr Arg Leu Lys Thr Thr Leu Ser Ser Glu Ala Pro
        50                  55                  60

Thr Thr Gln Gln Leu Ser Glu Tyr Phe Lys His Ala Lys Gly Arg Thr
65                  70                  75                  80

Arg Thr Ala Ile Arg Asn Gly Gln Val Trp Glu Ser Leu Lys Arg
                85                  90                  95

Leu Arg Arg Asp Thr Thr Leu Thr Asn Val Thr Asp Pro Ser Leu Asp
                100                 105                 110

Leu Thr Ala Leu Ser Trp Glu Val Gly Cys Gly Ala Pro Val Pro Leu
            115                 120                 125

Val Lys Cys Asp Glu Asn Ser Pro Tyr Arg Thr Ile Thr Gly Asp Cys
        130                 135                 140

Asn Asn Arg Arg Ser Pro Ala Leu Gly Ala Ala Asn Arg Ala Leu Ala
145                 150                 155                 160

Arg Trp Leu Pro Ala Glu Tyr Glu Asp Gly Leu Ala Leu Pro Phe Gly
                165                 170                 175

Trp Thr Gln Arg Lys Thr Arg Asn Gly Phe Arg Val Pro Leu Ala Arg
            180                 185                 190

Glu Val Ser Asn Lys Ile Val Gly Tyr Leu Asp Glu Glu Gly Val Leu
        195                 200                 205

Asp Gln Asn Arg Ser Leu Leu Phe Met Gln Trp Gly Gln Ile Val Asp
    210                 215                 220

His Asp Leu Asp Phe Ala Pro Glu Thr Glu Leu Gly Ser Asn Glu His
225                 230                 235                 240

Ser Lys Thr Gln Cys Glu Glu Tyr Cys Ile Gln Gly Asp Asn Cys Phe
                245                 250                 255

Pro Ile Met Phe Pro Lys Asn Asp Pro Lys Leu Lys Thr Gln Gly Lys
            260                 265                 270

Cys Met Pro Phe Phe Arg Ala Gly Phe Val Cys Pro Thr Pro Pro Tyr
        275                 280                 285

Gln Ser Leu Ala Arg Glu Gln Ile Asn Ala Val Thr Ser Phe Leu Asp
    290                 295                 300

Ala Ser Leu Val Tyr Gly Ser Glu Pro Ser Leu Ala Ser Arg Leu Arg
305                 310                 315                 320

Asn Leu Ser Ser Pro Leu Gly Leu Met Ala Val Asn Gln Glu Ala Trp
                325                 330                 335

Asp His Gly Leu Ala Tyr Leu Pro Phe Asn Asn Lys Lys Pro Ser Pro
```

```
                        340                 345                 350
        Cys Glu Phe Ile Asn Thr Thr Ala Arg Val Pro Cys Phe Leu Ala Gly
                355                 360                 365

Asp Phe Arg Ala Ser Glu Gln Ile Leu Leu Ala Thr Ala His Thr Leu
            370                 375                 380

Leu Leu Arg Glu His Asn Arg Leu Ala Arg Glu Leu Lys Lys Leu Asn
        385                 390                 395                 400

Pro His Trp Asn Gly Glu Lys Leu Tyr Gln Glu Ala Arg Lys Ile Leu
                        405                 410                 415

Gly Ala Phe Ile Gln Ile Ile Thr Phe Arg Asp Tyr Leu Pro Ile Val
                    420                 425                 430

Leu Gly Ser Glu Met Gln Lys Trp Ile Pro Pro Tyr Gln Gly Tyr Asn
                435                 440                 445

Asn Ser Val Asp Pro Arg Ile Ser Asn Val Phe Thr Phe Ala Phe Arg
            450                 455                 460

Phe Gly His Met Glu Val Pro Ser Thr Val Ser Arg Leu Asp Glu Asn
        465                 470                 475                 480

Tyr Gln Pro Trp Gly Pro Glu Ala Glu Leu Pro Leu His Thr Leu Phe
                        485                 490                 495

Phe Asn Thr Trp Arg Ile Ile Lys Asp Gly Ile Asp Pro Leu Val
                    500                 505                 510

Arg Gly Leu Leu Ala Lys Lys Ser Lys Leu Met Asn Gln Asp Lys Met
                515                 520                 525

Val Thr Ser Glu Leu Arg Asn Lys Leu Phe Gln Pro Thr His Lys Ile
            530                 535                 540

His Gly Phe Asp Leu Ala Ala Ile Asn Leu Gln Arg Cys Arg Asp His
        545                 550                 555                 560

Gly Met Pro Gly Tyr Asn Ser Trp Arg Gly Phe Cys Gly Leu Ser Gln
                        565                 570                 575

Pro Lys Thr Leu Lys Gly Leu Gln Thr Val Leu Lys Asn Lys Ile Leu
                    580                 585                 590

Ala Lys Lys Leu Met Asp Leu Tyr Lys Thr Pro Asp Asn Ile Asp Ile
                595                 600                 605

Trp Ile Gly Gly Asn Ala Glu Pro Met Val Glu Arg Gly Arg Val Gly
            610                 615                 620

Pro Leu Leu Ala Cys Leu Leu Gly Arg Gln Phe Gln Gln Ile Arg Asp
        625                 630                 635                 640

Gly Asp Arg Phe Trp Trp Glu Asn Pro Gly Val Phe Thr Glu Lys Gln
                        645                 650                 655

Arg Asp Ser Leu Gln Lys Val Ser Phe Ser Arg Leu Ile Cys Asp Asn
                    660                 665                 670

Thr His Ile Thr Lys Val Pro Leu His Ala Phe Gln Ala Asn Asn Tyr
                675                 680                 685

Pro His Asp Phe Val Asp Cys Ser Thr Val Asp Lys Leu Asp Leu Ser
            690                 695                 700

Pro Trp Ala Ser Arg Glu Asn
        705                 710

<210> SEQ ID NO 24
<211> LENGTH: 708
<212> TYPE: PRT
<213> ORGANISM: Bos taurus

<400> SEQUENCE: 24
```

```
Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
            35                  40                  45

Gly Ala Pro Ser Ile Thr Cys Val Arg Arg Ala Phe Ala Leu Glu Cys
50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
            115                 120                 125

Gln Gly Arg Lys Ser Cys His Thr Gly Leu Gly Arg Ser Ala Gly Trp
130                 135                 140

Val Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
            165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
            195                 200                 205

Phe Gly Tyr Ser Gly Ala Phe Lys Cys Leu Gln Asp Gly Ala Gly Asp
            210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
            245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
            275                 280                 285

Leu Leu Ser Lys Ala Gln Glu Lys Phe Gly Lys Asn Lys Ser Arg Ser
            290                 295                 300

Phe Gln Leu Phe Gly Ser Pro Gly Gln Arg Asp Leu Leu Phe Lys
305                 310                 315                 320

Asp Ser Ala Leu Gly Phe Leu Arg Ile Pro Ser Lys Val Asp Ser Ala
            325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
            355                 360                 365

Val Gly Pro Glu Glu Gln Lys Lys Cys Gln Gln Trp Ser Gln Gln Ser
            370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
            405                 410                 415

Tyr Ile Tyr Thr Ala Gly Lys Cys Gly Leu Val Pro Val Leu Ala Glu
```

```
            420                 425                 430
Asn Arg Lys Thr Ser Lys Tyr Ser Ser Leu Asp Cys Val Leu Arg Pro
            435                 440                 445
Thr Glu Gly Tyr Leu Ala Val Ala Val Val Lys Lys Ala Asn Glu Gly
        450                 455                 460
Leu Thr Trp Asn Ser Leu Lys Asp Lys Lys Ser Cys His Thr Ala Val
465                 470                 475                 480
Asp Arg Thr Ala Gly Trp Asn Ile Pro Met Gly Leu Ile Val Asn Gln
                485                 490                 495
Thr Gly Ser Cys Ala Phe Asp Glu Phe Phe Ser Gln Ser Cys Ala Pro
            500                 505                 510
Gly Arg Asp Pro Lys Ser Arg Leu Cys Ala Leu Cys Ala Gly Asp Asp
            515                 520                 525
Gln Gly Leu Asp Lys Cys Val Pro Asn Ser Lys Glu Lys Tyr Tyr Gly
        530                 535                 540
Tyr Thr Gly Ala Phe Arg Cys Leu Ala Glu Asp Val Gly Asp Val Ala
545                 550                 555                 560
Phe Val Lys Asn Asp Thr Val Trp Glu Asn Thr Asn Gly Glu Ser Thr
                565                 570                 575
Ala Asp Trp Ala Lys Asn Leu Asn Arg Glu Asp Phe Arg Leu Leu Cys
            580                 585                 590
Leu Asp Gly Thr Arg Lys Pro Val Thr Glu Ala Gln Ser Cys His Leu
            595                 600                 605
Ala Val Ala Pro Asn His Ala Val Val Ser Arg Ser Asp Arg Ala Ala
        610                 615                 620
His Val Lys Gln Val Leu Leu His Gln Gln Ala Leu Phe Gly Lys Asn
625                 630                 635                 640
Gly Lys Asn Cys Pro Asp Lys Phe Cys Leu Phe Lys Ser Glu Thr Lys
                645                 650                 655
Asn Leu Leu Phe Asn Asp Asn Thr Glu Cys Leu Ala Lys Leu Gly Gly
            660                 665                 670
Arg Pro Thr Tyr Glu Glu Tyr Leu Gly Thr Glu Tyr Val Thr Ala Ile
            675                 680                 685
Ala Asn Leu Lys Lys Cys Ser Thr Ser Pro Leu Leu Glu Ala Cys Ala
        690                 695                 700
Phe Leu Thr Arg
705

<210> SEQ ID NO 25
<211> LENGTH: 164
<212> TYPE: PRT
<213> ORGANISM: Bos taurus

<400> SEQUENCE: 25

Met Asn Pro Leu Trp Thr Leu Leu Phe Val Leu Ser Ala Pro Arg Gly
1               5                   10                  15
Val Leu Ser Gln Val Gln Leu Arg Glu Ser Gly Pro Ser Leu Val Lys
                20                  25                  30
Pro Ser Gln Thr Leu Ser Leu Thr Cys Thr Val Ser Gly Phe Ser Leu
            35                  40                  45
Ser Ser Tyr Ala Val Gly Trp Val Arg Gln Ala Pro Gly Lys Ala Leu
        50                  55                  60
Glu Trp Val Gly Gly Ile Asp Gly Gly Gly Ser Thr Tyr Tyr Asn Pro
65                  70                  75                  80
```

```
Ala Leu Lys Ser Arg Leu Ser Ile Thr Lys Asp Asn Ser Lys Ser Gln
                85                  90                  95

Val Ser Leu Ser Val Ser Val Thr Pro Glu Asp Thr Ala Thr Tyr
            100                 105                 110

Tyr Cys Ala Lys Cys Val Gly Tyr Ala Gly Ser Arg Ser Gly Cys Tyr
            115                 120                 125

Tyr Leu Arg Gly Gly Tyr Gly Pro His Val Asp Ala Trp Gly Gln Gly
            130                 135                 140

Leu Leu Val Thr Val Ser Ser Ala Ser Thr Thr Ala Pro Lys Val Tyr
145                 150                 155                 160

Pro Leu Ser Ser

<210> SEQ ID NO 26
<211> LENGTH: 101
<212> TYPE: PRT
<213> ORGANISM: Bos taurus

<400> SEQUENCE: 26

Gln Ser Gly Leu Thr Gln Pro Ser Ser Val Ser Gly Asn Leu Gly Gln
1               5                   10                  15

Thr Val Ile Thr Ser Cys Ala Gly Thr Ser Ser Tyr Val Gly Ser Tyr
            20                  25                  30

Asn Gly Val Gly Trp Tyr Gln Gln Leu Pro Gly Ser Ala Pro Lys Thr
        35                  40                  45

Leu Ile Tyr Asn Val Ser Lys Arg Pro Ser Gly Ile Pro Asp Arg Phe
    50                  55                  60

Ser Gly Ser Lys Ser Gly Asn Thr Ala Thr Leu Thr Val Ser Gly Leu
65                  70                  75                  80

Gln Ala Glu Asp Glu Ala Asp Tyr Tyr Cys Ser Ser Tyr Lys Ser Gly
                85                  90                  95

Gly Ser Val His Ser
            100

<210> SEQ ID NO 27
<211> LENGTH: 607
<212> TYPE: PRT
<213> ORGANISM: Bos taurus

<400> SEQUENCE: 27

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
            115                 120                 125

His Lys Asp Asp Ser Pro Asp Leu Pro Lys Leu Lys Pro Asp Pro Asn
```

-continued

```
                130                 135                 140
Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
            195                 200                 205

Arg Glu Lys Val Leu Ala Ser Ser Ala Arg Gln Arg Leu Arg Cys Ala
        210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
                260                 265                 270

Leu Leu Glu Cys Ala Asp Asp Arg Ala Asp Leu Ala Lys Tyr Ile Cys
            275                 280                 285

Asp Asn Gln Asp Thr Ile Ser Ser Lys Leu Lys Glu Cys Cys Asp Lys
        290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
            355                 360                 365

Leu Leu Arg Leu Ala Lys Glu Tyr Glu Ala Thr Leu Glu Glu Cys Cys
        370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
            435                 440                 445

Val Ser Arg Ser Leu Gly Lys Val Gly Thr Arg Cys Cys Thr Lys Pro
        450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
            515                 520                 525

Leu Phe Thr Phe His Ala Asp Ile Cys Thr Leu Pro Asp Thr Glu Lys
        530                 535                 540

Gln Ile Lys Lys Gln Thr Ala Leu Val Glu Leu Leu Lys His Lys Pro
545                 550                 555                 560
```

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605

<210> SEQ ID NO 28
<211> LENGTH: 563
<212> TYPE: PRT
<213> ORGANISM: Glycine max

<400> SEQUENCE: 28

Met Gly Lys Pro Phe Thr Leu Ser Leu Ser Ser Leu Cys Leu Leu Leu
1               5                   10                  15

Leu Ser Ser Ala Cys Phe Ala Ile Ser Ser Lys Leu Asn Glu Cys
            20                  25                  30

Gln Leu Asn Asn Leu Asn Ala Leu Glu Pro Asp His Arg Val Glu Ser
        35                  40                  45

Glu Gly Gly Leu Ile Gln Thr Trp Asn Ser Gln His Pro Glu Leu Lys
    50                  55                  60

Cys Ala Gly Val Thr Val Ser Lys Leu Thr Leu Asn Arg Asn Gly Leu
65                  70                  75                  80

His Leu Pro Ser Tyr Ser Pro Tyr Pro Arg Met Ile Ile Ile Ala Gln
                85                  90                  95

Gly Lys Gly Ala Leu Gly Val Ala Ile Pro Gly Cys Pro Glu Thr Phe
            100                 105                 110

Glu Glu Pro Gln Glu Gln Ser Asn Arg Arg Gly Ser Arg Ser Gln Lys
        115                 120                 125

Gln Gln Leu Gln Asp Ser His Gln Lys Ile Arg His Phe Asn Glu Gly
    130                 135                 140

Asp Val Leu Val Ile Pro Pro Gly Val Pro Tyr Trp Thr Tyr Asn Thr
145                 150                 155                 160

Gly Asp Glu Pro Val Val Ala Ile Ser Leu Leu Asp Thr Ser Asn Phe
                165                 170                 175

Asn Asn Gln Leu Asp Gln Thr Pro Arg Val Phe Tyr Leu Ala Gly Asn
            180                 185                 190

Pro Asp Ile Glu Tyr Pro Glu Thr Met Gln Gln Gln Gln Gln Gln Lys
        195                 200                 205

Ser His Gly Gly Arg Lys Gln Gly Gln His Gln Glu Glu Glu Glu
    210                 215                 220

Glu Gly Gly Ser Val Leu Ser Gly Phe Ser Lys His Phe Leu Ala Gln
225                 230                 235                 240

Ser Phe Asn Thr Asn Glu Asp Ile Ala Glu Lys Leu Gln Ser Pro Asp
                245                 250                 255

Asp Glu Arg Lys Gln Ile Val Thr Val Glu Gly Gly Leu Ser Val Ile
            260                 265                 270

Ser Pro Lys Trp Gln Glu Gln Asp Glu Asp Glu Asp Glu
        275                 280                 285

Asp Asp Glu Asp Glu Gln Ile Pro Ser His Pro Arg Arg Pro Ser
    290                 295                 300

His Gly Lys Arg Glu Gln Asp Glu Asp Glu Asp Glu Asp Lys
305                 310                 315                 320

Pro Arg Pro Ser Arg Pro Ser Gln Gly Lys Arg Glu Gln Asp Gln Asp

```
                    325                 330                 335
Gln Asp Glu Asp Glu Asp Glu Asp Gln Pro Arg Lys Ser Arg
                340                 345                 350
Glu Trp Arg Ser Lys Lys Thr Gln Pro Arg Pro Arg Gln Glu Glu
            355                 360                 365
Pro Arg Glu Arg Gly Cys Glu Thr Arg Asn Gly Val Glu Glu Asn Ile
    370                 375                 380
Cys Thr Leu Lys Leu His Glu Asn Ile Ala Arg Pro Ser Arg Ala Asp
385                 390                 395                 400
Phe Tyr Asn Pro Lys Ala Gly Arg Ile Ser Thr Leu Asn Ser Leu Thr
                405                 410                 415
Leu Pro Ala Leu Arg Gln Phe Gln Leu Ser Ala Gln Tyr Val Val Leu
            420                 425                 430
Tyr Lys Asn Gly Ile Tyr Ser Pro His Trp Asn Leu Asn Ala Asn Ser
        435                 440                 445
Val Ile Tyr Val Thr Arg Gly Gln Gly Lys Val Arg Val Asn Cys
450                 455                 460
Gln Gly Asn Ala Val Phe Asp Gly Glu Leu Arg Arg Gly Gln Leu Leu
465                 470                 475                 480
Val Val Pro Gln Asn Phe Val Val Ala Glu Gln Ala Gly Glu Gln Gly
                485                 490                 495
Phe Glu Tyr Ile Val Phe Lys Thr His His Asn Ala Val Thr Ser Tyr
            500                 505                 510
Leu Lys Asp Val Phe Arg Ala Ile Pro Ser Glu Val Leu Ala His Ser
        515                 520                 525
Tyr Asn Leu Arg Gln Ser Gln Val Ser Glu Leu Lys Tyr Glu Gly Asn
    530                 535                 540
Trp Gly Pro Leu Val Asn Pro Glu Ser Gln Gln Gly Ser Pro Arg Val
545                 550                 555                 560
Lys Val Ala

<210> SEQ ID NO 29
<211> LENGTH: 639
<212> TYPE: PRT
<213> ORGANISM: Glycine max

<400> SEQUENCE: 29

Met Met Arg Ala Arg Phe Pro Leu Leu Leu Leu Gly Val Val Phe Leu
1               5                   10                  15
Ala Ser Val Ser Val Ser Phe Gly Ile Ala Tyr Trp Glu Lys Gln Asn
            20                  25                  30
Pro Ser His Asn Lys Cys Leu Arg Ser Cys Asn Ser Glu Lys Asp Ser
        35                  40                  45
Tyr Arg Asn Gln Ala Cys His Ala Arg Cys Asn Leu Leu Lys Val Glu
    50                  55                  60
Glu Glu Glu Glu Cys Glu Glu Gly Gln Ile Pro Arg Pro Arg Pro Gln
65                  70                  75                  80
His Pro Glu Arg Glu Arg Gln Gln His Gly Glu Lys Glu Glu Asp Glu
                85                  90                  95
Gly Glu Gln Pro Arg Pro Phe Pro Phe Pro Arg Pro Arg Gln Pro His
            100                 105                 110
Gln Glu Glu Glu His Glu Gln Lys Glu Glu His Glu Trp His Arg Lys
        115                 120                 125
Glu Glu Lys His Gly Gly Lys Gly Ser Glu Glu Glu Gln Asp Glu Arg
```

```
                130             135             140
Glu His Pro Arg Pro His Gln Pro His Gln Lys Glu Glu Lys His
145                 150             155                 160

Glu Trp Gln His Lys Gln Glu Lys His Gln Gly Lys Glu Ser Glu
                165             170             175

Glu Glu Glu Asp Gln Asp Glu Asp Glu Gln Asp Lys Glu Ser Gln
            180             185             190

Glu Ser Glu Gly Ser Glu Ser Gln Arg Glu Pro Arg Arg His Lys Asn
        195             200             205

Lys Asn Pro Phe His Phe Asn Ser Lys Arg Phe Gln Thr Leu Phe Lys
210                 215             220

Asn Gln Tyr Gly His Val Arg Val Leu Gln Arg Phe Asn Lys Arg Ser
225                 230             235                 240

Gln Gln Leu Gln Asn Leu Arg Asp Tyr Arg Ile Leu Glu Phe Asn Ser
                245             250             255

Lys Pro Asn Thr Leu Leu Pro His His Ala Asp Ala Asp Tyr Leu
            260             265             270

Ile Val Ile Leu Asn Gly Thr Ala Ile Leu Thr Leu Val Asn Asn Asp
        275             280             285

Asp Arg Asp Ser Tyr Asn Leu Gln Ser Gly Asp Ala Leu Arg Val Pro
290                 295             300

Ala Gly Thr Thr Phe Tyr Val Val Asn Pro Asp Asn Asp Glu Asn Leu
305                 310             315                 320

Arg Met Ile Ala Gly Thr Thr Phe Tyr Val Val Asn Pro Asp Asn Asp
                325             330             335

Glu Asn Leu Arg Met Ile Thr Leu Ala Ile Pro Val Asn Lys Pro Gly
            340             345             350

Arg Phe Glu Ser Phe Phe Leu Ser Ser Thr Gln Ala Gln Gln Ser Tyr
                355             360             365

Leu Gln Gly Phe Ser Lys Asn Ile Leu Glu Ala Ser Tyr Asp Thr Lys
        370             375             380

Phe Glu Glu Ile Asn Lys Val Leu Phe Gly Arg Glu Glu Gly Gln Gln
385                 390             395             400

Gln Gly Glu Glu Arg Leu Gln Glu Ser Val Ile Val Glu Ile Ser Lys
            405             410             415

Lys Gln Ile Arg Glu Leu Ser Lys His Ala Lys Ser Ser Ser Arg Lys
        420             425             430

Thr Ile Ser Ser Glu Asp Lys Pro Phe Asn Leu Gly Ser Arg Asp Pro
        435             440             445

Ile Tyr Ser Asn Lys Leu Gly Lys Leu Phe Glu Ile Thr Gln Arg Asn
        450             455             460

Pro Gln Leu Arg Asp Leu Asp Val Phe Leu Ser Val Val Asp Met Asn
465                 470             475             480

Glu Gly Ala Leu Phe Leu Pro His Phe Asn Ser Lys Ala Ile Val Val
                485             490             495

Leu Val Ile Asn Glu Gly Glu Ala Asn Ile Glu Leu Val Gly Ile Lys
            500             505             510

Glu Gln Gln Gln Arg Gln Gln Glu Glu Gln Pro Leu Glu Val Arg
        515             520             525

Lys Tyr Arg Ala Glu Leu Ser Glu Gln Asp Ile Phe Val Ile Pro Ala
530                 535             540

Gly Tyr Pro Val Met Val Asn Ala Thr Ser Asp Leu Asn Phe Phe Ala
545                 550             555             560
```

Phe Gly Ile Asn Ala Glu Asn Gln Arg Asn Phe Leu Ala Gly Ser
              565                 570                 575

Lys Asp Asn Val Ile Ser Gln Ile Pro Ser Gln Val Gln Glu Leu Ala
            580                 585                 590

Phe Pro Arg Ser Ala Lys Asp Ile Glu Asn Leu Ile Lys Ser Gln Ser
        595                 600                 605

Glu Ser Tyr Phe Val Asp Ala Gln Pro Gln Gln Lys Glu Glu Gly Asn
    610                 615                 620

Lys Gly Arg Lys Gly Pro Leu Ser Ser Ile Leu Arg Ala Phe Tyr
625                 630                 635

<210> SEQ ID NO 30
<211> LENGTH: 623
<212> TYPE: PRT
<213> ORGANISM: Glycine max

<400> SEQUENCE: 30

Met Arg Ala Arg Phe Pro Leu Leu Leu Leu Gly Val Val Phe Leu Ala
1               5                   10                  15

Ser Val Ser Val Ser Phe Gly Ile Ala Tyr Trp Glu Lys Gln Asn Pro
            20                  25                  30

Lys His Asn Lys Cys Leu Gln Ser Cys Asn Ser Glu Arg Asp Ser Tyr
        35                  40                  45

Arg Asn Gln Ala Cys His Ala Arg Cys Asn Leu Leu Lys Val Glu Lys
    50                  55                  60

Glu Glu Glu Cys Glu Glu Gly Glu Ile Pro Arg Pro Arg Pro Arg Pro
65                  70                  75                  80

Gln His Pro Glu Arg Glu Pro Gln Gln Pro Gly Glu Lys Glu Glu Asp
                85                  90                  95

Glu Asp Glu Gln Pro Arg Pro Ile Pro Phe Pro Arg Pro Arg Gln Pro
            100                 105                 110

Arg Gln Glu Glu Glu His Glu Gln Arg Glu Glu Gln Glu Trp Pro Arg
        115                 120                 125

Lys Glu Glu Lys Arg Gly Glu Lys Gly Ser Glu Glu Glu Gln Asp Gly
130                 135                 140

Arg Glu His Pro Arg Pro His Gln Pro His Asp Glu Asp Glu Glu Gln
145                 150                 155                 160

Asp Glu Arg Gln Phe Pro Phe Pro Arg Pro Pro His Gln Lys Glu Ser
                165                 170                 175

Glu Glu Arg Lys Gln Glu Glu Asp Glu Asp Glu Glu Gln Arg Glu
            180                 185                 190

Ser Glu Glu Ser Glu Ser Ser Glu Ser Gln Arg Glu Leu Arg Arg His
        195                 200                 205

Lys Asn Lys Asn Pro Phe His Phe Gly Ser Asn Arg Phe Glu Thr Leu
210                 215                 220

Phe Lys Asn Gln Tyr Gly Arg Ile Arg Val Leu Gln Arg Phe Asn Gln
225                 230                 235                 240

Arg Ser Pro Gln Leu Gln Asn Leu Arg Asp Tyr Arg Ile Leu Glu Phe
                245                 250                 255

Asn Ser Lys Pro Asn Thr Leu Leu Pro Asn His Ala Asp Ala Asp
            260                 265                 270

Tyr Leu Ile Ala Ile Leu Asn Gly Thr Ala Ile Leu Ser Leu Val Asn
        275                 280                 285

Asn Asp Asp Arg Asp Ser Tyr Arg Leu Gln Ser Gly Asp Ala Leu Arg

```
        290                 295                 300
Val Pro Ser Gly Thr Thr Tyr Tyr Val Val Asn Pro Asp Asn Asn Glu
305                 310                 315                 320

Asn Leu Arg Leu Ile Thr Leu Ala Ile Pro Val Asn Lys Pro Gly Arg
                325                 330                 335

Phe Glu Ser Phe Phe Leu Ser Ser Thr Glu Ala Gln Gln Ser Tyr Leu
            340                 345                 350

Gln Gly Phe Ser Arg Asn Ile Leu Glu Ala Ser Tyr Asp Thr Lys Phe
            355                 360                 365

Glu Glu Ile Asn Lys Val Leu Phe Ser Arg Glu Glu Gly Gln Gln Gln
370                 375                 380

Gly Glu Gln Arg Leu Gln Glu Ser Val Ile Val Glu Ile Ser Lys Glu
385                 390                 395                 400

Gln Ile Arg Ala Leu Ser Lys Arg Ala Lys Ser Ser Arg Lys Thr
                405                 410                 415

Ile Ser Ser Glu Asp Lys Pro Phe Asn Leu Arg Ser Arg Asp Pro Ile
            420                 425                 430

Tyr Ser Asn Lys Leu Gly Lys Phe Phe Glu Ile Thr Pro Glu Lys Asn
            435                 440                 445

Pro Gln Leu Arg Asp Leu Asp Ile Phe Leu Ser Ile Val Asp Met Asn
            450                 455                 460

Glu Gly Ala Leu Leu Pro His Phe Asn Ser Lys Ala Ile Val Ile
465                 470                 475                 480

Leu Val Ile Asn Glu Gly Asp Ala Asn Ile Glu Leu Val Gly Leu Lys
                485                 490                 495

Glu Gln Gln Gln Glu Glu Gln Gln Glu Gln Pro Leu Glu Val Arg
            500                 505                 510

Lys Tyr Arg Ala Glu Leu Ser Glu Gln Asp Ile Phe Val Ile Pro Ala
            515                 520                 525

Gly Tyr Pro Val Val Val Asn Ala Thr Ser Asn Leu Asn Phe Phe Ala
            530                 535                 540

Ile Gly Ile Asn Ala Glu Asn Asn Gln Arg Asn Phe Leu Ala Gly Ser
545                 550                 555                 560

Gln Asp Asn Val Ile Ser Gln Ile Pro Ser Gln Val Gln Glu Leu Ala
                565                 570                 575

Phe Leu Gly Ser Ala Gln Ala Val Glu Lys Leu Leu Lys Asn Gln Arg
            580                 585                 590

Glu Ser Tyr Phe Val Asp Ala Gln Pro Lys Lys Glu Glu Gly Asn
            595                 600                 605

Lys Gly Arg Lys Gly Pro Leu Ser Ser Ile Leu Arg Ala Phe Tyr
610                 615                 620

<210> SEQ ID NO 31
<211> LENGTH: 439
<212> TYPE: PRT
<213> ORGANISM: Glycine max

<400> SEQUENCE: 31

Met Met Arg Val Arg Phe Pro Leu Leu Val Leu Leu Gly Thr Val Phe
1               5                   10                  15

Leu Ala Ser Val Cys Val Ser Leu Lys Val Arg Glu Asp Glu Asn Asn
                20                  25                  30

Pro Phe Tyr Phe Arg Ser Ser Asn Ser Phe Gln Thr Leu Phe Glu Asn
            35                  40                  45
```

```
Gln Asn Val Arg Ile Arg Leu Leu Gln Arg Phe Asn Lys Arg Ser Pro
 50                  55                  60

Gln Leu Glu Asn Leu Arg Asp Tyr Arg Ile Val Gln Phe Gln Ser Lys
 65                  70                  75                  80

Pro Asn Thr Ile Leu Leu Pro His His Ala Asp Ala Asp Phe Leu Leu
                 85                  90                  95

Phe Val Leu Ser Gly Arg Ala Ile Leu Thr Leu Val Asn Asn Asp Asp
            100                 105                 110

Arg Asp Ser Tyr Asn Leu His Pro Gly Asp Ala Gln Arg Ile Pro Ala
        115                 120                 125

Gly Thr Thr Tyr Tyr Leu Val Asn Pro His Asp His Gln Asn Leu Lys
130                 135                 140

Ile Ile Lys Leu Ala Ile Pro Val Asn Lys Pro Gly Arg Tyr Asp Asp
145                 150                 155                 160

Phe Phe Leu Ser Ser Thr Gln Ala Gln Gln Ser Tyr Leu Gln Gly Phe
                165                 170                 175

Ser His Asn Ile Leu Glu Thr Ser Phe His Ser Glu Phe Glu Glu Ile
            180                 185                 190

Asn Arg Val Leu Phe Gly Glu Glu Glu Gln Arg Gln Gln Glu Gly
        195                 200                 205

Val Ile Val Glu Leu Ser Lys Glu Gln Ile Arg Gln Leu Ser Arg Arg
210                 215                 220

Ala Lys Ser Ser Ser Arg Lys Thr Ile Ser Ser Glu Asp Glu Pro Phe
225                 230                 235                 240

Asn Leu Arg Ser Arg Asn Pro Ile Tyr Ser Asn Asn Phe Gly Lys Phe
                245                 250                 255

Phe Glu Ile Thr Pro Glu Lys Asn Pro Gln Leu Arg Asp Leu Asp Ile
            260                 265                 270

Phe Leu Ser Ser Val Asp Ile Asn Glu Gly Ala Leu Leu Pro His
        275                 280                 285

Phe Asn Ser Lys Ala Ile Val Ile Leu Val Ile Asn Glu Gly Asp Ala
290                 295                 300

Asn Ile Glu Leu Val Gly Ile Lys Glu Gln Gln Gln Lys Gln Lys Gln
305                 310                 315                 320

Glu Glu Glu Pro Leu Glu Val Gln Arg Tyr Arg Ala Glu Leu Ser Glu
                325                 330                 335

Asp Asp Val Phe Val Ile Pro Ala Ala Tyr Pro Phe Val Val Asn Ala
            340                 345                 350

Thr Ser Asn Leu Asn Phe Leu Ala Phe Gly Ile Asn Ala Glu Asn Asn
        355                 360                 365

Gln Arg Asn Phe Leu Ala Gly Glu Lys Asp Asn Val Val Arg Gln Ile
370                 375                 380

Glu Arg Gln Val Gln Glu Leu Ala Phe Pro Gly Ser Ala Gln Asp Val
385                 390                 395                 400

Glu Arg Leu Leu Lys Lys Gln Arg Glu Ser Tyr Phe Val Asp Ala Gln
                405                 410                 415

Pro Gln Gln Lys Glu Glu Gly Ser Lys Gly Arg Lys Gly Pro Phe Pro
            420                 425                 430

Ser Ile Leu Gly Ala Leu Tyr
            435

<210> SEQ ID NO 32
<211> LENGTH: 288
<212> TYPE: PRT
```

<213> ORGANISM: Triticum sp.

<400> SEQUENCE: 32

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Pro Phe Pro Pro Gln Gln Pro Tyr Pro
    50                  55                  60

Gln Pro Gln Pro Phe Pro Ser Gln Pro Tyr Leu Gln Leu Gln Pro
65                  70                  75                  80

Phe Pro Gln Pro Gln Leu Pro Tyr Ser Gln Pro Gln Pro Phe Arg Pro
                85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Gln Gln Gln Gln Ile Leu Gln Gln Ile Leu Gln Gln Gln
    130                 135                 140

Leu Ile Pro Cys Met Asp Val Val Leu Gln Gln His Asn Ile Ala His
145                 150                 155                 160

Gly Arg Ser Gln Val Leu Gln Gln Ser Thr Tyr Gln Leu Leu Gln Glu
                165                 170                 175

Leu Cys Cys Gln His Leu Trp Gln Ile Pro Glu Gln Ser Gln Cys Gln
            180                 185                 190

Ala Ile His Lys Val Val His Ala Ile Ile Leu His Gln Gln Gln Lys
        195                 200                 205

Gln Gln Gln Gln Pro Ser Ser Gln Val Ser Phe Gln Gln Pro Leu Gln
    210                 215                 220

Gln Tyr Pro Leu Gly Gln Gly Ser Phe Arg Pro Ser Gln Gln Asn Pro
225                 230                 235                 240

Gln Ala Gln Gly Ser Val Gln Pro Gln Gln Leu Pro Gln Phe Glu Glu
                245                 250                 255

Ile Arg Asn Leu Ala Leu Gln Thr Leu Pro Ala Met Cys Asn Val Tyr
            260                 265                 270

Ile Pro Pro Tyr Cys Thr Ile Thr Pro Phe Gly Ile Phe Gly Thr Asn
        275                 280                 285

<210> SEQ ID NO 33
<211> LENGTH: 302
<212> TYPE: PRT
<213> ORGANISM: Triticum sp.

<400> SEQUENCE: 33

Met Lys Thr Leu Leu Ile Leu Thr Ile Leu Ala Met Ala Thr Thr Ile
1               5                   10                  15

Ala Thr Ala Asn Met Gln Val Asp Pro Ser Gly Gln Val Gln Trp Pro
            20                  25                  30

Gln Gln Gln Pro Phe Pro Gln Pro Gln Pro Phe Cys Gln Gln Pro
        35                  40                  45

Gln Arg Thr Ile Pro Gln Pro His Gln Thr Phe His His Gln Pro Gln
    50                  55                  60

Gln Thr Phe Pro Gln Pro Gln Gln Thr Tyr Pro His Gln Pro Gln Gln

```
                65                  70                  75                  80
Gln Phe Pro Gln Thr Gln Gln Pro Gln Gln Pro Phe Pro Gln Pro Gln
                    85                  90                  95
Gln Thr Phe Pro Gln Gln Pro Gln Leu Pro Phe Pro Gln Gln Pro Gln
                100                 105                 110
Gln Pro Phe Pro Gln Pro Gln Gln Pro Gln Gln Pro Phe Pro Gln Ser
                115                 120                 125
Gln Gln Pro Gln Gln Pro Phe Pro Gln Pro Gln Gln Gln Phe Pro Gln
                130                 135                 140
Pro Gln Gln Pro Gln Gln Ser Phe Pro Gln Gln Gln Pro Ala Ile
145                 150                 155                 160
Gln Ser Phe Leu Gln Gln Gln Met Asn Pro Cys Lys Asn Phe Leu Leu
                165                 170                 175
Gln Gln Cys Asn His Val Ser Leu Val Ser Ser Leu Val Ser Ile Ile
                180                 185                 190
Leu Pro Arg Ser Asp Cys Gln Val Met Gln Gln Gln Cys Cys Gln Gln
                195                 200                 205
Leu Ala Gln Ile Pro Gln Gln Leu Gln Cys Ala Ala Ile His Ser Val
                210                 215                 220
Ala His Ser Ile Ile Met Gln Gln Glu Gln Gln Gln Gly Val Pro Ile
225                 230                 235                 240
Leu Arg Pro Leu Phe Gln Leu Ala Gln Gly Leu Gly Ile Ile Gln Pro
                    245                 250                 255
Gln Gln Pro Ala Gln Leu Glu Gly Ile Arg Ser Leu Val Leu Lys Thr
                260                 265                 270
Leu Pro Thr Met Cys Asn Val Tyr Val Pro Pro Asp Cys Ser Thr Ile
                275                 280                 285
Asn Val Pro Tyr Ala Asn Ile Asp Ala Gly Ile Gly Gly Gln
                290                 295                 300

<210> SEQ ID NO 34
<211> LENGTH: 331
<212> TYPE: PRT
<213> ORGANISM: Triticum sp.

<400> SEQUENCE: 34

Met Lys Thr Phe Leu Ile Leu Ser Leu Leu Ala Ile Val Ala Thr Thr
1               5                   10                  15
Ala Thr Thr Ala Val Arg Phe Pro Val Pro Gln Leu Gln Pro Gln Asn
                20                  25                  30
Pro Ser Gln Gln Gln Pro Gln Glu Gln Val Pro Leu Val Gln Gln Leu
                35                  40                  45
Gln Tyr Pro Gly Gln Gln Pro Phe Pro Pro Gln Gln Pro Tyr Pro
                50                  55                  60
Gln Pro Gln Pro Phe Pro Ser Gln Gln Pro Leu Pro Gln Pro Gln Pro
65                  70                  75                  80
Phe Leu Pro Gln Leu Pro Tyr Pro Gln Pro Gln Pro Phe Pro Pro Gln
                    85                  90                  95
Gln Pro Tyr Pro Gln Pro Gln Pro Gln Tyr Pro Gln Pro Gln Gln Pro
                100                 105                 110
Ile Ser Gln Gln Gln Ala Gln Gln Ala Gln Gln Gln Gln Gln Gln Gln
                115                 120                 125
Gln Gln Gln Gln Gln Gln Gln Gln Gln Gln Ile Leu Gln Gln Ile
                130                 135                 140
```

```
Leu Gln Gln Gln Gln Leu Ile Pro Cys Arg Asp Val Val Leu Gln Gln
145                 150                 155                 160

His Asn Ile Ala His Ala Ser Ser Gln Val Leu Gln Gln Ser Ser Tyr
            165                 170                 175

Gln Leu Leu Gln Gln Leu Cys Cys Gln Arg Leu Trp Gln Ile Pro Glu
            180                 185                 190

Gln Ser Arg Cys Gln Ala Ile His Asn Val Val His Ala Ile Ile Leu
        195                 200                 205

Gln Gln Gln Gln Gln Gln Gln Gln Gln Gln Gln Gln Gln Gln Gln Gln
210                 215                 220

Gln Gln Gln Gln Gln Gln Gln Gln Gln Gln Gln Gln Gln Gln Gln Gln
225                 230                 235                 240

Gln Gln Gln Gln Gln Gln Gln Gln Gln Gln Gln Gln Gln Pro Ser Ser
                245                 250                 255

Gln Val Ser Tyr Gln Gln Pro Gln Gln Gln Tyr Pro Ser Gly Gln Gly
            260                 265                 270

Ser Phe Gln Pro Ser Gln Asn Pro Gln Ala Gln Ala Ser Val Gln
            275                 280                 285

Pro Gln Gln Leu Pro Gln Phe Glu Glu Ile Arg Asn Leu Ala Arg Gln
290                 295                 300

Thr Leu Pro Ala Met Cys Asn Val Tyr Ile Pro Pro Tyr Cys Ser Thr
305                 310                 315                 320

Thr Ile Ala Pro Ser Gly Ile Phe Gly Thr Asn
                325                 330

<210> SEQ ID NO 35
<211> LENGTH: 439
<212> TYPE: PRT
<213> ORGANISM: Triticum sp.

<400> SEQUENCE: 35

Met Lys Thr Phe Ile Ile Phe Val Leu Leu Ala Met Ala Met Asn Ile
1               5                   10                  15

Ala Ser Ala Ser Arg Leu Leu Ser Pro Arg Gly Lys Glu Leu His Thr
            20                  25                  30

Pro Gln Glu Gln Phe Pro Gln Gln Gln Phe Pro Gln Pro Gln Gln
        35                  40                  45

Phe Pro Gln Gln Gln Ile Pro Gln Gln His Gln Ile Pro Gln Gln Pro
    50                  55                  60

Gln Gln Phe Pro Gln Gln Gln Phe Leu Gln Gln Gln Ile Pro
65                  70                  75                  80

Gln Gln Gln Ile Pro Gln Gln His Gln Ile Pro Gln Pro Gln Gln
                85                  90                  95

Phe Pro Gln Gln Gln Phe Pro Gln His Gln Ser Pro Gln Gln
            100                 105                 110

Gln Phe Pro Gln Gln Phe Pro Gln Lys Leu Pro Gln Gln Glu
        115                 120                 125

Phe Pro Gln Gln Gln Ile Ser Gln Gln Pro Gln Gln Leu Pro Gln Gln
    130                 135                 140

Gln Gln Ile Pro Gln Gln Pro Gln Gln Phe Leu Gln Gln Gln Phe
145                 150                 155                 160

Pro Gln Gln Gln Pro Pro Gln Gln His Gln Phe Pro Gln Gln Leu
                165                 170                 175

Pro Gln Gln Gln Ile Pro Gln Gln Gln Ile Pro Gln Gln Pro
            180                 185                 190
```

Gln Gln Ile Pro Gln Gln Gln Ile Pro Gln Gln Pro Gln Gln Phe
        195                 200                 205

Pro Gln Gln Gln Phe Pro Gln Gln Gln Phe Pro Gln Gln Gln Phe Pro
210                 215                 220

Gln Gln Glu Phe Pro Gln Gln Gln Phe Pro Gln Gln Gln Ile Ala
225                 230                 235                 240

Arg Gln Pro Gln Gln Leu Pro Gln Gln Gln Ile Pro Gln Gln Pro
                245                 250                 255

Gln Gln Phe Pro Gln Gln Gln Phe Pro Gln Gln Gln Ser Pro Gln
        260                 265                 270

Gln Gln Gln Phe Pro Gln Gln Phe Pro Gln Gln Gln Leu Pro
        275                 280                 285

Gln Lys Gln Phe Pro Gln Pro Gln Gln Ile Pro Gln Gln Gln Ile
        290                 295                 300

Pro Gln Gln Pro Gln Gln Phe Pro Gln Gln Gln Phe Pro Gln Gln Gln
305                 310                 315                 320

Gln Phe Pro Gln Gln Gln Glu Phe Pro Gln Gln Gln Phe Pro Gln Gln
                325                 330                 335

Gln Phe His Gln Gln Gln Leu Pro Gln Gln Gln Phe Pro Gln Gln Gln
        340                 345                 350

Phe Pro Gln Gln Gln Phe Pro Gln Gln Gln Phe Pro Gln Gln Gln
355                 360                 365

Gln Leu Thr Gln Gln Gln Phe Pro Arg Pro Gln Gln Ser Pro Glu Gln
370                 375                 380

Gln Gln Phe Pro Gln Gln Gln Phe Pro Gln Gln Pro Pro Gln Gln Phe
385                 390                 395                 400

Pro Gln Gln Gln Phe Pro Ile Pro Tyr Pro Pro Gln Gln Ser Glu Glu
                405                 410                 415

Pro Ser Pro Tyr Gln Gln Tyr Pro Gln Gln Pro Ser Gly Ser Asp
        420                 425                 430

Val Ile Ser Ile Ser Gly Leu
        435

<210> SEQ ID NO 36
<211> LENGTH: 1025
<212> TYPE: PRT
<213> ORGANISM: Triticum sp.

<400> SEQUENCE: 36

Met Ala Lys Arg Leu Val Leu Phe Val Ala Val Val Ala Leu Val
1               5                   10                  15

Ala Leu Thr Val Ala Glu Gly Glu Ala Ser Glu Gln Leu Gln Cys Glu
                20                  25                  30

Arg Glu Leu Gln Glu Leu Gln Glu Arg Glu Leu Lys Ala Cys Gln Gln
            35                  40                  45

Val Met Asp Gln Gln Leu Arg Asp Ile Ser Pro Glu Cys His Pro Val
        50                  55                  60

Val Val Ser Pro Val Ala Gly Gln Tyr Glu Gln Gln Ile Val Val Pro
65                  70                  75                  80

Pro Lys Gly Gly Ser Phe Tyr Pro Gly Glu Thr Thr Pro Gln Gln
                85                  90                  95

Leu Gln Gln Arg Ile Phe Trp Gly Ile Pro Ala Leu Leu Lys Arg Tyr
            100                 105                 110

Tyr Pro Ser Val Thr Ser Pro Gln Gln Val Ser Tyr Tyr Pro Gly Gln

```
            115                 120                 125
Ala Ser Pro Gln Arg Pro Gly Gln Gly Gln Pro Gly Gln Gly Gln
        130                 135                 140
Gln Ser Gly Gln Gly Gln Gly Tyr Tyr Pro Thr Ser Pro Gln Gln
145                 150                 155                 160
Pro Gly Gln Trp Gln Gln Pro Glu Gln Gly Gln Pro Gly Tyr Tyr Pro
                165                 170                 175
Thr Ser Pro Gln Gln Pro Gly Gln Leu Gln Gln Pro Ala Gln Gly Gln
            180                 185                 190
Gln Pro Gly Gln Gly Gln Gly Arg Gln Pro Gly Gln Gly Gln Pro
        195                 200                 205
Gly Tyr Tyr Pro Thr Ser Ser Gln Leu Gln Pro Gly Gln Leu Gln Gln
    210                 215                 220
Pro Ala Gln Gly Gln Gln Gly Gln Pro Gly Gln Gly Gln Gly
225                 230                 235                 240
Gln Gln Pro Gly Gln Gly Gln Pro Gly Gln Gly Gln Gly Gln
                245                 250                 255
Gln Pro Gly Gln Gly Gln Gln Pro Gly Gln Gly Gln Gly Gln Gln
            260                 265                 270
Leu Gly Gln Gly Gln Gly Tyr Tyr Pro Thr Ser Leu Gln Gln Ser
        275                 280                 285
Gly Gln Gly Gln Pro Gly Tyr Tyr Pro Thr Ser Leu Gln Gln Leu Gly
    290                 295                 300
Gln Gly Gln Ser Gly Tyr Tyr Pro Thr Ser Pro Gln Gln Pro Gly Gln
305                 310                 315                 320
Gly Gln Gln Pro Gly Gln Leu Gln Gln Pro Ala Gln Gly Gln Pro
                325                 330                 335
Glu Gln Gly Gln Gln Gly Gln Pro Gly Gln Gly Gln Gly Gln
            340                 345                 350
Gln Pro Gly Gln Gly Gln Gln Pro Gly Gln Gly Gln Pro Gly Tyr Tyr
        355                 360                 365
Pro Thr Ser Pro Gln Gln Ser Gly Gln Gly Gln Pro Gly Tyr Tyr Pro
370                 375                 380
Thr Ser Ser Gln Gln Pro Thr Gln Ser Gln Gln Pro Gly Gln Gly Gln
385                 390                 395                 400
Gln Gly Gln Gln Val Gly Gln Gln Gln Ala Gln Pro Gly Gln
                405                 410                 415
Gly Gln Gln Pro Gly Gln Gly Gln Pro Gly Tyr Tyr Pro Thr Ser Pro
            420                 425                 430
Leu Gln Ser Gly Gln Gly Gln Pro Gly Tyr Tyr Leu Thr Ser Pro Gln
        435                 440                 445
Gln Ser Gly Gln Gly Gln Gln Pro Gly Gln Leu Gln Gln Ser Ala Gln
    450                 455                 460
Gly Gln Lys Gly Gln Gln Pro Gly Gln Gly Gln Pro Gly Gln Gly
465                 470                 475                 480
Gln Gln Gly Gln Gln Pro Gly Gln Gly Gln Gln Gly Gln Pro Gly
                485                 490                 495
Gln Gly Gln Pro Gly Tyr Tyr Pro Thr Ser Pro Gln Gln Ser Gly Gln
            500                 505                 510
Gly Gln Gln Pro Gly Gln Trp Gln Gln Pro Gly Gln Gly Gln Pro Gly
        515                 520                 525
Tyr Tyr Pro Thr Ser Pro Leu Gln Pro Gly Gln Gly Gln Pro Gly Tyr
    530                 535                 540
```

-continued

```
Asp Pro Thr Ser Pro Gln Gln Pro Gly Gln Gly Gln Pro Gly Gln
545                 550                 555                 560

Leu Gln Gln Pro Ala Gln Gly Gln Gln Gly Gln Gln Leu Ala Gln Gly
                565                 570                 575

Gln Gln Gly Gln Gln Pro Ala Gln Val Gln Gly Gln Gln Pro Ala
        580                 585                 590

Gln Gly Gln Gln Gly Gln Gln Leu Gly Gln Gln Gly Gln Gln Gln
            595                 600                 605

Pro Gly Gln Gly Gln Gln Pro Ala Gln Gly Gln Gln Gly Gln Pro
    610                 615                 620

Gly Gln Gly Gln Gln Gly Gln Gln Pro Gly Gln Gly Gln Pro Gly
625                 630                 635                 640

Gln Gly Gln Pro Trp Tyr Tyr Pro Thr Ser Pro Gln Glu Ser Gly Gln
                645                 650                 655

Gly Gln Gln Pro Gly Gln Trp Gln Gln Pro Gly Gln Trp Gln Gln Pro
                660                 665                 670

Gly Gln Gly Gln Gln Gly Gln Gln Pro Gly Gln Gly Gln Pro Gly Tyr
        675                 680                 685

Tyr Pro Thr Ser Pro Gln Ser Gly Gln Gly Gln Gln Pro Gly Gln
    690                 695                 700

Trp Gln Gln Pro Gly Gln Gly Gln Pro Gly Tyr Tyr Pro Thr Ser Pro
705                 710                 715                 720

Leu Gln Pro Gly Gln Gly Gln Pro Gly Tyr Asp Pro Thr Ser Pro Gln
                725                 730                 735

Gln Pro Gly Gln Gly Gln Gln Pro Gly Gln Leu Gln Gln Pro Ala Gln
                740                 745                 750

Gly Gln Gln Gly Gln Gln Leu Ala Gln Gly Gln Gln Gly Gln Gln Pro
            755                 760                 765

Ala Gln Val Gln Gln Gly Gln Gln Pro Ala Gln Gly Gln Gln Gly Gln
        770                 775                 780

Gln Leu Gly Gln Gly Gln Gln Gly Gln Gln Pro Gly Gln Gly Gln Gln
785                 790                 795                 800

Pro Ala Gln Gly Gln Gln Gly Gln Gln Pro Gly Gln Gly Gln Gln Gly
                805                 810                 815

Gln Gln Pro Gly Gln Gly Gln Gln Pro Gly Gln Gly Gln Pro Trp Tyr
            820                 825                 830

Tyr Pro Thr Ser Pro Gln Glu Ser Gly Gln Gly Gln Gln Pro Gly Gln
        835                 840                 845

Trp Gln Gln Pro Gly Gln Trp Gln Gln Pro Gly Gln Gly Gln Pro Gly
    850                 855                 860

Tyr Tyr Leu Thr Ser Pro Leu Gln Leu Gly Gln Gln Gln Gly Tyr
865                 870                 875                 880

Tyr Pro Thr Ser Leu Gln Gln Pro Gly Gln Gly Gln Pro Gly Gln
                885                 890                 895

Trp Gln Gln Ser Gly Gln Gly Gln His Gly Tyr Tyr Pro Thr Ser Pro
                900                 905                 910

Gln Leu Ser Gly Gln Gly Gln Arg Pro Gly Gln Trp Leu Gln Pro Gly
            915                 920                 925

Gln Gly Gln Gln Gly Tyr Tyr Pro Thr Ser Pro Gln Ser Gly Gln
        930                 935                 940

Gly Gln Gln Leu Gly Gln Trp Leu Gln Pro Gly Gln Gly Gln Gln Gly
945                 950                 955                 960
```

-continued

```
Tyr Tyr Pro Thr Ser Leu Gln Gln Thr Gly Gln Gln Gln Ser Gly
                965                 970                 975

Gln Gly Gln Gln Gly Tyr Tyr Ser Ser Tyr His Val Ser Val Glu His
        980                 985                 990

Gln Ala Ala Ser Leu Lys Val Ala Lys Ala Gln Gln Leu Ala Ala Gln
        995                 1000                1005

Leu Pro Ala Met Cys Arg Leu Glu Gly Gly Asp Ala Leu Ser Ala
        1010                1015                1020

Ser Gln
    1025

<210> SEQ ID NO 37
<211> LENGTH: 392
<212> TYPE: PRT
<213> ORGANISM: Triticum sp.

<400> SEQUENCE: 37

Met Lys Thr Phe Leu Ile Phe Ala Leu Leu Ala Val Ala Ala Thr Ser
1               5                   10                  15

Ala Ile Ala Gln Met Glu Asn Ser His Ile Pro Gly Leu Glu Arg Pro
            20                  25                  30

Ser Gln Gln Gln Pro Leu Pro Pro Gln Gln Thr Leu Ser His His Gln
        35                  40                  45

Gln Gln Gln Pro Ile Gln Gln Pro His Gln Phe Pro Gln Gln Gln
    50                  55                  60

Pro Cys Ser Gln Gln Gln Pro Pro Leu Ser Gln Gln Gln Gln
65                  70                  75                  80

Pro Pro Phe Ser Gln Gln Gln Pro Pro Phe Ser Gln Gln Gln Gln
                85                  90                  95

Pro Val Leu Pro Gln Gln Pro Ser Phe Ser Gln Gln Leu Pro Pro
            100                 105                 110

Phe Ser Gln Gln Gln Pro Pro Phe Ser Gln Gln Gln Pro Val
        115                 120                 125

Leu Pro Gln Gln Pro Ser Phe Ser Gln Gln Leu Pro Pro Phe Ser
        130                 135                 140

Gln Gln Leu Pro Pro Phe Leu Gln Gln Gln Pro Val Leu Pro Gln
145                 150                 155                 160

Gln Pro Pro Phe Ser Gln Gln Leu Pro Pro Phe Ser Gln Gln Leu
                165                 170                 175

Pro Pro Phe Ser Gln Gln Gln Pro Val Leu Pro Gln Gln Pro Pro
            180                 185                 190

Phe Ser Gln Gln Gln Gln Pro Ile Leu Pro Gln Gln Pro Pro Phe
        195                 200                 205

Ser Gln Gln Gln Pro Val Leu Leu Gln Gln Ile Pro Phe Val
    210                 215                 220

His Pro Ser Ile Leu Gln Gln Leu Asn Pro Cys Lys Val Phe Leu Gln
225                 230                 235                 240

Gln Gln Cys Ser Pro Val Ala Met Pro Gln Ser Leu Ala Arg Ser Gln
                245                 250                 255

Met Leu Gln Gln Arg Ser Cys His Val Met Gln Gln Cys Cys Gln
            260                 265                 270

Gln Leu Pro Gln Ile Pro Gln Gln Ser Arg Tyr Glu Ala Ile Arg Ala
        275                 280                 285

Ile Val Tyr Ser Ile Ile Leu Gln Glu Gln Gln Gln Val Gln Gly Ser
    290                 295                 300
```

```
Ile Gln Thr Gln Gln Gln Pro Gln Leu Gly Gln Cys Val Ser
305                 310                 315                 320

Gln Pro Gln Gln Leu Gln Gln Leu Gly Gln Pro Gln Gln
            325                 330                 335

Gln Gln Leu Ala Gln Gly Thr Phe Leu Gln Pro His Gln Ile Ala Gln
            340                 345                 350

Leu Glu Val Met Thr Ser Ile Ala Leu Arg Thr Leu Pro Thr Met Cys
                355                 360                 365

Asn Val Asn Val Pro Leu Tyr Arg Thr Thr Arg Val Pro Phe Gly
        370                 375                 380

Val Gly Thr Gly Val Gly Gly Tyr
385                 390

<210> SEQ ID NO 38
<211> LENGTH: 1912
<212> TYPE: PRT
<213> ORGANISM: Gallus gallus

<400> SEQUENCE: 38

Met Arg Gly Leu Ile Ser Ala Leu Val Leu Thr Leu Val Gly Ser Gln
1               5                   10                  15

His Leu Asn Tyr Gln Pro Asp Phe Gly Glu Asn Lys Val Tyr Thr Tyr
            20                  25                  30

Asn Tyr Glu Ser Ile Leu Phe Ser Gly Ile Pro Glu Lys Gly Leu Ala
        35                  40                  45

Arg Thr Gly Ile Arg Ile Arg Ser Glu Val Glu Ile Ser Gly Ile Gly
    50                  55                  60

Pro Lys Leu Cys Leu Ile Arg Ile His Ser Ile Glu Ala Ala Glu Tyr
65                  70                  75                  80

Asn Gly Ile Trp Pro Thr Ser Ser Phe Ser Arg Ser Leu Lys Leu Thr
                85                  90                  95

Gln Ala Leu Thr Gly Gln Leu Ser Ile Pro Ile Lys Phe Glu Tyr Ser
            100                 105                 110

Asn Gly His Val Gly Asn Leu Met Ala Pro Asp Ser Val Ser Asp Asp
        115                 120                 125

Gly Leu Asn Ile Tyr Arg Gly Ile Leu Asn Ile Leu Glu Leu Ser Leu
    130                 135                 140

Lys Lys Met Gln His Ser Tyr Ser Ile Gln Glu Ala Gly Ile Gly Gly
145                 150                 155                 160

Ile Cys Asn Thr Thr Tyr Ala Ile Gln Glu Asn Lys Lys Ala Asn Leu
                165                 170                 175

Val Asp Val Thr Lys Ser Lys Asp Leu Asn Ser Cys Glu Glu Lys Val
            180                 185                 190

Gln Val Val Thr Gly Ser Ala Tyr Thr Gln Pro Cys Gln Thr Cys Gln
        195                 200                 205

Gln Arg Asn Lys Asn Ser Arg Ala Thr Ala Thr Tyr Asn Tyr Lys Ile
    210                 215                 220

Lys Tyr Thr His Asn Glu Ala Val Ile Thr Gln Ala Glu Val Glu Glu
225                 230                 235                 240

Val His Gln Phe Thr Pro Phe His Glu Ile Thr Gly Gly Asn Ala Ile
                245                 250                 255

Val Glu Ala Arg Gln Lys Leu Ala Leu Ile Glu Val Gln Lys Gln Val
            260                 265                 270

Ala Glu Val Pro Pro Lys Glu Phe Gln Lys Arg Gly Ser Leu Gln Tyr
```

```
                275                 280                 285
Gln Phe Gly Ser Glu Leu Leu Gln Leu Pro Val His Leu Phe Lys Ile
            290                 295                 300
Lys Asp Val Glu Arg Gln Ile Glu Glu Arg Leu Gln Asp Leu Val Glu
305                 310                 315                 320
Thr Thr Tyr Glu Gln Leu Pro Ser Asp Ala Pro Ala Lys Ala Leu Lys
                325                 330                 335
Leu Met His Leu Leu Arg Ala Ala Asn Glu Glu Asn Tyr Glu Ser Val
            340                 345                 350
Trp Lys Gln Phe Ser Ser Arg Pro Ala Tyr Arg Arg Tyr Leu Leu Asp
                355                 360                 365
Leu Leu Pro Ala Ala Ala Ser His Arg Ser Leu Arg Phe Leu Arg His
            370                 375                 380
Lys Met Glu Arg Gln Glu Leu Thr Asn Trp Glu Ile Ala Gln Thr Val
385                 390                 395                 400
Leu Val Ala Leu His Ser Ser Pro Thr Gln Glu Val Met Glu Glu
                405                 410                 415
Ala Thr Leu Ile Val Lys Lys His Cys Pro Arg Ser Ser Val Leu
            420                 425                 430
Arg Lys Val Cys Leu Leu Ser Tyr Ala Ser Leu Cys His Lys Arg Cys
            435                 440                 445
Ser Ser Pro Tyr Ser Cys Ser Glu Cys Leu Gln Val Phe His Val Phe
        450                 455                 460
Ala Gly Glu Ala Leu Gly Lys Ser Asn Ile Glu Glu Val Leu Leu Ala
465                 470                 475                 480
Leu Lys Ala Leu Gly Asn Val His Pro Ala Ser Ile Lys His Ile
            485                 490                 495
Lys Lys Phe Leu Pro Gly Tyr Ala Ala Gly Ala Ser Glu Leu Pro Leu
            500                 505                 510
Lys Val His Glu Thr Ala Val Met Ala Leu Lys Ser Ile Gly Met Arg
        515                 520                 525
Asp Pro Gln Met Val Gln Ala Ile Thr Leu Glu Ile Phe Leu Asn His
    530                 535                 540
Lys Ile His Pro Arg Ile Arg Met Leu Ala Ala Val Val Leu Leu Glu
545                 550                 555                 560
Thr Lys Pro Gly Leu Pro Ile Leu Met Ile Leu Val Asp Ala Val Leu
                565                 570                 575
Lys Glu Pro Ser Met Gln Val Ala Ser Phe Ile Tyr Ser His Leu Arg
            580                 585                 590
Ala Leu Gly Arg Ser Thr Ala Pro Asp Leu Gln Met Met Ala Ser Ala
        595                 600                 605
Cys Arg Met Ala Val Arg Ala Leu Ser Pro Lys Phe Asp Arg Ser Gly
    610                 615                 620
Tyr Gln Phe Ser Lys Val Phe Arg Phe Ser Met Phe Lys Glu Phe Leu
625                 630                 635                 640
Met Ser Gly Leu Ala Ala Lys Tyr Phe Val Leu Asn Asn Ala Gly Ser
                645                 650                 655
Leu Ile Pro Thr Met Ala Val Ser Gln Leu Arg Thr His Phe Leu Gly
            660                 665                 670
Arg Val Ala Asp Pro Ile Glu Val Gly Ile Ala Ala Glu Gly Leu Gln
        675                 680                 685
Glu Met Phe Val Arg Gly Tyr Ser Pro Asp Lys Asp Trp Glu Thr Asn
    690                 695                 700
```

Tyr Asp Phe Arg Glu Ile Leu Lys Lys Leu Ser Asp Trp Lys Ala Leu
705                 710                 715                 720

Pro Arg Asp Lys Pro Phe Ala Ser Gly Tyr Leu Lys Met Phe Gly Gln
            725                 730                 735

Glu Leu Leu Phe Gly Arg Leu Asp Lys Asp Thr Leu Gln Asn Val Leu
                740                 745                 750

Gln Val Trp Tyr Gly Pro Asp Glu Lys Ile Pro Ser Ile Arg Arg Leu
            755                 760                 765

Ile Ser Ser Leu Gln Thr Gly Ile Gly Arg Gln Trp Thr Lys Ala Leu
770                 775                 780

Leu Leu Ser Glu Ile Arg Cys Ile Val Pro Thr Cys Val Gly Phe Pro
785                 790                 795                 800

Met Glu Thr Ser Phe Tyr Tyr Ser Ser Val Thr Lys Val Ala Gly Asn
                805                 810                 815

Val Gln Ala Gln Ile Thr Pro Ser Pro Arg Ser Asp Phe Arg Leu Thr
            820                 825                 830

Glu Leu Leu Asn Ser Asn Val Arg Leu Arg Ser Lys Met Ser Leu Ser
            835                 840                 845

Met Ala Lys His Met Thr Phe Val Ile Gly Ile Asn Thr Asn Met Ile
850                 855                 860

Gln Ala Gly Leu Glu Ala His Thr Lys Val Asn Ala His Val Pro Val
865                 870                 875                 880

Asn Val Val Ala Thr Ile Gln Met Lys Glu Lys Ser Ile Lys Ala Glu
                885                 890                 895

Ile Pro Pro Cys Lys Glu Glu Thr Asn Leu Ile Ile Val Ser Ser Lys
            900                 905                 910

Thr Phe Ala Val Thr Arg Asn Ile Glu Asp Leu Ala Ala Ser Lys Met
            915                 920                 925

Thr Pro Val Leu Leu Pro Glu Ala Val Pro Asp Ile Met Lys Met Ser
930                 935                 940

Phe Asp Ser Asp Ser Ala Ser Gly Glu Thr Asp Asn Ile Arg Asp Arg
945                 950                 955                 960

Gln Ser Val Glu Asp Val Ser Gly Asn Ser Phe Ser Phe Gly His
                965                 970                 975

Pro Ser Ser Gly Lys Glu Pro Phe Ile Gln Ser Met Cys Ser Asn Ala
            980                 985                 990

Ser Thr Phe Gly Val Gln Val Cys Ile Glu Lys Lys Ser Val His Ala
        995                 1000                1005

Ala Phe Ile Arg Asn Val Pro Leu Tyr Asn Ala Ile Gly Glu His
    1010                1015                1020

Ala Leu Arg Met Ser Phe Lys Pro Val Tyr Ser Asp Val Pro Ile
    1025                1030                1035

Glu Lys Ile Gln Val Thr Ile Gln Ala Gly Asp Gln Ala Pro Thr
    1040                1045                1050

Lys Met Val Arg Leu Val Thr Phe Glu Asp Pro Glu Arg Gln Glu
    1055                1060                1065

Ser Ser Arg Lys Glu Val Met Lys Arg Val Lys Lys Ile Leu Asp
    1070                1075                1080

Asp Thr Asp Asn Gln Ala Thr Arg Asn Ser Arg Ser Ser Ser Ser
    1085                1090                1095

Ser Ala Ser Ser Ile Ser Glu Ser Ser Glu Ser Thr Thr Ser Thr
    1100                1105                1110

```
Pro Ser Ser Ser Asp Ser Asp Asn Arg Ala Ser Gln Gly Asp Pro
    1115            1120                1125

Gln Ile Asn Leu Lys Ser Arg Gln Ser Lys Ala Asn Glu Lys Lys
    1130            1135                1140

Phe Tyr Pro Phe Gly Asp Ser Ser Ser Gly Ser Ser Ser Ser
    1145            1150                1155

Ser Ser Ser Ser Ser Ser Ser Ser Asp Ser Ser Ser Ser
    1160            1165                1170

Arg Ser Ser Ser Ser Asp Ser Ser Ser Ser Ser Ser Ser
    1175            1180                1185

Ser Ser Ser Ser Ser Ser Lys Ser Lys Ser Ser Ser Arg Ser Ser
    1190            1195                1200

Lys Ser Asn Arg Ser Ser Ser Ser Asn Ser Lys Asp Ser Ser
    1205            1210                1215

Ser Ser Ser Ser Lys Ser Asn Ser Lys Gly Ser Ser Ser Ser Ser
    1220            1225                1230

Ser Lys Ala Ser Gly Thr Arg Gln Lys Ala Lys Lys Gln Ser Lys
    1235            1240                1245

Thr Thr Ser Phe Pro His Ala Ser Ala Ala Glu Gly Glu Arg Ser
    1250            1255                1260

Val His Glu Gln Lys Gln Glu Thr Gln Ser Ser Ser Ser Ser Ser
    1265            1270                1275

Ser Arg Ala Ser Ser Asn Ser Arg Ser Thr Ser Ser Ser Thr Ser
    1280            1285                1290

Ser Ser Ser Glu Ser Ser Gly Val Ser His Arg Gln Trp Lys Gln
    1295            1300                1305

Asp Arg Glu Ala Glu Thr Lys Arg Val Lys Ser Gln Phe Asn Ser
    1310            1315                1320

His Ser Ser Tyr Asp Ile Pro Asn Glu Trp Glu Thr Tyr Leu Pro
    1325            1330                1335

Lys Val Tyr Arg Leu Arg Phe Arg Ser Ala His Thr His Trp His
    1340            1345                1350

Ser Gly His Arg Thr Ser Ser Ser Ser Ser Ser Ser Ser Ser Glu
    1355            1360                1365

Ser Gly Ser Ser His Ser Asn Ser Ser Ser Ser Asp Ser Ser Ser
    1370            1375                1380

Arg Arg Ser His Met Ser Asp Ser Ser Ser Ser Ser Ser His
    1385            1390                1395

Arg His Gly Glu Lys Ala Ala His Ser Ser Arg Arg Ser Pro Thr
    1400            1405                1410

Ser Arg Ala Ala Ser Ala His His Arg Pro Gly Ser Ser Leu Thr
    1415            1420                1425

Arg Glu Arg Asn Phe Leu Gly Asp Val Ile Pro Pro Gly Ile Thr
    1430            1435                1440

Ile Val Ala Gln Ala Val Arg Ser Asp Asn Arg Asn Gln Gly Tyr
    1445            1450                1455

Gln Ala Thr Ala Tyr Val Arg Ser Asp Ala Ala Lys Val Asp Val
    1460            1465                1470

Gln Leu Val Val Val Gln Leu Ala Glu Thr Asn Trp Lys Ala Cys
    1475            1480                1485

Ala Asp Ala Val Ile Leu Pro Leu Lys Ala Gln Ala Arg Met Arg
    1490            1495                1500

Trp Gly Lys Glu Cys Arg Asp Tyr Arg Ile Ala Ala Leu Ala Thr
```

-continued

```
            1505                1510                1515
Thr Gly Gln Met Ala Arg Lys Leu Ala Val Gln Leu Lys Val Gln
    1520                1525                1530
Trp Gly Ile Ile Pro Ser Trp Ile Lys Lys Thr Ser Thr Ala Leu
    1535                1540                1545
Met Arg Tyr Val Pro Gly Val Ala Leu Val Leu Gly Phe Ser Glu
    1550                1555                1560
Ala His Gln Arg Asn Pro Ser Arg Glu Leu Ile Val Arg Ala Val
    1565                1570                1575
Ala Thr Ser Pro Arg Ser Ile Asp Thr Val Ile Lys Val Pro Gly
    1580                1585                1590
Val Thr Leu Tyr Tyr Gln Gly Leu Arg Val Pro Phe Thr Leu Ala
    1595                1600                1605
Leu Gly Ala Ser Ser Ser Tyr Glu Thr Arg Asp Ile Thr Ala
    1610                1615                1620
Trp Asn Phe Leu Pro Glu Ile Ala Ser Gln Ile Ala Gln Glu Asp
    1625                1630                1635
Gln Ser Thr Cys Glu Val Ser Lys Gly Asp Phe Lys Thr Phe Asp
    1640                1645                1650
Arg Met Ser Phe Thr Cys Ser Phe Asn Lys Ser Cys Asn Val Val
    1655                1660                1665
Val Ala Gln Asp Cys Thr Glu His Pro Lys Phe Ile Ile Thr Thr
    1670                1675                1680
Arg Lys Val Asp His Gln Ser Leu Ser Arg Glu Val His Ile Asn
    1685                1690                1695
Thr Ser Ser Ala Asn Ile Thr Ile Cys Pro Ala Ala Asp Ser Ser
    1700                1705                1710
Leu Leu Val Thr Cys Asn Lys Glu Ser Val Leu Ser Asp Ser Gly
    1715                1720                1725
Val Ser Glu Tyr Glu Lys Asp Asn Ile Lys Ile Tyr Lys Asn Gly
    1730                1735                1740
Lys Thr Val Ile Val Glu Ala Pro Ile His Gly Leu Lys Asn Val
    1745                1750                1755
Asn Phe Asp Gly Glu Ile Leu Lys Val Thr Val Ala Ser Trp Met
    1760                1765                1770
Arg Gly Lys Thr Cys Gly Val Cys Gly Asn Asn Asp Arg Glu Lys
    1775                1780                1785
His Asn Glu Leu Leu Met Pro Asn His Lys Leu Ala His Ser Cys
    1790                1795                1800
Ser Ala Phe Val His Ser Trp Val Leu Leu Glu Glu Thr Cys Ser
    1805                1810                1815
Gly Gly Cys Lys Leu Gln Arg Arg Tyr Val Lys Leu Asn Arg Asn
    1820                1825                1830
Pro Thr Ile Asp Gly Glu Glu Ser Thr Cys Tyr Ser Val Asp Pro
    1835                1840                1845
Val Leu Lys Cys Met Lys Asp Cys Thr Pro Ile Glu Lys Thr Ser
    1850                1855                1860
Val Lys Val Gly Phe His Cys Phe Pro Lys Ala Thr Ala Val Ser
    1865                1870                1875
Leu Leu Glu Trp Gln Arg Ser Ser Asp Lys Lys Ser Ala Ser Glu
    1880                1885                1890
Asp Val Val Glu Ser Val Asp Ala Asp Ile Asp Cys Thr Cys Thr
    1895                1900                1905
```

```
Gly Asp Cys Ser
        1910

<210> SEQ ID NO 39
<211> LENGTH: 1850
<212> TYPE: PRT
<213> ORGANISM: Gallus gallus

<400> SEQUENCE: 39

Met Arg Gly Ile Ile Leu Ala Leu Val Leu Thr Leu Val Gly Ser Gln
1               5                   10                  15

Lys Phe Asp Ile Asp Pro Gly Phe Asn Ser Arg Arg Ser Tyr Leu Tyr
            20                  25                  30

Asn Tyr Glu Gly Ser Met Leu Asn Gly Leu Gln Asp Arg Ser Leu Gly
        35                  40                  45

Lys Ala Gly Val Arg Leu Ser Ser Lys Leu Glu Ile Ser Gly Leu Pro
    50                  55                  60

Glu Asn Ala Tyr Leu Leu Lys Val Arg Ser Pro Gln Val Glu Glu Tyr
65                  70                  75                  80

Asn Gly Val Trp Pro Arg Asp Pro Phe Thr Arg Ser Ser Lys Ile Thr
                85                  90                  95

Gln Val Ile Ser Ser Cys Phe Thr Arg Leu Phe Lys Phe Glu Tyr Ser
            100                 105                 110

Ser Gly Arg Ile Gly Asn Ile Tyr Ala Pro Glu Asp Cys Pro Asp Leu
        115                 120                 125

Cys Val Asn Ile Val Arg Gly Ile Leu Asn Met Phe Gln Met Thr Ile
    130                 135                 140

Lys Lys Ser Gln Asn Val Tyr Glu Leu Gln Glu Ala Gly Ile Gly Gly
145                 150                 155                 160

Ile Cys His Ala Arg Tyr Val Ile Gln Glu Asp Arg Lys Asn Ser Arg
                165                 170                 175

Ile Tyr Val Thr Arg Thr Val Asp Leu Asn Asn Cys Gln Glu Lys Val
            180                 185                 190

Gln Lys Ser Ile Gly Met Ala Tyr Ile Tyr Pro Cys Pro Val Asp Val
        195                 200                 205

Met Lys Glu Arg Leu Thr Lys Gly Thr Thr Ala Phe Ser Tyr Lys Leu
    210                 215                 220

Lys Gln Ser Asp Ser Gly Thr Leu Ile Thr Asp Val Ser Ser Arg Gln
225                 230                 235                 240

Val Tyr Gln Ile Ser Pro Phe Asn Glu Pro Thr Gly Val Ala Val Met
                245                 250                 255

Glu Ala Arg Gln Gln Leu Thr Leu Val Glu Val Arg Ser Glu Arg Gly
            260                 265                 270

Ser Ala Pro Asp Val Pro Met Gln Asn Tyr Gly Ser Leu Arg Tyr Arg
        275                 280                 285

Phe Pro Ala Val Leu Pro Gln Met Pro Leu Gln Leu Ile Lys Thr Lys
    290                 295                 300

Asn Pro Glu Gln Arg Ile Val Glu Thr Leu Gln His Ile Val Leu Asn
305                 310                 315                 320

Asn Gln Gln Asp Phe His Asp Val Ser Tyr Arg Phe Leu Glu Val
                325                 330                 335

Val Gln Leu Cys Arg Ile Ala Asn Ala Asp Asn Leu Glu Ser Ile Trp
            340                 345                 350

Arg Gln Val Ser Asp Lys Pro Arg Tyr Arg Arg Trp Leu Leu Ser Ala
```

```
              355                 360                 365
Val Ser Ala Ser Gly Thr Thr Glu Thr Leu Lys Phe Leu Lys Asn Arg
            370                 375                 380
Ile Arg Asn Asp Asp Leu Asn Tyr Ile Gln Thr Leu Leu Thr Val Ser
385                 390                 395                 400
Leu Thr Leu His Leu Leu Gln Ala Asp Glu His Thr Leu Pro Ile Ala
                405                 410                 415
Ala Asp Leu Met Thr Ser Ser Arg Ile Gln Lys Asn Pro Val Leu Gln
            420                 425                 430
Gln Val Ala Cys Leu Gly Tyr Ser Val Val Asn Arg Tyr Cys Ser
                435                 440                 445
Gln Thr Ser Ala Cys Pro Lys Glu Ala Leu Gln Pro Ile His Asp Leu
            450                 455                 460
Ala Asp Glu Ala Ile Ser Arg Gly Arg Glu Asp Lys Met Lys Leu Ala
465                 470                 475                 480
Leu Lys Cys Ile Gly Asn Met Gly Glu Pro Ala Ser Leu Lys Arg Ile
                485                 490                 495
Leu Lys Phe Leu Pro Ile Ser Ser Ser Ala Ala Asp Ile Pro Val
            500                 505                 510
His Ile Gln Ile Asp Ala Ile Thr Ala Leu Lys Lys Ile Ala Trp Lys
                515                 520                 525
Asp Pro Lys Thr Val Gln Gly Tyr Leu Ile Gln Ile Leu Ala Asp Gln
            530                 535                 540
Ser Leu Pro Pro Glu Val Arg Met Met Ala Cys Ala Val Ile Phe Glu
545                 550                 555                 560
Thr Arg Pro Ala Leu Ala Leu Ile Thr Thr Ile Ala Asn Val Ala Met
                565                 570                 575
Lys Glu Ser Asn Met Gln Val Ala Ser Phe Val Tyr Ser His Met Lys
            580                 585                 590
Ser Leu Ser Lys Ser Arg Leu Pro Phe Met Tyr Asn Ile Ser Ser Ala
                595                 600                 605
Cys Asn Ile Ala Leu Lys Leu Leu Ser Pro Lys Leu Asp Ser Met Ser
            610                 615                 620
Tyr Arg Tyr Ser Lys Val Ile Arg Ala Asp Thr Tyr Phe Asp Asn Tyr
625                 630                 635                 640
Arg Val Gly Ala Thr Gly Glu Ile Phe Val Asn Ser Pro Arg Thr
                645                 650                 655
Met Phe Pro Ser Ala Ile Ile Ser Lys Leu Met Ala Asn Ser Ala Gly
            660                 665                 670
Ser Val Ala Asp Leu Val Glu Val Gly Ile Arg Val Glu Gly Leu Ala
                675                 680                 685
Asp Val Ile Met Lys Arg Asn Ile Pro Phe Ala Glu Tyr Pro Thr Tyr
            690                 695                 700
Lys Gln Ile Lys Glu Leu Gly Lys Ala Leu Gln Gly Trp Lys Glu Leu
705                 710                 715                 720
Pro Thr Glu Thr Pro Leu Val Ser Ala Tyr Leu Lys Ile Leu Gly Gln
                725                 730                 735
Glu Val Ala Phe Ile Asn Ile Asn Lys Glu Leu Leu Gln Gln Val Met
                740                 745                 750
Lys Thr Val Val Glu Pro Ala Asp Arg Asn Ala Ala Ile Lys Arg Ile
            755                 760                 765
Ala Asn Gln Ile Arg Asn Ser Ile Ala Gly Gln Trp Thr Gln Pro Val
            770                 775                 780
```

```
Trp Met Gly Glu Leu Arg Tyr Val Pro Ser Cys Leu Gly Leu Pro
785                 790                 795                 800

Leu Glu Tyr Gly Ser Tyr Thr Thr Ala Leu Ala Arg Ala Ala Val Ser
            805                 810                 815

Val Glu Gly Lys Met Thr Pro Pro Leu Thr Gly Asp Phe Arg Leu Ser
            820                 825                 830

Gln Leu Leu Glu Ser Thr Met Gln Ile Arg Ser Asp Leu Lys Pro Ser
            835                 840                 845

Leu Tyr Val His Thr Val Ala Thr Met Gly Val Asn Thr Glu Tyr Phe
    850                 855                 860

Gln His Ala Val Glu Ile Gln Gly Glu Val Gln Thr Arg Met Pro Met
865                 870                 875                 880

Lys Phe Asp Ala Lys Ile Asp Val Lys Leu Lys Asn Leu Lys Ile Glu
            885                 890                 895

Thr Asn Pro Cys Arg Glu Glu Thr Glu Ile Val Val Gly Arg His Lys
            900                 905                 910

Ala Phe Ala Val Ser Arg Asn Ile Gly Glu Leu Gly Val Glu Lys Arg
            915                 920                 925

Thr Ser Ile Leu Pro Glu Asp Ala Pro Leu Asp Val Thr Glu Glu Pro
    930                 935                 940

Phe Gln Thr Ser Glu Arg Ala Ser Arg Glu His Phe Ala Met Gln Gly
945                 950                 955                 960

Pro Asp Ser Met Pro Arg Lys Gln Ser His Ser Ser Arg Glu Asp Leu
            965                 970                 975

Arg Arg Ser Thr Gly Lys Arg Ala His Lys Arg Asp Ile Cys Leu Lys
            980                 985                 990

Met His His Ile Gly Cys Gln Leu  Cys Phe Ser Arg Arg  Ser Arg Asp
            995                 1000                 1005

Ala Ser  Phe Ile Gln Asn Thr  Tyr Leu His Lys Leu  Ile Gly Glu
    1010                 1015                 1020

His Glu  Ala Lys Ile Val Leu  Met Pro Val His Thr  Asp Ala Asp
    1025                 1030                 1035

Ile Asp  Lys Ile Gln Leu Glu  Ile Gln Ala Gly Ser  Arg Ala Ala
    1040                 1045                 1050

Ala Arg  Ile Ile Thr Glu Val  Asn Pro Glu Ser Glu  Glu Glu Asp
    1055                 1060                 1065

Glu Ser  Ser Pro Tyr Glu Asp  Ile Gln Ala Lys Leu  Lys Arg Ile
    1070                 1075                 1080

Leu Gly  Ile Asp Ser Met Phe  Lys Val Ala Asn Lys  Thr Arg His
    1085                 1090                 1095

Pro Lys  Asn Arg Pro Ser Lys  Lys Gly Asn Thr Val  Leu Ala Glu
    1100                 1105                 1110

Phe Gly  Thr Glu Pro Asp Ala  Lys Thr Ser Ser Ser  Ser Ser Ser
    1115                 1120                 1125

Ala Ser  Ser Thr Ala Thr Ser  Ser Ser Ser Ser Ser  Ala Ser Ser
    1130                 1135                 1140

Pro Asn  Arg Lys Lys Pro Met  Asp Glu Glu Glu Asn  Asp Gln Val
    1145                 1150                 1155

Lys Gln  Ala Arg Asn Lys Asp  Ala Ser Ser Ser Ser  Arg Ser Ser
    1160                 1165                 1170

Lys Ser  Ser Asn Ser Ser Lys  Arg Ser Ser Ser Lys  Ser Ser Asn
    1175                 1180                 1185
```

-continued

| | | | | | | | | | | | |
|---|---|---|---|---|---|---|---|---|---|---|---|
| Ser | Ser | Lys | Arg | Ser | Ser | Ser | Ser | Ser | Ser | Ser | Ser | Ser |
| | 1190 | | | | 1195 | | | | 1200 | | |
| Ser | Arg | Ser | Ser | Ser | Ser | Ser | Ser | Ser | Ser | Ser | Asn | Ser | Lys |
| | 1205 | | | | | 1210 | | | | 1215 | | |
| Ser | Ser | Ser | Ser | Ser | Ser | Lys | Ser | Ser | Ser | Ser | Ser | Arg | Ser |
| | 1220 | | | | | 1225 | | | | 1230 | | |
| Arg | Ser | Ser | Ser | Lys | Ser | Ser | Ser | Ser | Ser | Ser | Ser | Ser | Ser |
| | 1235 | | | | | 1240 | | | | 1245 | | |
| Ser | Ser | Ser | Ser | Lys | Ser | Ser | Ser | Ser | Arg | Ser | Ser | Ser | Ser |
| | 1250 | | | | | 1255 | | | | 1260 | | |
| Ser | Lys | Ser | Ser | Ser | His | His | Ser | His | Ser | His | His | Ser | Gly | His |
| | 1265 | | | | | 1270 | | | | 1275 | | |
| Leu | Asn | Gly | Ser | Ser | Ser | Ser | Ser | Ser | Ser | Ser | Arg | Ser | Val | Ser |
| | 1280 | | | | | 1285 | | | | 1290 | | |
| His | His | Ser | His | Glu | His | His | Ser | Gly | His | Leu | Glu | Asp | Asp | Ser |
| | 1295 | | | | | 1300 | | | | 1305 | | |
| Ser | Ser | Ser | Ser | Ser | Ser | Ser | Val | Leu | Ser | Lys | Ile | Trp | Gly | Arg |
| | 1310 | | | | | 1315 | | | | 1320 | | |
| His | Glu | Ile | Tyr | Gln | Tyr | Arg | Phe | Arg | Ser | Ala | His | Arg | Gln | Glu |
| | 1325 | | | | | 1330 | | | | 1335 | | |
| Phe | Pro | Lys | Arg | Lys | Leu | Pro | Gly | Asp | Arg | Ala | Thr | Ser | Arg | Tyr |
| | 1340 | | | | | 1345 | | | | 1350 | | |
| Ser | Ser | Thr | Arg | Ser | Ser | His | Asp | Thr | Ser | Arg | Ala | Ala | Ser | Trp |
| | 1355 | | | | | 1360 | | | | 1365 | | |
| Pro | Lys | Phe | Leu | Gly | Asp | Ile | Lys | Thr | Pro | Val | Leu | Ala | Ala | Phe |
| | 1370 | | | | | 1375 | | | | 1380 | | |
| Leu | His | Gly | Ile | Ser | Asn | Asn | Lys | Lys | Thr | Gly | Gly | Leu | Gln | Leu |
| | 1385 | | | | | 1390 | | | | 1395 | | |
| Val | Val | Tyr | Ala | Asp | Thr | Asp | Ser | Val | Arg | Pro | Arg | Val | Gln | Val |
| | 1400 | | | | | 1405 | | | | 1410 | | |
| Phe | Val | Thr | Asn | Leu | Thr | Asp | Ser | Ser | Lys | Trp | Lys | Leu | Cys | Ala |
| | 1415 | | | | | 1420 | | | | 1425 | | |
| Asp | Ala | Ser | Val | Arg | Asn | Ala | His | Lys | Ala | Val | Ala | Tyr | Val | Lys |
| | 1430 | | | | | 1435 | | | | 1440 | | |
| Trp | Gly | Trp | Asp | Cys | Arg | Asp | Tyr | Lys | Val | Ser | Thr | Glu | Leu | Val |
| | 1445 | | | | | 1450 | | | | 1455 | | |
| Thr | Gly | Arg | Phe | Ala | Gly | His | Pro | Ala | Ala | Gln | Val | Lys | Leu | Glu |
| | 1460 | | | | | 1465 | | | | 1470 | | |
| Trp | Pro | Lys | Val | Pro | Ser | Asn | Val | Arg | Ser | Val | Val | Glu | Trp | Phe |
| | 1475 | | | | | 1480 | | | | 1485 | | |
| Tyr | Glu | Phe | Val | Pro | Gly | Ala | Ala | Phe | Met | Leu | Gly | Phe | Ser | Glu |
| | 1490 | | | | | 1495 | | | | 1500 | | |
| Arg | Met | Asp | Lys | Asn | Pro | Ser | Arg | Gln | Ala | Arg | Met | Val | Val | Ala |
| | 1505 | | | | | 1510 | | | | 1515 | | |
| Leu | Thr | Ser | Pro | Arg | Thr | Cys | Asp | Val | Val | Lys | Leu | Pro | Asp |
| | 1520 | | | | | 1525 | | | | 1530 | | |
| Ile | Ile | Leu | Tyr | Gln | Lys | Ala | Val | Arg | Leu | Pro | Leu | Ser | Leu | Pro |
| | 1535 | | | | | 1540 | | | | 1545 | | |
| Val | Gly | Pro | Arg | Ile | Pro | Ala | Ser | Glu | Leu | Gln | Pro | Pro | Ile | Trp |
| | 1550 | | | | | 1555 | | | | 1560 | | |
| Asn | Val | Phe | Ala | Glu | Ala | Pro | Ser | Ala | Val | Leu | Glu | Asn | Leu | Lys |
| | 1565 | | | | | 1570 | | | | 1575 | | |
| Ala | Arg | Cys | Ser | Val | Ser | Tyr | Asn | Lys | Ile | Lys | Thr | Phe | Asn | Glu |

```
            1580                1585                1590
Val Lys Phe Asn Tyr Ser Met Pro Ala Asn Cys Tyr His Ile Leu
    1595                1600                1605

Val Gln Asp Cys Ser Ser Glu Leu Lys Phe Leu Val Met Met Lys
    1610                1615                1620

Ser Ala Gly Glu Ala Thr Asn Leu Lys Ala Ile Asn Ile Lys Ile
    1625                1630                1635

Gly Ser His Glu Ile Asp Met His Pro Val Asn Gly Gln Val Lys
    1640                1645                1650

Leu Leu Val Asp Gly Ala Glu Ser Pro Thr Ala Asn Ile Ser Leu
    1655                1660                1665

Ile Ser Ala Gly Ala Ser Leu Trp Ile His Asn Glu Asn Gln Gly
    1670                1675                1680

Phe Ala Leu Ala Ala Pro Gly His Gly Ile Asp Lys Leu Tyr Phe
    1685                1690                1695

Asp Gly Lys Thr Ile Thr Ile Gln Val Pro Leu Trp Met Ala Gly
    1700                1705                1710

Lys Thr Cys Gly Ile Cys Gly Lys Tyr Asp Ala Glu Cys Glu Gln
    1715                1720                1725

Glu Tyr Arg Met Pro Asn Gly Tyr Leu Ala Lys Asn Ala Val Ser
    1730                1735                1740

Phe Gly His Ser Trp Ile Leu Glu Glu Ala Pro Cys Arg Gly Ala
    1745                1750                1755

Cys Lys Leu His Arg Ser Phe Val Lys Leu Glu Lys Thr Val Gln
    1760                1765                1770

Leu Ala Gly Val Asp Ser Lys Cys Tyr Ser Thr Glu Pro Val Leu
    1775                1780                1785

Arg Cys Ala Lys Gly Cys Ser Ala Thr Lys Thr Thr Pro Val Thr
    1790                1795                1800

Val Gly Phe His Cys Leu Pro Ala Asp Ser Ala Asn Ser Leu Thr
    1805                1810                1815

Asp Lys Gln Met Lys Tyr Asp Gln Lys Ser Glu Asp Met Gln Asp
    1820                1825                1830

Thr Val Asp Ala His Thr Thr Cys Ser Cys Glu Asn Glu Glu Cys
    1835                1840                1845

Ser Thr
    1850

<210> SEQ ID NO 40
<211> LENGTH: 386
<212> TYPE: PRT
<213> ORGANISM: Gallus gallus

<400> SEQUENCE: 40

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80
```

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385

<210> SEQ ID NO 41
<211> LENGTH: 738
<212> TYPE: PRT
<213> ORGANISM: Gallus gallus

<400> SEQUENCE: 41

Met Lys Ser Ser Glu Asn Val Leu Tyr Leu Leu Val His Ala Ala
1               5                   10                  15

Leu Ser Leu Glu Arg Val Arg Trp Cys Thr Met Ser Asn Gln Glu Leu
            20                  25                  30

Ser Lys Cys Lys Asp Met Ser Asn Ala Phe Thr Gly Ala Gly Ile Leu
        35                  40                  45

Pro Pro Leu Glu Cys Met Glu Gly Glu Ser Ala Ala Asn Cys Thr Gln
    50                  55                  60

```
Met Ile Lys Asp Tyr Leu Ala Asp Thr Val Thr Leu Asp Gly Arg Trp
 65                  70                  75                  80

Ile Tyr Gln Ala Gly Lys Glu Tyr Gly Leu Lys Pro Val Val Gly Glu
                 85                  90                  95

Val Tyr Asp Gln Glu Ile Gly Thr Ser Tyr Tyr Ala Val Ala Val Val
                100                 105                 110

Arg Lys Gly Ser Asn Ile Thr Ile Asn Ser Leu Lys Gly Val Arg Ser
                115                 120                 125

Cys His Thr Gly Ile Asn Arg Thr Ala Gly Trp Asn Val Pro Val Gly
                130                 135                 140

Tyr Leu Ile Asp Ser Gly Arg Leu Pro Ala Met Gly Cys Asp Leu Pro
145                 150                 155                 160

Lys Ala Val Ser Asp Tyr Phe Ser Ala Ser Cys Val Pro Gly Thr Asn
                165                 170                 175

Ser Ala Ser Tyr Pro Thr Ser Leu Cys Gln Leu Cys Lys Gly Asp Ser
                180                 185                 190

Ser Gly Gln Asn Lys Cys Gln Gly Asn Ser Gln Glu Gln Tyr Tyr Asp
                195                 200                 205

Tyr Ser Gly Ala Phe Arg Cys Leu Ala Glu Gly Ala Gly Glu Val Ala
210                 215                 220

Phe Val Lys His Ser Thr Val Pro Glu Asn Thr Asp Gly Arg Thr Leu
225                 230                 235                 240

Ser Thr Trp Ala Gln Gln Phe Arg Ser Lys Asp Phe Gln Leu Leu Cys
                245                 250                 255

Arg Asn Gly Ser Thr Ala Asp Val Thr Glu Trp Arg Thr Cys His Leu
                260                 265                 270

Ala Arg Val Pro Ala Arg Ala Val Val Val Arg Pro Asp Thr Asp Gly
                275                 280                 285

Thr Ala Val Phe Gln Leu Leu Asn Gln Gly Gln Gln Arg Phe Asn Asp
                290                 295                 300

Val Gly Ala Gln Phe Gln Met Phe Asp Ser Thr Ala Tyr Gly Ala Gln
305                 310                 315                 320

Asn Leu Met Phe Arg Asp Ser Thr Thr Lys Leu Val Ala Val Thr Ser
                325                 330                 335

Gln Asn Tyr Gln Ala Trp Leu Gly Asp Glu Tyr Leu His Gly Met Gln
                340                 345                 350

Ala Leu Ser Cys Asp Pro Asn Thr Leu Pro Glu Ser Leu Asn Trp Cys
                355                 360                 365

Val Val Ser Thr Glu Glu Ile Trp Lys Cys Gly Glu Met Gly Thr Ala
                370                 375                 380

Phe Arg Ser Lys Asn Leu Lys Pro Glu Ile Gln Cys Ile Ser Ala Lys
385                 390                 395                 400

Thr Lys Glu Glu Cys Met Glu Met Ile Gln Lys Glu Ile Asp Val
                405                 410                 415

Val Ala Leu Gly Gly Val Asp Ile Tyr Ile Ala Gly Lys Thr Tyr Gly
                420                 425                 430

Leu Val Pro Ala Ala Gly Glu Ser Phe Ser Ala Glu Asp Asn Asn Asn
                435                 440                 445

Ala Tyr Tyr Ala Val Ala Leu Val Lys Arg Asn Pro Ser Asn Ala Phe
                450                 455                 460

Thr Ile Asn Asp Leu Lys Gly Lys Lys Ser Cys His Thr Gly Leu Gly
465                 470                 475                 480
```

```
Arg Thr Ala Gly Trp Asn Ile Pro Ile Gly Met Leu Val Lys Lys Gly
                    485                 490                 495

Phe Ile Asn Pro Arg Asp Cys Asn Ile Pro Gln Ala Val Ser Glu Phe
                500                 505                 510

Phe Ser Ala Ser Cys Val Pro Ser Ala Glu Gln Gly Asn Tyr Pro Ser
            515                 520                 525

Thr Leu Cys Gln Leu Cys Ile Gly Asp Asn Gly Asn Asn Lys Cys
        530                 535                 540

Ser Ala Ser Ser Gln Glu Arg Tyr Tyr Ser Tyr Asn Gly Ala Phe Arg
545                 550                 555                 560

Cys Leu Ala Glu Asp Ala Gly Asp Val Ala Phe Val Lys His Ser Thr
                565                 570                 575

Val Phe Glu Asn Thr Asp Gly Lys Asn Thr Glu Ser Trp Ala Arg Asp
                580                 585                 590

Leu Lys Ser Ser Gly Phe Gln Leu Leu Cys Arg Asn Gly Ala Arg Ala
            595                 600                 605

Glu Val Thr Gln Phe Ala Gln Cys His Leu Ala Arg Val Pro Ala Gln
        610                 615                 620

Ala Ile Met Val His Pro Asp Thr Asn Ile Phe Ala Leu Tyr Gly Leu
625                 630                 635                 640

Leu Asp Lys Ala Gln Glu Tyr Phe Gly Asn Asn Ser Asn Arg Asn Gly
                645                 650                 655

Phe Lys Met Phe Asp Ser Ser Ala Phe Gln Gly Lys Asp Leu Ile Phe
            660                 665                 670

Lys Asp Ser Ala Val Lys Ile Val Pro Val Glu Glu Arg Arg Thr Tyr
        675                 680                 685

Ala Glu Trp Leu Gly Ser Glu Tyr Val Glu Ser Leu Glu Gly Met Gln
690                 695                 700

Thr Pro Gln Cys Ser Gly Ala Gly Asn Lys Leu Ile Gln Gln His Leu
705                 710                 715                 720

Leu Val Ile Thr Phe Val Pro Phe Ile Ile Leu Gly Gln Leu Gln Gly
                725                 730                 735

Leu Gly

<210> SEQ ID NO 42
<211> LENGTH: 210
<212> TYPE: PRT
<213> ORGANISM: Gallus gallus

<400> SEQUENCE: 42

Met Ala Met Ala Gly Val Phe Val Leu Phe Ser Val Leu Cys Gly
1               5                   10                  15

Phe Leu Pro Asp Ala Ala Phe Gly Ala Glu Val Asp Cys Ser Arg Phe
                20                  25                  30

Pro Asn Ala Thr Asp Lys Glu Gly Lys Asp Val Leu Val Cys Asn Lys
            35                  40                  45

Asp Leu Arg Pro Ile Cys Gly Thr Asp Gly Val Thr Tyr Thr Asn Asp
        50                  55                  60

Cys Leu Leu Cys Ala Tyr Ser Ile Glu Phe Gly Thr Asn Ile Ser Lys
65                  70                  75                  80

Glu His Asp Gly Glu Cys Lys Glu Thr Val Pro Met Asn Cys Ser Ser
                85                  90                  95

Tyr Ala Asn Thr Thr Ser Glu Asp Gly Lys Val Met Val Leu Cys Asn
            100                 105                 110
```

-continued

```
Arg Ala Phe Asn Pro Val Cys Gly Thr Asp Gly Val Thr Tyr Asp Asn
            115                 120                 125

Glu Cys Leu Leu Cys Ala His Lys Val Glu Gln Gly Ala Ser Val Asp
130                 135                 140

Lys Arg His Asp Gly Gly Cys Arg Lys Glu Leu Ala Ala Val Ser Val
145                 150                 155                 160

Asp Cys Ser Glu Tyr Pro Lys Pro Asp Cys Thr Ala Glu Asp Arg Pro
                165                 170                 175

Leu Cys Gly Ser Asp Asn Lys Thr Tyr Gly Asn Lys Cys Asn Phe Cys
            180                 185                 190

Asn Ala Val Val Glu Ser Asn Gly Thr Leu Thr Leu Ser His Phe Gly
            195                 200                 205

Lys Cys
    210

<210> SEQ ID NO 43
<211> LENGTH: 2108
<212> TYPE: PRT
<213> ORGANISM: Gallus gallus

<400> SEQUENCE: 43

Met Glu Ile Lys Lys Glu Arg Ser Phe Trp Ile Phe Cys Leu Ile Trp
1               5                   10                  15

Ser Phe Cys Lys Gly Lys Glu Pro Val Gln Ile Val Gln Val Ser Thr
            20                  25                  30

Val Gly Arg Ser Glu Cys Thr Thr Trp Gly Asn Phe His Phe His Thr
        35                  40                  45

Phe Asp His Val Lys Phe Thr Phe Pro Gly Thr Cys Thr Tyr Val Phe
50                  55                  60

Ala Ser His Cys Asn Asp Ser Tyr Gln Asp Phe Asn Ile Lys Ile Arg
65                  70                  75                  80

Arg Ser Asp Lys Asn Ser His Leu Ile Tyr Phe Thr Val Thr Thr Asp
                85                  90                  95

Gly Val Ile Leu Glu Val Lys Glu Thr Gly Ile Thr Val Asn Gly Asn
            100                 105                 110

Gln Ile Pro Leu Pro Phe Ser Leu Lys Ser Ile Leu Ile Glu Asp Thr
        115                 120                 125

Cys Ala Tyr Phe Gln Val Thr Ser Lys Leu Gly Leu Thr Leu Lys Trp
    130                 135                 140

Asn Trp Ala Asp Thr Leu Leu Leu Asp Leu Glu Glu Thr Tyr Lys Glu
145                 150                 155                 160

Lys Ile Cys Gly Leu Cys Gly Asn Tyr Asp Gly Asn Lys Lys Asn Asp
                165                 170                 175

Leu Ile Leu Asp Gly Tyr Lys Met His Pro Arg Gln Phe Gly Asn Phe
            180                 185                 190

His Lys Val Glu Asp Pro Ser Glu Lys Cys Pro Asp Val Arg Pro Asp
        195                 200                 205

Asp His Thr Gly Arg His Pro Thr Glu Asp Asp Asn Arg Cys Ser Lys
    210                 215                 220

Tyr Lys Lys Met Cys Lys Lys Leu Leu Ser Arg Phe Gly Asn Cys Pro
225                 230                 235                 240

Lys Val Val Ala Phe Asp Asp Tyr Val Ala Thr Cys Thr Glu Asp Met
                245                 250                 255

Cys Asn Cys Val Val Asn Ser Ser Gln Ser Asp Leu Val Ser Ser Cys
            260                 265                 270
```

```
Ile Cys Ser Thr Leu Asn Gln Tyr Ser Arg Asp Cys Val Leu Ser Lys
        275                 280                 285

Gly Asp Pro Gly Glu Trp Arg Thr Lys Glu Leu Cys Tyr Gln Glu Cys
290                 295                 300

Pro Ser Asn Met Glu Tyr Met Glu Cys Gly Asn Ser Cys Ala Asp Thr
305                 310                 315                 320

Cys Ala Asp Pro Glu Arg Ser Lys Ile Cys Lys Ala Pro Cys Thr Asp
                325                 330                 335

Gly Cys Phe Cys Pro Gly Thr Ile Leu Asp Asp Leu Gly Gly Lys
                340                 345                 350

Lys Cys Val Pro Arg Asp Ser Cys Pro Cys Met Phe Gln Gly Lys Val
        355                 360                 365

Tyr Ser Ser Gly Gly Thr Tyr Ser Thr Pro Cys Gln Asn Cys Thr Cys
    370                 375                 380

Lys Gly Gly His Trp Ser Cys Ile Ser Leu Pro Cys Ser Gly Ser Cys
385                 390                 395                 400

Ser Ile Asp Gly Gly Phe His Ile Lys Thr Phe Asp Asn Lys Lys Phe
                405                 410                 415

Asn Phe His Gly Asn Cys His Tyr Val Leu Ala Lys Asn Thr Asp Asp
                420                 425                 430

Thr Phe Val Val Ile Gly Glu Ile Ile Gln Cys Gly Thr Ser Lys Thr
    435                 440                 445

Met Thr Cys Leu Lys Asn Val Leu Val Thr Leu Gly Arg Thr Thr Ile
        450                 455                 460

Lys Ile Cys Ser Cys Gly Ser Ile Tyr Met Asn Asn Phe Ile Val Lys
465                 470                 475                 480

Leu Pro Val Ser Lys Asp Gly Ile Thr Ile Phe Arg Pro Ser Thr Phe
                485                 490                 495

Phe Ile Lys Ile Leu Ser Ser Ala Gly Val Gln Ile Arg Val Gln Met
                500                 505                 510

Lys Pro Val Met Gln Leu Ser Ile Thr Val Asp His Ser Tyr Gln Asn
            515                 520                 525

Arg Thr Ser Gly Leu Cys Gly Asn Phe Asn Asn Ile Gln Thr Asp Asp
    530                 535                 540

Phe Arg Thr Ala Thr Gly Ala Val Glu Asp Ser Ala Ala Ala Phe Gly
545                 550                 555                 560

Asn Ser Trp Lys Thr Arg Ala Ser Cys Phe Asp Val Glu Asp Ser Phe
                565                 570                 575

Glu Asp Pro Cys Ser Asn Ser Val Asp Lys Glu Lys Phe Ala Gln His
                580                 585                 590

Trp Cys Ala Leu Leu Ser Asn Thr Ser Ser Thr Phe Ala Ala Cys His
        595                 600                 605

Ser Val Val Asp Pro Ser Val Tyr Ile Lys Arg Cys Met Tyr Asp Thr
    610                 615                 620

Cys Asn Ala Glu Lys Ser Glu Val Ala Leu Cys Ser Val Leu Ser Thr
625                 630                 635                 640

Tyr Ser Arg Asp Cys Ala Ala Ala Gly Met Thr Leu Lys Gly Trp Arg
                645                 650                 655

Gln Gly Ile Cys Asp Pro Ser Glu Glu Cys Pro Glu Thr Met Val Tyr
                660                 665                 670

Asn Tyr Ser Val Lys Tyr Cys Asn Gln Ser Cys Arg Ser Leu Asp Glu
            675                 680                 685
```

-continued

```
Pro Asp Pro Leu Cys Lys Val Gln Ile Ala Pro Met Glu Gly Cys Gly
    690                 695                 700
Cys Pro Glu Gly Thr Tyr Leu Asn Asp Glu Glu Cys Val Thr Pro
705                 710                 715                 720
Asp Asp Cys Pro Cys Tyr Tyr Lys Gly Lys Ile Val Gln Pro Gly Asn
                725                 730                 735
Ser Phe Gln Glu Asp Lys Leu Leu Cys Lys Cys Ile Gln Gly Arg Leu
            740                 745                 750
Asp Cys Ile Gly Glu Thr Val Leu Val Lys Asp Cys Pro Ala Pro Met
        755                 760                 765
Tyr Tyr Phe Asn Cys Ser Ser Ala Gly Pro Gly Ala Ile Gly Ser Glu
    770                 775                 780
Cys Gln Lys Ser Cys Lys Thr Gln Asp Met His Cys Tyr Val Thr Glu
785                 790                 795                 800
Cys Val Ser Gly Cys Met Cys Pro Asp Gly Leu Val Leu Asp Gly Ser
                805                 810                 815
Gly Gly Cys Ile Pro Lys Asp Gln Cys Pro Cys Val His Gly Gly His
            820                 825                 830
Phe Tyr Lys Pro Gly Glu Thr Ile Arg Val Asp Cys Asn Thr Cys Thr
        835                 840                 845
Cys Asn Lys Arg Gln Trp Asn Cys Thr Asp Asn Pro Cys Lys Gly Thr
    850                 855                 860
Cys Thr Val Tyr Gly Asn Gly His Tyr Met Ser Phe Asp Gly Glu Lys
865                 870                 875                 880
Phe Asp Phe Leu Gly Asp Cys Asp Tyr Ile Leu Ala Gln Asp Phe Cys
                885                 890                 895
Pro Asn Asn Met Asp Ala Gly Thr Phe Arg Ile Val Ile Gln Asn Asn
            900                 905                 910
Ala Cys Gly Lys Ser Leu Ser Ile Cys Ser Leu Lys Ile Thr Leu Ile
        915                 920                 925
Phe Glu Ser Ser Glu Ile Arg Leu Leu Glu Gly Arg Ile Gln Glu Ile
    930                 935                 940
Ala Thr Asp Pro Gly Ala Glu Lys Asn Tyr Lys Val Asp Leu Arg Gly
945                 950                 955                 960
Gly Tyr Ile Val Ile Glu Thr Thr Gln Gly Met Ser Phe Met Trp Asp
                965                 970                 975
Gln Lys Thr Thr Val Val Val His Val Thr Pro Ser Phe Gln Gly Lys
            980                 985                 990
Val Cys Gly Leu Cys Gly Asp Phe  Asp Gly Arg Ser Arg  Asn Asp Phe
        995                 1000                1005
Thr Thr Arg Gly Gln Ser Val  Glu Met Ser Ile Gln  Glu Phe Gly
    1010                1015                1020
Asn Ser Trp Lys Ile Thr Ser  Thr Cys Ser Asn Ile  Asn Met Thr
    1025                1030                1035
Asp Leu Cys Ala Asp Gln Pro  Phe Lys Ser Ala Leu  Gly Gln Lys
    1040                1045                1050
His Cys Ser Ile Ile Lys Ser  Val Phe Glu Ala  Cys His Ser
    1055                1060                1065
Lys Val Asn Pro Ile Pro Tyr  Tyr Glu Cys Val  Ser Asp Phe
    1070                1075                1080
Cys Gly Cys Asp Ser Val Gly  Asp Cys Glu Cys Phe  Cys Thr Ser
    1085                1090                1095
Val Ala Ala Tyr Ala Arg Ser  Cys Ser Thr Ala Gly  Val Cys Ile
```

-continued

```
            1100                1105                1110
Asn Trp Arg Thr Pro Ala Ile Cys Pro Val Phe Cys Asp Tyr Tyr
    1115                1120                1125
Asn Pro Pro Asp Lys His Glu Trp Phe Tyr Lys Pro Cys Gly Ala
    1130                1135                1140
Pro Cys Leu Lys Thr Cys Arg Asn Pro Gln Gly Lys Cys Gly Asn
    1145                1150                1155
Ile Leu Tyr Ser Leu Glu Gly Cys Tyr Pro Glu Cys Ser Pro Asp
    1160                1165                1170
Lys Pro Tyr Phe Asp Glu Glu Arg Arg Glu Cys Val Ser Leu Pro
    1175                1180                1185
Asp Cys Thr Ser Cys Asn Pro Glu Glu Lys Leu Cys Thr Glu Asp
    1190                1195                1200
Ser Lys Asp Cys Leu Cys Cys Tyr Asn Gly Lys Thr Tyr Pro Leu
    1205                1210                1215
Asn Glu Thr Ile Tyr Ser Gln Thr Glu Gly Thr Lys Cys Gly Asn
    1220                1225                1230
Ala Phe Cys Gly Pro Asn Gly Met Ile Ile Glu Thr Phe Ile Pro
    1235                1240                1245
Cys Ser Thr Leu Ser Val Pro Ala Gln Glu Gln Leu Met Gln Pro
    1250                1255                1260
Val Thr Ser Ala Pro Leu Leu Ser Thr Glu Ala Thr Pro Cys Phe
    1265                1270                1275
Cys Thr Asp Asn Gly Gln Leu Ile Gln Met Gly Glu Asn Val Ser
    1280                1285                1290
Leu Pro Met Asn Ile Ser Gly His Cys Ala Tyr Ser Ile Cys Asn
    1295                1300                1305
Ala Ser Cys Gln Ile Glu Leu Ile Trp Ala Glu Cys Lys Val Val
    1310                1315                1320
Gln Thr Glu Ala Leu Glu Thr Cys Glu Pro Asn Ser Glu Ala Cys
    1325                1330                1335
Pro Pro Thr Ala Ala Pro Asn Ala Thr Ser Leu Val Pro Ala Thr
    1340                1345                1350
Ala Leu Ala Pro Met Ser Asp Cys Leu Gly Leu Ile Pro Pro Arg
    1355                1360                1365
Lys Phe Asn Glu Ser Trp Asp Phe Gly Asn Cys Gln Ile Ala Thr
    1370                1375                1380
Cys Leu Gly Glu Glu Asn Asn Ile Lys Leu Ser Ser Ile Thr Cys
    1385                1390                1395
Pro Pro Gln Gln Leu Lys Leu Cys Val Asn Gly Phe Pro Phe Met
    1400                1405                1410
Lys His His Asp Glu Thr Gly Cys Cys Glu Val Phe Glu Cys Gln
    1415                1420                1425
Cys Ile Cys Ser Gly Trp Gly Asn Glu His Tyr Val Thr Phe Asp
    1430                1435                1440
Gly Thr Tyr Tyr His Phe Lys Glu Asn Cys Thr Tyr Val Leu Val
    1445                1450                1455
Glu Leu Ile Gln Pro Ser Ser Glu Lys Phe Trp Ile His Ile Asp
    1460                1465                1470
Asn Tyr Tyr Cys Gly Ala Ala Asp Gly Ala Ile Cys Ser Met Ser
    1475                1480                1485
Leu Leu Ile Phe His Ser Asn Ser Leu Val Ile Leu Thr Gln Ala
    1490                1495                1500
```

```
Lys Glu His Gly Lys Gly Thr Asn Leu Val Leu Phe Asn Asp Lys
1505                1510                1515

Lys Val Val Pro Asp Ile Ser Lys Asn Gly Ile Arg Ile Thr Ser
1520                1525                1530

Ser Gly Leu Tyr Ile Ile Val Glu Ile Pro Glu Leu Glu Val Tyr
1535                1540                1545

Val Ser Tyr Ser Arg Leu Ala Phe Tyr Ile Lys Leu Pro Phe Gly
1550                1555                1560

Lys Tyr Tyr Asn Asn Thr Met Gly Leu Cys Gly Thr Cys Thr Asn
1565                1570                1575

Gln Lys Ser Asp Asp Ala Arg Lys Arg Asn Gly Glu Val Thr Asp
1580                1585                1590

Ser Phe Lys Glu Met Ala Leu Asp Trp Lys Ala Pro Val Ser Thr
1595                1600                1605

Asn Arg Tyr Cys Asn Pro Gly Ile Ser Glu Pro Val Lys Ile Glu
1610                1615                1620

Asn Tyr Gln His Cys Glu Pro Ser Glu Leu Cys Lys Ile Ile Trp
1625                1630                1635

Asn Leu Thr Glu Cys His Arg Val Val Pro Pro Gln Pro Tyr Tyr
1640                1645                1650

Glu Ala Cys Val Ala Ser Arg Cys Ser Gln Gln His Pro Ser Thr
1655                1660                1665

Glu Cys Gln Ser Met Gln Thr Tyr Ala Ala Leu Cys Gly Leu His
1670                1675                1680

Gly Ile Cys Val Asp Trp Arg Gly Gln Thr Asn Gly Gln Cys Glu
1685                1690                1695

Ala Thr Cys Ala Arg Asp Gln Val Tyr Lys Pro Cys Gly Glu Ala
1700                1705                1710

Lys Arg Asn Thr Cys Phe Ser Arg Glu Val Ile Val Asp Thr Leu
1715                1720                1725

Leu Ser Arg Asn Asn Thr Pro Val Phe Val Glu Gly Cys Tyr Cys
1730                1735                1740

Pro Asp Gly Asn Ile Leu Leu Asn Glu His Asp Gly Ile Cys Val
1745                1750                1755

Ser Val Cys Gly Cys Thr Ala Gln Asp Gly Ser Val Lys Lys Pro
1760                1765                1770

Arg Glu Ala Trp Glu His Asp Cys Gln Tyr Cys Thr Cys Asp Glu
1775                1780                1785

Glu Thr Leu Asn Ile Ser Cys Phe Pro Arg Pro Cys Ala Lys Ser
1790                1795                1800

Pro Pro Ile Asn Cys Thr Lys Glu Gly Phe Val Arg Lys Ile Lys
1805                1810                1815

Pro Arg Leu Asp Asp Pro Cys Cys Thr Glu Thr Val Cys Glu Cys
1820                1825                1830

Asp Ile Lys Thr Cys Ile Ile Asn Lys Thr Ala Cys Asp Leu Gly
1835                1840                1845

Phe Gln Pro Val Val Ala Ile Ser Glu Asp Gly Cys Cys Pro Ile
1850                1855                1860

Phe Ser Cys Ile Pro Lys Gly Val Cys Val Ser Glu Gly Val Glu
1865                1870                1875

Phe Lys Pro Gly Ala Val Val Pro Lys Ser Ser Cys Glu Asp Cys
1880                1885                1890
```

-continued

Val Cys Thr Asp Glu Gln Asp Ala Val Thr Gly Thr Asn Arg Ile
1895                1900                    1905

Gln Cys Val Pro Val Lys Cys Gln Thr Thr Cys Gln Gln Gly Phe
1910                1915                    1920

Arg Tyr Val Glu Lys Glu Gly Gln Cys Cys Ser Gln Cys Gln Gln
1925                1930                    1935

Val Ala Cys Val Ala Asn Phe Pro Phe Gly Ser Val Thr Ile Glu
1940                1945                    1950

Val Gly Lys Ser Tyr Lys Ala Pro Tyr Asp Asn Cys Thr Gln Tyr
1955                1960                    1965

Thr Cys Thr Glu Ser Gly Gly Gln Phe Ser Leu Thr Ser Thr Val
1970                1975                    1980

Lys Val Cys Leu Pro Phe Glu Glu Ser Asn Cys Val Pro Gly Thr
1985                1990                    1995

Val Asp Val Thr Ser Asp Gly Cys Cys Lys Thr Cys Ile Asp Leu
2000                2005                    2010

Pro His Lys Cys Lys Arg Ser Met Lys Glu Gln Tyr Ile Val His
2015                2020                    2025

Lys His Cys Lys Ser Ala Ala Pro Val Pro Val Pro Phe Cys Glu
2030                2035                    2040

Gly Thr Cys Ser Thr Tyr Ser Val Tyr Ser Phe Glu Asn Asn Glu
2045                2050                    2055

Met Glu His Lys Cys Ile Cys Cys His Glu Lys Lys Ser His Val
2060                2065                    2070

Glu Lys Val Glu Leu Val Cys Ser Glu His Lys Thr Leu Lys Phe
2075                2080                    2085

Ser Tyr Val His Val Asp Glu Cys Gly Cys Val Glu Thr Lys Cys
2090                2095                    2100

Pro Met Arg Arg Thr
2105

<210> SEQ ID NO 44
<211> LENGTH: 1185
<212> TYPE: PRT
<213> ORGANISM: Gallus gallus

<400> SEQUENCE: 44

Cys Ser Thr Trp Gly Gly Gly His Phe Ser Thr Phe Asp Lys Tyr Gln
1               5                   10                  15

Tyr Asp Phe Thr Gly Thr Cys Asn Tyr Ile Phe Ala Thr Val Cys Asp
                20                  25                  30

Glu Ser Ser Pro Asp Phe Asn Ile Gln Phe Arg Arg Gly Leu Asp Lys
            35                  40                  45

Lys Ile Ala Arg Ile Ile Ile Glu Leu Gly Pro Ser Val Ile Ile Val
        50                  55                  60

Glu Lys Asp Ser Ile Ser Val Arg Ser Val Gly Val Ile Lys Leu Pro
65                  70                  75                  80

Tyr Ala Ser Asn Gly Ile Gln Ile Ala Pro Tyr Gly Arg Ser Val Arg
                85                  90                  95

Leu Val Ala Lys Leu Met Glu Met Glu Leu Val Val Met Trp Asn Asn
            100                 105                 110

Glu Asp Tyr Leu Met Val Leu Thr Glu Lys Lys Tyr Met Gly Lys Thr
        115                 120                 125

Cys Gly Met Cys Gly Asn Tyr Asp Gly Tyr Glu Leu Asn Asp Phe Val
    130                 135                 140

```
Ser Glu Gly Lys Leu Leu Asp Thr Tyr Lys Phe Ala Leu Gln Lys
145                 150                 155                 160

Met Asp Asp Pro Ser Glu Ile Cys Leu Ser Glu Ile Ser Ile Pro
                165                 170                 175

Ala Ile Pro His Lys Lys Tyr Ala Val Ile Cys Ser Gln Leu Leu Asn
                180                 185                 190

Leu Val Ser Pro Thr Cys Ser Val Pro Lys Asp Gly Phe Val Thr Arg
                195                 200                 205

Cys Gln Leu Asp Met Gln Asp Cys Ser Glu Pro Gly Gln Lys Asn Cys
                210                 215                 220

Thr Cys Ser Thr Leu Ser Glu Tyr Ser Arg Gln Cys Ala Met Ser His
225                 230                 235                 240

Gln Val Val Phe Asn Trp Arg Thr Glu Asn Phe Cys Ser Val Gly Lys
                245                 250                 255

Cys Ser Ala Asn Gln Ile Tyr Glu Glu Cys Gly Ser Pro Cys Ile Lys
                260                 265                 270

Thr Cys Ser Asn Pro Glu Tyr Ser Cys Ser Ser His Cys Thr Tyr Gly
                275                 280                 285

Cys Phe Cys Pro Glu Gly Thr Val Leu Asp Asp Ile Ser Lys Asn Arg
290                 295                 300

Thr Cys Val His Leu Glu Gln Cys Pro Cys Thr Leu Asn Gly Glu Thr
305                 310                 315                 320

Tyr Ala Pro Gly Asp Thr Met Lys Ala Ala Cys Arg Thr Cys Lys Cys
                325                 330                 335

Thr Met Gly Gln Trp Asn Cys Lys Glu Leu Pro Cys Pro Gly Arg Cys
                340                 345                 350

Ser Leu Glu Gly Gly Ser Phe Val Thr Thr Phe Asp Ser Arg Ser Tyr
                355                 360                 365

Arg Phe His Gly Val Cys Thr Tyr Ile Leu Met Lys Ser Ser Ser Leu
370                 375                 380

Pro His Asn Gly Thr Leu Met Ala Ile Tyr Glu Lys Ser Gly Tyr Ser
385                 390                 395                 400

His Ser Glu Thr Ser Leu Ser Ala Ile Ile Tyr Leu Ser Thr Lys Asp
                405                 410                 415

Lys Ile Val Ile Ser Gln Asn Glu Leu Leu Thr Asp Asp Glu Leu
                420                 425                 430

Lys Arg Leu Pro Tyr Lys Ser Gly Asp Ile Thr Ile Phe Lys Gln Ser
                435                 440                 445

Ser Met Phe Ile Gln Met His Thr Glu Phe Gly Leu Glu Leu Val Val
450                 455                 460

Gln Thr Ser Pro Val Phe Gln Ala Tyr Val Lys Val Ser Ala Gln Phe
465                 470                 475                 480

Gln Gly Arg Thr Leu Gly Leu Cys Gly Asn Tyr Asn Gly Asp Thr Thr
                485                 490                 495

Asp Asp Phe Met Thr Ser Met Asp Ile Thr Glu Gly Thr Ala Ser Leu
                500                 505                 510

Phe Val Asp Ser Trp Arg Ala Gly Asn Cys Leu Pro Ala Met Glu Arg
                515                 520                 525

Glu Thr Asp Pro Cys Ala Leu Ser Gln Leu Asn Lys Ile Ser Ala Glu
                530                 535                 540

Thr His Cys Ser Ile Leu Thr Lys Lys Gly Thr Val Phe Glu Thr Cys
545                 550                 555                 560
```

```
His Ala Val Val Asn Pro Thr Pro Phe Tyr Lys Arg Cys Val Tyr Gln
                565                 570                 575

Ala Cys Asn Tyr Glu Glu Thr Phe Pro Tyr Ile Cys Ser Ala Leu Gly
            580                 585                 590

Ser Tyr Ala Arg Thr Cys Ser Ser Met Gly Leu Ile Leu Glu Asn Trp
        595                 600                 605

Arg Asn Ser Met Asp Asn Cys Thr Ile Thr Cys Thr Gly Asn Gln Thr
    610                 615                 620

Phe Ser Tyr Asn Thr Gln Ala Cys Glu Arg Thr Cys Leu Ser Leu Ser
625                 630                 635                 640

Asn Pro Thr Leu Glu Cys His Pro Thr Asp Ile Pro Ile Glu Gly Cys
                645                 650                 655

Asn Cys Pro Lys Gly Met Tyr Leu Asn His Lys Asn Glu Cys Val Arg
            660                 665                 670

Lys Ser His Cys Pro Cys Tyr Leu Glu Asp Arg Lys Tyr Ile Leu Pro
        675                 680                 685

Asp Gln Ser Thr Met Thr Gly Gly Ile Thr Cys Tyr Cys Val Asn Gly
    690                 695                 700

Arg Leu Ser Cys Thr Gly Lys Leu Gln Asn Pro Ala Glu Ser Cys Lys
705                 710                 715                 720

Ala Pro Lys Lys Tyr Ile Ser Cys Ser Asp Ser Leu Glu Asn Lys Tyr
                725                 730                 735

Gly Ala Thr Cys Ala Pro Thr Cys Gln Met Leu Ala Thr Gly Ile Glu
            740                 745                 750

Cys Ile Pro Thr Lys Cys Glu Ser Gly Cys Val Cys Ala Asp Gly Leu
        755                 760                 765

Tyr Glu Asn Leu Asp Gly Arg Cys Val Pro Pro Glu Glu Cys Pro Cys
    770                 775                 780

Glu Tyr Gly Gly Leu Ser Tyr Gly Lys Gly Glu Gln Ile Gln Thr Glu
785                 790                 795                 800

Cys Glu Ile Cys Thr Cys Arg Lys Gly Lys Trp Lys Cys Val Gln Lys
                805                 810                 815

Ser Arg Cys Ser Ser Thr Cys Asn Leu Tyr Gly Glu Gly His Ile Thr
            820                 825                 830

Thr Phe Asp Gly Gln Arg Phe Val Phe Asp Gly Asn Cys Glu Tyr Ile
        835                 840                 845

Leu Ala Met Asp Gly Cys Asn Val Asn Arg Pro Leu Ser Ser Phe Lys
    850                 855                 860

Ile Val Thr Glu Asn Val Ile Cys Gly Lys Ser Gly Val Thr Cys Ser
865                 870                 875                 880

Arg Ser Ile Ser Ile Tyr Leu Gly Asn Leu Thr Ile Ile Leu Arg Asp
                885                 890                 895

Glu Thr Tyr Ser Ile Ser Gly Lys Asn Leu Gln Val Lys Tyr Asn Val
            900                 905                 910

Lys Lys Asn Ala Leu His Leu Met Phe Asp Ile Ile Pro Gly Lys
        915                 920                 925

Tyr Asn Met Thr Leu Ile Trp Asn Lys His Met Asn Phe Phe Ile Lys
    930                 935                 940

Ile Ser Arg Glu Thr Gln Glu Thr Ile Cys Gly Leu Cys Gly Asn Tyr
945                 950                 955                 960

Asn Gly Asn Met Lys Asp Asp Phe Glu Thr Arg Ser Lys Tyr Val Ala
                965                 970                 975

Ser Asn Glu Leu Glu Phe Val Asn Ser Trp Lys Glu Asn Pro Leu Cys
```

-continued

```
                  980             985                 990
Gly Asp Val Tyr Phe Val Val Asp Pro Cys Ser Lys Asn Pro Tyr Arg
              995                1000                1005

Lys Ala Trp Ala Glu Lys Thr Cys Ser Ile Ile Asn Ser Gln Val
   1010                1015                1020

Phe Ser Ala Cys His Asn Lys Val Asn Arg Met Pro Tyr Tyr Glu
   1025                1030                1035

Ala Cys Val Arg Asp Ser Cys Gly Cys Asp Ile Gly Gly Asp Cys
   1040                1045                1050

Glu Cys Met Cys Asp Ala Ile Ala Val Tyr Ala Met Ala Cys Leu
   1055                1060                1065

Asp Lys Gly Ile Cys Ile Asp Trp Arg Thr Pro Glu Phe Cys Pro
   1070                1075                1080

Val Tyr Cys Glu Tyr Tyr Asn Ser His Arg Lys Thr Gly Ser Gly
   1085                1090                1095

Gly Ala Tyr Ser Tyr Gly Ser Ser Val Asn Cys Thr Trp His Tyr
   1100                1105                1110

Arg Pro Cys Asn Cys Pro Asn Gln Tyr Tyr Lys Tyr Val Asn Ile
   1115                1120                1125

Glu Gly Cys Tyr Asn Cys Ser His Asp Glu Tyr Phe Asp Tyr Glu
   1130                1135                1140

Lys Glu Lys Cys Met Pro Cys Ala Met Gln Pro Thr Ser Val Thr
   1145                1150                1155

Leu Pro Thr Ala Thr Gln Pro Thr Ser Pro Ser Thr Ser Ser Ala
   1160                1165                1170

Ser Thr Val Leu Thr Glu Thr Thr Asn Pro Pro Val
   1175                1180                1185

<210> SEQ ID NO 45
<211> LENGTH: 211
<212> TYPE: PRT
<213> ORGANISM: Gallus gallus

<400> SEQUENCE: 45

Met Leu Gly Lys Asn Asp Pro Met Cys Leu Val Leu Val Leu Leu Gly
1               5                   10                  15

Leu Thr Ala Leu Leu Gly Ile Cys Gln Gly Gly Thr Gly Cys Tyr Gly
            20                  25                  30

Ser Val Ser Arg Ile Asp Thr Thr Gly Ala Ser Cys Arg Thr Ala Lys
        35                  40                  45

Pro Glu Gly Leu Ser Tyr Cys Gly Val Arg Ala Ser Arg Thr Ile Ala
    50                  55                  60

Glu Arg Asp Leu Gly Ser Met Asn Lys Tyr Lys Val Leu Ile Lys Arg
65                  70                  75                  80

Val Gly Glu Ala Leu Cys Ile Glu Pro Ala Val Ile Ala Gly Ile Ile
                85                  90                  95

Ser Arg Glu Ser His Ala Gly Lys Ile Leu Lys Asn Gly Trp Gly Asp
            100                 105                 110

Arg Gly Asn Gly Phe Gly Leu Met Gln Val Asp Lys Arg Tyr His Lys
        115                 120                 125

Ile Glu Gly Thr Trp Asn Gly Glu Ala His Ile Arg Gln Gly Thr Arg
    130                 135                 140

Ile Leu Ile Asp Met Val Lys Lys Ile Gln Arg Lys Phe Pro Arg Trp
145                 150                 155                 160
```

```
Thr Arg Asp Gln Gln Leu Lys Gly Gly Ile Ser Ala Tyr Asn Ala Gly
            165                 170                 175

Val Gly Asn Val Arg Ser Tyr Glu Arg Met Asp Ile Gly Thr Leu His
        180                 185                 190

Asp Asp Tyr Ser Asn Asp Val Val Ala Arg Ala Gln Tyr Phe Lys Gln
            195                 200                 205

His Gly Tyr
    210

<210> SEQ ID NO 46
<211> LENGTH: 147
<212> TYPE: PRT
<213> ORGANISM: Gallus gallus

<400> SEQUENCE: 46

Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145

<210> SEQ ID NO 47
<211> LENGTH: 1453
<212> TYPE: PRT
<213> ORGANISM: Gallus gallus

<400> SEQUENCE: 47

Met Phe Ser Phe Val Asp Ser Arg Leu Leu Leu Ile Ala Ala Thr
1               5                   10                  15

Val Leu Leu Thr Arg Gly Glu Gly Glu Glu Asp Ile Gln Thr Gly Ser
            20                  25                  30

Cys Val Gln Asp Gly Leu Thr Tyr Asn Asp Lys Asp Val Trp Lys Pro
        35                  40                  45

Glu Pro Cys Gln Ile Cys Val Cys Asp Ser Gly Asn Ile Leu Cys Asp
    50                  55                  60

Glu Val Ile Cys Glu Asp Thr Ser Asp Cys Pro Asn Ala Glu Ile Pro
65                  70                  75                  80

Phe Gly Glu Cys Cys Pro Ile Cys Pro Asp Val Asp Ala Ser Pro Val
                85                  90                  95

Tyr Pro Glu Ser Ala Gly Val Glu Gly Pro Lys Gly Asp Thr Gly Pro
            100                 105                 110
```

-continued

```
Arg Gly Asp Arg Gly Leu Pro Gly Pro Pro Gly Arg Asp Gly Ile Pro
            115                 120                 125
Gly Gln Pro Gly Leu Pro Gly Pro Pro Gly Pro Pro Gly
        130                 135                 140
Leu Gly Gly Asn Phe Ala Pro Gln Met Ser Tyr Gly Tyr Asp Glu Lys
145                 150                 155                 160
Ser Ala Gly Val Ala Val Pro Gly Pro Met Gly Pro Ala Gly Pro Arg
                165                 170                 175
Gly Leu Pro Gly Pro Pro Gly Ala Pro Gly Pro Gln Gly Phe Gln Gly
            180                 185                 190
Pro Pro Gly Glu Pro Gly Glu Pro Gly Ala Ser Gly Pro Met Gly Pro
        195                 200                 205
Arg Gly Pro Ala Gly Pro Pro Gly Lys Asn Gly Asp Asp Gly Glu Ala
    210                 215                 220
Gly Lys Pro Gly Arg Pro Gly Gln Arg Gly Pro Pro Gly Pro Gln Gly
225                 230                 235                 240
Ala Arg Gly Leu Pro Gly Thr Ala Gly Leu Pro Gly Met Lys Gly His
                245                 250                 255
Arg Gly Phe Ser Gly Leu Asp Gly Ala Lys Gly Gln Pro Gly Pro Ala
            260                 265                 270
Gly Pro Lys Gly Glu Pro Gly Ser Pro Gly Glu Asn Gly Ala Pro Gly
        275                 280                 285
Gln Met Gly Pro Arg Gly Leu Pro Gly Glu Arg Gly Arg Pro Gly Pro
    290                 295                 300
Ser Gly Pro Ala Gly Ala Arg Gly Asn Asp Gly Ala Pro Gly Ala Ala
305                 310                 315                 320
Gly Pro Pro Gly Pro Thr Gly Pro Ala Gly Pro Pro Gly Phe Pro Gly
                325                 330                 335
Ala Ala Gly Ala Lys Gly Glu Thr Gly Pro Gln Gly Ala Arg Gly Ser
            340                 345                 350
Glu Gly Pro Gln Gly Ser Arg Gly Glu Pro Gly Pro Pro Gly Pro Ala
        355                 360                 365
Gly Ala Ala Gly Pro Ala Gly Asn Pro Gly Ala Asp Gly Gln Pro Gly
    370                 375                 380
Ala Lys Gly Ala Thr Gly Ala Pro Gly Ile Ala Gly Ala Pro Gly Phe
385                 390                 395                 400
Pro Gly Ala Arg Gly Pro Ser Gly Pro Gln Gly Pro Ser Gly Ala Pro
                405                 410                 415
Gly Pro Lys Gly Asn Ser Gly Glu Pro Gly Ala Pro Gly Asn Lys Gly
            420                 425                 430
Asp Thr Gly Ala Lys Gly Glu Pro Gly Pro Ala Gly Val Gln Gly Pro
        435                 440                 445
Pro Gly Pro Ala Gly Glu Glu Gly Lys Arg Gly Ala Arg Gly Glu Pro
    450                 455                 460
Gly Pro Ala Gly Leu Pro Gly Pro Ala Gly Glu Arg Gly Ala Pro Gly
465                 470                 475                 480
Ser Arg Gly Phe Pro Gly Ala Asp Gly Ile Ala Gly Pro Lys Gly Pro
                485                 490                 495
Pro Gly Glu Arg Gly Ser Pro Gly Ala Val Gly Pro Lys Gly Ser Pro
            500                 505                 510
Gly Glu Ala Gly Arg Pro Gly Glu Ala Gly Leu Pro Gly Ala Lys Gly
        515                 520                 525
Leu Thr Gly Ser Pro Gly Ser Pro Gly Pro Asp Gly Lys Thr Gly Pro
```

```
                530             535             540
Pro Gly Pro Ala Gly Gln Asp Gly Arg Pro Gly Ala Gly Pro Pro
545                 550                 555                 560

Gly Ala Arg Gly Gln Ala Gly Val Met Gly Phe Pro Gly Pro Lys Gly
                565                 570                 575

Ala Ala Gly Glu Pro Gly Lys Pro Gly Glu Arg Gly Ala Pro Gly Pro
                580                 585                 590

Pro Gly Ala Val Gly Ala Ala Gly Lys Asp Gly Glu Ala Gly Ala Gln
                595                 600                 605

Gly Pro Pro Gly Pro Thr Gly Pro Ala Gly Glu Arg Gly Glu Gln Gly
                610                 615                 620

Pro Ala Gly Ala Pro Gly Phe Gln Gly Leu Pro Gly Pro Ala Gly Pro
625                 630                 635                 640

Pro Gly Glu Ala Gly Lys Pro Gly Glu Gln Gly Val Pro Gly Asn Ala
                645                 650                 655

Gly Ala Pro Gly Pro Ala Gly Ala Arg Gly Glu Arg Gly Phe Pro Gly
                660                 665                 670

Glu Arg Gly Val Gln Gly Pro Gly Pro Gln Gly Pro Arg Gly Ala
                675                 680                 685

Asn Gly Ala Pro Gly Asn Asp Gly Ala Lys Gly Asp Ala Gly Ala Pro
690                 695                 700

Gly Ala Pro Gly Asn Glu Gly Pro Pro Gly Leu Glu Gly Met Pro Gly
705                 710                 715                 720

Glu Arg Gly Ala Ala Gly Leu Pro Gly Ala Lys Gly Asp Arg Gly Asp
                725                 730                 735

Pro Gly Pro Lys Gly Ala Asp Gly Ala Pro Gly Lys Asp Gly Leu Arg
                740                 745                 750

Gly Leu Thr Gly Pro Ile Gly Pro Pro Gly Pro Ala Gly Ala Pro Gly
                755                 760                 765

Asp Lys Gly Glu Ala Gly Pro Pro Gly Pro Ala Gly Pro Thr Gly Ala
                770                 775                 780

Arg Gly Ala Pro Gly Asp Arg Gly Glu Pro Gly Pro Pro Gly Pro Ala
785                 790                 795                 800

Gly Phe Ala Gly Pro Pro Gly Ala Asp Gly Gln Pro Gly Ala Lys Gly
                805                 810                 815

Glu Thr Gly Asp Ala Gly Ala Lys Gly Asp Ala Gly Pro Pro Gly Pro
                820                 825                 830

Ala Gly Pro Thr Gly Ala Pro Gly Pro Ala Gly Glx Val Gly Ala Pro
                835                 840                 845

Gly Pro Lys Gly Ala Arg Gly Ser Ala Gly Pro Pro Gly Ala Thr Gly
                850                 855                 860

Phe Pro Gly Ala Ala Gly Arg Val Gly Pro Pro Gly Pro Ser Gly Asn
865                 870                 875                 880

Ile Gly Leu Pro Gly Pro Pro Gly Pro Ala Gly Lys Glx Gly Ser Lys
                885                 890                 895

Gly Pro Arg Gly Glu Thr Gly Pro Ala Gly Arg Pro Gly Glu Pro Gly
                900                 905                 910

Pro Ala Gly Pro Pro Gly Pro Pro Gly Glu Lys Gly Ser Pro Gly Ala
                915                 920                 925

Asp Gly Pro Ile Gly Ala Pro Gly Thr Pro Gly Pro Gln Gly Ile Ala
                930                 935                 940

Gly Gln Arg Gly Val Val Gly Leu Pro Gly Gln Arg Gly Glu Arg Gly
945                 950                 955                 960
```

Phe Pro Gly Leu Pro Gly Pro Ser Gly Glu Pro Gly Lys Gln Gly Pro
            965                 970                 975

Ser Gly Ala Ser Gly Glu Arg Gly Pro Pro Gly Pro Met Gly Pro Pro
            980                 985                 990

Gly Leu Ala Gly Pro Pro Gly Glu Ala Gly Arg Glu Gly Ala Pro Gly
            995                 1000                1005

Ala Glu Gly Ala Pro Gly Arg Asp Gly Ala Ala Gly Pro Lys Gly
        1010                1015                1020

Asp Arg Gly Glu Thr Gly Pro Ala Gly Pro Pro Gly Ala Pro Gly
        1025                1030                1035

Ala Pro Gly Ala Pro Gly Pro Val Gly Pro Ala Gly Lys Asn Gly
        1040                1045                1050

Asp Arg Gly Glu Thr Gly Pro Ala Gly Pro Ala Gly Pro Pro Gly
        1055                1060                1065

Pro Ala Gly Ala Arg Gly Pro Ala Gly Pro Gln Gly Pro Arg Gly
        1070                1075                1080

Asp Lys Gly Glu Thr Gly Glu Gln Gly Asp Arg Gly Met Lys Gly
        1085                1090                1095

His Arg Gly Phe Ser Gly Leu Gln Gly Pro Pro Gly Pro Pro Gly
        1100                1105                1110

Ala Pro Gly Glu Gln Gly Pro Ser Gly Ala Ser Gly Pro Ala Gly
        1115                1120                1125

Pro Arg Gly Pro Pro Gly Ser Ala Gly Ala Ala Gly Lys Asp Gly
        1130                1135                1140

Leu Asn Gly Leu Pro Gly Pro Ile Gly Pro Pro Gly Pro Arg Gly
        1145                1150                1155

Arg Thr Gly Glu Val Gly Pro Val Gly Pro Pro Gly Pro Pro Gly
        1160                1165                1170

Pro Pro Gly Pro Pro Gly Pro Ser Gly Gly Phe Asp Leu Ser
        1175                1180                1185

Phe Leu Pro Gln Pro Pro Gln Glu Lys Ala His Asp Gly Gly Arg
        1190                1195                1200

Tyr Tyr Arg Ala Asp Asp Ala Asn Val Met Arg Asp Arg Asp Leu
        1205                1210                1215

Glu Val Asp Thr Thr Leu Lys Ser Leu Ser Gln Gln Ile Glu Asn
        1220                1225                1230

Ile Arg Ser Pro Glu Gly Thr Arg Lys Asn Pro Ala Arg Thr Cys
        1235                1240                1245

Arg Asp Leu Lys Met Cys His Gly Asp Trp Lys Ser Gly Glu Tyr
        1250                1255                1260

Trp Ile Asp Pro Asn Gln Gly Cys Asn Leu Asp Ala Ile Lys Val
        1265                1270                1275

Tyr Cys Asn Met Glu Thr Gly Glu Thr Cys Val Tyr Pro Thr Gln
        1280                1285                1290

Ala Thr Ile Ala Gln Lys Asn Trp Tyr Leu Ser Lys Asn Pro Lys
        1295                1300                1305

Glu Lys Lys His Val Trp Phe Gly Glu Thr Met Ser Asp Gly Phe
        1310                1315                1320

Gln Phe Glu Tyr Gly Gly Glu Gly Ser Asn Pro Ala Asp Val Ala
        1325                1330                1335

Ile Gln Leu Thr Phe Leu Arg Leu Met Ser Thr Glu Ala Thr Gln
        1340                1345                1350

```
Asn Val Thr Tyr His Cys Lys Asn Ser Val Ala Tyr Met Asp His
    1355                1360                1365

Asp Thr Gly Asn Leu Lys Lys Ala Leu Leu Leu Gln Gly Ala Asn
    1370                1375                1380

Glu Ile Glu Ile Arg Ala Glu Gly Asn Ser Arg Phe Thr Tyr Gly
    1385                1390                1395

Val Thr Glu Asp Gly Cys Thr Ser His Thr Gly Ala Trp Gly Lys
    1400                1405                1410

Thr Val Ile Glu Tyr Lys Thr Thr Lys Thr Ser Arg Leu Pro Ile
    1415                1420                1425

Ile Asp Leu Ala Pro Met Asp Val Gly Ala Pro Asp Gln Glu Phe
    1430                1435                1440

Gly Ile Asp Ile Gly Pro Val Cys Phe Leu
    1445                1450

<210> SEQ ID NO 48
<211> LENGTH: 369
<212> TYPE: PRT
<213> ORGANISM: Gallus gallus

<400> SEQUENCE: 48

Gly Glu Thr Gly Glu Ala Gly Glu Arg Gly Leu Lys Gly His Arg Gly
1               5                   10                  15

Phe Thr Gly Leu Gln Gly Leu Pro Gly Pro Pro Gly Pro Ser Gly Asp
                20                  25                  30

Gln Gly Ala Ala Gly Pro Ala Gly Pro Ser Gly Pro Arg Gly Pro Pro
            35                  40                  45

Gly Pro Val Gly Pro Ser Gly Lys Asp Gly Ser Asn Gly Met Pro Gly
        50                  55                  60

Pro Ile Gly Pro Pro Gly Pro Arg Gly Arg Ser Gly Glu Pro Gly Pro
65                  70                  75                  80

Ala Gly Pro Pro Gly Asn Pro Gly Pro Pro Gly Pro Pro Gly Pro Pro
                85                  90                  95

Gly Thr Gly Ile Asp Met Ser Ala Phe Ala Gly Leu Gly Gln Thr Glu
            100                 105                 110

Lys Gly Pro Asp Pro Ile Arg Tyr Met Arg Ala Asp Glu Ala Ala Gly
        115                 120                 125

Gly Leu Arg Gln His Asp Val Glu Val Asp Ala Thr Leu Lys Ser Leu
    130                 135                 140

Asn Asn Gln Ile Glu Ser Ile Arg Ser Pro Glu Gly Ser Lys Lys Asn
145                 150                 155                 160

Pro Ala Arg Thr Cys Arg Asp Ile Lys Leu Cys His Pro Glu Trp Lys
                165                 170                 175

Ser Gly Asp Tyr Trp Ile Asp Pro Asn Gln Gly Cys Thr Leu Asp Ala
            180                 185                 190

Ile Lys Val Phe Cys Asn Met Glu Thr Gly Glu Thr Cys Val Tyr Pro
        195                 200                 205

Thr Pro Ser Ser Ile Pro Arg Lys Asn Trp Trp Thr Ser Lys Thr Lys
    210                 215                 220

Asp Lys Lys His Val Trp Phe Ala Glu Thr Ile Asn Gly Gly Phe His
225                 230                 235                 240

Phe Ser Tyr Gly Asp Glu Asn Leu Ser Pro Asn Thr Ala Ser Ile Gln
                245                 250                 255

Met Thr Phe Leu Arg Leu Leu Ser Thr Glu Gly Ser Gln Asn Val Thr
            260                 265                 270
```

| Tyr | His | Cys | Lys | Asn | Ser | Ile | Ala | Tyr | Met | Asp | Glu | Thr | Gly | Asn |
|---|---|---|---|---|---|---|---|---|---|---|---|---|---|---|
| | | 275 | | | | | 280 | | | | 285 | | | |

Leu Lys Lys Ala Ile Leu Ile Gln Gly Ser Asn Asp Val Glu Ile Arg
290             295             300

Ala Glu Gly Asn Ser Arg Phe Thr Tyr Ser Val Leu Glu Asp Gly Cys
305             310             315             320

Thr Lys His Thr Gly Lys Trp Gly Lys Thr Val Ile Glu Tyr Arg Ser
        325             330             335

Gln Lys Thr Ser Arg Leu Pro Ile Val Asp Ile Ala Pro Met Asp Ile
            340             345             350

Gly Gly Ala Asp Gln Glu Phe Gly Val Asp Ile Gly Pro Val Cys Phe
            355             360             365

Leu

```
<210> SEQ ID NO 49
<211> LENGTH: 1362
<212> TYPE: PRT
<213> ORGANISM: Gallus gallus
<220> FEATURE:
<221> NAME/KEY: misc_feature
<222> LOCATION: (246)..(262)
<223> OTHER INFORMATION: Xaa can be any naturally occurring amino acid
<220> FEATURE:
<221> NAME/KEY: misc_feature
<222> LOCATION: (449)..(466)
<223> OTHER INFORMATION: Xaa can be any naturally occurring amino acid

<400> SEQUENCE: 49
```

Met Leu Ser Phe Val Asp Thr Arg Ile Leu Leu Leu Ala Val Thr
1               5                   10                  15

Ser Tyr Leu Ala Thr Ser Gln His Val Ser Glu Ala Ser Ala Gly Arg
            20                  25                  30

Lys Gly Pro Arg Gly Asp Lys Gly Pro Gln Gly Glu Arg Gly Pro Pro
            35                  40                  45

Gly Pro Pro Gly Arg Asp Gly Glu Asp Gly Pro Pro Gly Pro Pro Gly
50                  55                  60

Pro Pro Gly Pro Pro Gly Leu Gly Gly Asn Phe Ala Ala Gln Tyr Asp
65                  70                  75                  80

Pro Ser Lys Ala Ala Asp Phe Gly Pro Gly Pro Met Gly Leu Met Gly
            85                  90                  95

Pro Arg Gly Pro Pro Gly Ala Ser Gly Pro Pro Gly Pro Pro Gly Phe
            100                 105                 110

Gln Gly Val Pro Gly Glu Pro Gly Glu Pro Gly Gln Thr Gly Pro Gln
            115                 120                 125

Gly Pro Arg Gly Pro Pro Gly Pro Pro Gly Lys Ala Gly Glu Asp Gly
            130                 135                 140

His Pro Gly Lys Pro Gly Arg Pro Gly Glu Arg Gly Val Ala Gly Pro
145                 150                 155                 160

Gln Gly Ala Arg Gly Phe Pro Gly Thr Pro Gly Pro Pro Gly Phe Lys
            165                 170                 175

Gly Ile Arg Gly His Asn Gly Leu Asp Gly Leu Thr Gly Gln Pro Gly
            180                 185                 190

Ala Pro Gly Thr Lys Gly Glu Pro Gly Ala Pro Gly Glu Asn Gly Thr
            195                 200                 205

Pro Gly Gln Pro Gly Ala Arg Gly Leu Pro Gly Glu Arg Gly Arg Ile
            210                 215                 220

```
Gly Ala Pro Gly Pro Ala Gly Ala Arg Gly Ser Asp Gly Ser Ala Gly
225                 230                 235                 240

Pro Thr Gly Pro Ala Xaa Xaa Xaa Xaa Xaa Xaa Xaa Xaa Xaa Xaa Xaa
            245                 250                 255

Xaa Xaa Xaa Xaa Xaa Xaa Gly Glu Ile Gly Pro Ala Gly Asn Glu Gly
                260                 265                 270

Pro Thr Gly Pro Ala Gly Pro Arg Gly Glu Ile Gly Leu Pro Gly Ser
        275                 280                 285

Ser Gly Pro Val Gly Pro Gly Asn Pro Gly Ala Asn Gly Leu Pro
    290                 295                 300

Gly Ala Lys Gly Ala Ala Gly Leu Pro Gly Val Ala Gly Ala Pro Gly
305                 310                 315                 320

Leu Pro Gly Pro Arg Gly Ile Pro Gly Pro Pro Gly Pro Ala Gly Pro
                325                 330                 335

Ser Gly Ala Arg Gly Leu Val Gly Glu Pro Gly Pro Ala Gly Ala Lys
            340                 345                 350

Gly Glu Ser Gly Asn Lys Gly Glu Pro Gly Ala Ala Gly Pro Pro Gly
        355                 360                 365

Pro Pro Gly Pro Ser Gly Glu Glu Gly Lys Arg Gly Ser Asn Gly Glu
370                 375                 380

Pro Gly Ser Ala Gly Pro Pro Gly Pro Ala Gly Leu Arg Gly Glu Pro
385                 390                 395                 400

Gly Ser Arg Gly Leu Pro Gly Ala Asp Gly Arg Ala Gly Val Met Gly
                405                 410                 415

Pro Ala Gly Asn Arg Gly Ala Ser Gly Pro Val Gly Ala Lys Gly Pro
                420                 425                 430

Asn Gly Asp Ala Gly Arg Pro Gly Glu Pro Gly Leu Met Gly Pro Arg
                435                 440                 445

Xaa Xaa Xaa Xaa Xaa Xaa Xaa Xaa Xaa Xaa Xaa Xaa Xaa Xaa Xaa
    450                 455                 460

Xaa Xaa Gly Phe Pro Gly Ala Asp Gly Arg Val Gly Pro Ile Gly Pro
465                 470                 475                 480

Ala Gly Asn Arg Gly Glu Pro Gly Asn Ile Gly Phe Pro Gly Pro Lys
            485                 490                 495

Gly Pro Thr Gly Glu Pro Gly Lys Pro Gly Glu Lys Gly Asn Val Gly
        500                 505                 510

Leu Ala Gly Pro Arg Gly Ala Pro Gly Pro Glu Gly Asn Asn Gly Ala
    515                 520                 525

Gln Gly Pro Pro Gly Val Thr Gly Asn Gln Gly Ala Lys Gly Glu Thr
530                 535                 540

Gly Pro Ala Gly Pro Pro Gly Phe Gln Gly Leu Pro Gly Pro Ser Gly
545                 550                 555                 560

Pro Ala Gly Glu Ala Gly Lys Pro Gly Glu Arg Gly Leu His Gly Glu
                565                 570                 575

Phe Gly Val Pro Gly Pro Ala Gly Pro Arg Gly Glu Arg Gly Leu Pro
        580                 585                 590

Gly Glu Ser Gly Ala Val Gly Pro Ala Gly Pro Ile Gly Ser Arg Gly
            595                 600                 605

Pro Ser Gly Pro Pro Gly Pro Asp Gly Asn Lys Gly Glu Pro Gly Asn
        610                 615                 620

Val Gly Pro Ala Gly Ala Pro Gly Pro Ala Gly Pro Gly Gly Ile Pro
625                 630                 635                 640

Gly Glu Arg Gly Val Ala Gly Val Pro Gly Gly Lys Gly Glu Lys Gly
```

```
                    645                 650                 655
Ala Pro Gly Leu Arg Gly Asp Thr Gly Ala Thr Gly Arg Asp Gly Ala
                660                 665                 670
Arg Gly Leu Pro Gly Ala Ile Gly Ala Pro Gly Pro Ala Gly Gly Ala
                675                 680                 685
Gly Asp Arg Gly Glu Gly Gly Pro Ala Gly Pro Ala Gly Pro Ala Gly
                690                 695                 700
Ala Arg Gly Ile Pro Gly Glu Arg Gly Glu Pro Gly Pro Val Gly Pro
705                 710                 715                 720
Ser Gly Phe Ala Gly Pro Pro Gly Ala Ala Gly Gln Pro Gly Ala Lys
                725                 730                 735
Gly Glu Arg Gly Pro Lys Gly Pro Lys Gly Glu Thr Gly Pro Thr Gly
                740                 745                 750
Ala Ile Gly Pro Ile Gly Ala Ser Gly Pro Pro Gly Pro Val Gly Ala
                755                 760                 765
Ala Gly Pro Ala Gly Pro Arg Gly Asp Ala Gly Pro Pro Gly Met Thr
                770                 775                 780
Gly Phe Pro Gly Ala Ala Gly Arg Val Gly Pro Pro Gly Pro Ala Gly
785                 790                 795                 800
Ile Thr Gly Pro Pro Gly Pro Pro Gly Ala Gly Lys Asp Gly Pro
                805                 810                 815
Arg Gly Leu Arg Gly Asp Val Gly Pro Val Gly Arg Thr Gly Glu Gln
                820                 825                 830
Gly Ile Ala Gly Pro Pro Gly Phe Ala Gly Glu Lys Gly Pro Ser Gly
                835                 840                 845
Glu Ala Gly Ala Ala Gly Pro Pro Gly Thr Pro Gly Pro Gln Gly Ile
850                 855                 860
Leu Gly Ala Pro Gly Ile Leu Gly Leu Pro Gly Ser Arg Gly Glu Arg
865                 870                 875                 880
Gly Leu Pro Gly Ile Ala Gly Ala Thr Gly Glu Pro Gly Pro Leu Gly
                885                 890                 895
Val Ser Gly Pro Pro Gly Ala Arg Gly Pro Ser Gly Pro Val Gly Ser
                900                 905                 910
Pro Gly Pro Asn Gly Ala Pro Gly Glu Ala Gly Arg Asp Gly Asn Pro
                915                 920                 925
Gly Asn Asp Gly Pro Pro Gly Arg Asp Gly Ala Pro Gly Phe Lys Gly
                930                 935                 940
Glu Arg Gly Ala Pro Gly Asn Pro Gly Pro Ser Gly Ala Leu Gly Ala
945                 950                 955                 960
Pro Gly Pro His Gly Gln Val Gly Pro Ser Gly Lys Pro Gly Asn Arg
                965                 970                 975
Gly Asp Pro Gly Pro Val Gly Pro Val Gly Pro Ala Gly Ala Phe Gly
                980                 985                 990
Pro Arg Gly Leu Ala Gly Pro Gln Gly Pro Arg Gly Glu Lys Gly Glu
                995                 1000                1005
Pro Gly Asp Lys Gly His Arg Gly Leu Pro Gly Leu Lys Gly His
                1010                1015                1020
Asn Gly Leu Gln Gly Leu Pro Gly Leu Ala Gly Gln His Gly Asp
                1025                1030                1035
Gln Gly Pro Pro Gly Asn Asn Gly Pro Ala Gly Pro Arg Gly Pro
                1040                1045                1050
Pro Gly Pro Ser Gly Pro Pro Gly Lys Asp Gly Arg Asn Gly Leu
                1055                1060                1065
```

```
Pro Gly Pro Ile Gly Pro Ala Gly Val Arg Gly Ser His Gly Ser
    1070            1075                1080

Gln Gly Pro Ala Gly Pro Pro Gly Pro Pro Gly Pro Pro Gly Pro
    1085            1090                1095

Pro Gly Pro Asn Gly Gly Gly Tyr Glu Val Gly Phe Asp Ala Glu
    1100            1105                1110

Tyr Tyr Arg Ala Asp Gln Pro Ser Leu Arg Pro Lys Asp Tyr Glu
    1115            1120                1125

Val Asp Ala Thr Leu Lys Thr Leu Asn Asn Gln Ile Glu Thr Leu
    1130            1135                1140

Leu Thr Pro Glu Gly Ser Lys Lys Asn Pro Ala Arg Thr Cys Arg
    1145            1150                1155

Asp Leu Arg Leu Ser His Pro Glu Trp Ser Ser Gly Phe Tyr Trp
    1160            1165                1170

Ile Asp Pro Asn Gln Gly Cys Thr Ala Asp Ala Ile Arg Ala Tyr
    1175            1180                1185

Cys Asp Phe Ala Thr Gly Glu Thr Cys Ile His Ala Ser Leu Glu
    1190            1195                1200

Asp Ile Pro Thr Lys Thr Trp Tyr Val Ser Lys Asn Pro Lys Asp
    1205            1210                1215

Lys Lys His Ile Trp Phe Gly Glu Thr Ile Asn Gly Gly Thr Gln
    1220            1225                1230

Phe Glu Tyr Asn Gly Glu Gly Val Thr Thr Lys Asp Met Ala Thr
    1235            1240                1245

Gln Leu Ala Phe Met Arg Leu Leu Ala Asn His Ala Ser Gln Asn
    1250            1255                1260

Ile Thr Tyr His Cys Lys Asn Ser Ile Ala Tyr Met Asp Glu Glu
    1265            1270                1275

Thr Gly Asn Leu Lys Lys Ala Val Ile Leu Gln Gly Ser Asn Asp
    1280            1285                1290

Val Glu Leu Arg Ala Glu Gly Asn Ser Arg Phe Thr Phe Ser Val
    1295            1300                1305

Leu Val Asp Gly Cys Ser Lys Lys Asn Asn Lys Trp Gly Lys Thr
    1310            1315                1320

Ile Ile Glu Tyr Arg Thr Asn Lys Pro Ser Arg Leu Pro Ile Leu
    1325            1330                1335

Asp Ile Ala Pro Leu Asp Ile Gly Gly Ala Asp Gln Glu Phe Gly
    1340            1345                1350

Leu His Ile Gly Pro Val Cys Phe Lys
    1355            1360
```